(12) United States Patent
Shinkai et al.

(10) Patent No.: US 6,753,346 B2
(45) Date of Patent: *Jun. 22, 2004

(54) CETP ACTIVITY INHIBITOR

(75) Inventors: Hisashi Shinkai, Osaka (JP); Kimiya Maeda, Osaka (JP); Hiroshi Okamoto, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/151,813

(22) Filed: May 22, 2002

(65) Prior Publication Data

US 2003/0092708 A1 May 15, 2003

Related U.S. Application Data

(63) Continuation of application No. 09/367,299, filed as application No. PCT/JP98/00542 on Feb. 10, 1998, now Pat. No. 6,426,365.

(30) Foreign Application Priority Data

Feb. 12, 1997 (JP) ............................................. 9/44836
Jun. 5, 1997 (JP) ............................................ 9/165085
Jan. 23, 1998 (JP) ............................................ 10-26688

(51) Int. Cl.⁷ ....................... A61K 31/255; C07C 327/26
(52) U.S. Cl. ....................................... 514/489; 558/257
(58) Field of Search ................................. 558/234, 236, 558/240, 241, 242, 246, 250, 258, 256, 257; 514/489

(56) References Cited

U.S. PATENT DOCUMENTS

| | | | |
|---|---|---|---|
| 3,576,830 A | | 4/1971 | Toshitsugu et al. ...... 260/402.5 |
| 4,740,438 A | * | 4/1988 | Krishnamurthy ............. 430/17 |
| 4,853,319 A | | 8/1989 | Krishnamurthy et al. ..... 430/17 |
| 5,118,583 A | | 6/1992 | Kondo et al. ................ 430/309 |
| 5,194,539 A | | 3/1993 | Charmot ...................... 526/220 |
| 5,217,859 A | | 6/1993 | Boettcher et al. ........... 430/569 |
| 5,219,721 A | | 6/1993 | Klaus et al. ................. 430/569 |
| 5,350,667 A | | 9/1994 | Singer et al. ............... 430/387 |
| 5,405,969 A | | 4/1995 | Wright et al. ............... 548/250 |
| 5,446,207 A | | 8/1995 | Pomponi et al. ............ 568/633 |
| 5,504,097 A | | 4/1996 | Malamas et al. ........... 514/365 |
| 5,534,529 A | | 7/1996 | Yoshida et al. ............ 514/357 |
| 5,542,974 A | | 8/1996 | Buding ....................... 106/270 |
| 5,556,888 A | | 9/1996 | Koda et al. ................ 521/44.5 |
| 5,614,550 A | | 3/1997 | Yoshida et al. ............ 514/450 |
| 5,654,134 A | | 8/1997 | Morimura et al. .......... 430/603 |
| 5,698,564 A | | 12/1997 | Katsuyama et al. ....... 514/275 |
| 5,776,951 A | | 7/1998 | Arrowsmith et al. ....... 514/328 |
| 5,925,645 A | | 7/1999 | Schmidt et al. ............. 514/277 |

FOREIGN PATENT DOCUMENTS

| | | |
|---|---|---|
| CA | 2000631 | 4/1990 |
| JP | 45-11132 | 4/1970 |
| JP | 47-35786 | 12/1972 |
| JP | 1-278543 | 11/1989 |
| JP | 1-321432 | 12/1989 |
| JP | 2-23338 | 1/1990 |
| JP | 3-226750 | 10/1991 |
| WO | WO 92/03408 | 5/1992 |
| WO | WO 92/03412 | 5/1992 |
| WO | WO 96/09406 | 3/1996 |

OTHER PUBLICATIONS

Antonova, A. et al "Synthesis of S–[2(2–Substituted phenylsulfonamido)phenyl]esters . . . " Dokl. Bulg. Akad. Nauk., (1993) vol. 46, No. 1, pp. 71–74.*

Drozd, V. "Thermal rearrangement of O–thioacyl derivatives . . . " Z. Org. Khim. (1987) vol 23, No. 2, pp. 355–365.*

Hori, M. et al "A new ring transformation of benzothiazolines . . . " Heterocycles (1978) vol 9, No. 10, pp. 1413–1418.*

Simov, D. et al "Reaction of 3–benzenesulfonylbenzothiazolines . . . " Khim. Getero. Soed. (1976) No. 9, pp. 1192–1195.*

(List continued on next page.)

Primary Examiner—James O. Wilson
Assistant Examiner—Leigh C. Maier
(74) Attorney, Agent, or Firm—Leydig, Voit & Mayer, Ltd.

(57) ABSTRACT

The present invention provides a CETP activity inhibitor comprising as an active ingredient a compound represented by the formula (I):

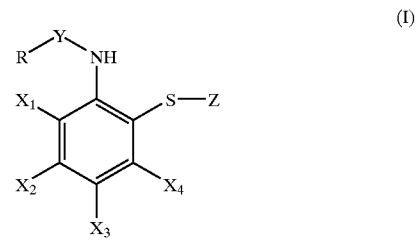

wherein R represents a straight chain or branched alkyl group; a straight chain or branched alkenyl group; a lower haloalkyl group; a substituted or unsubstituted cycloalkyl group; a substituted or unsubstituted cycloalkenyl group; a substituted or unsubstituted cycloalkylalkyl group; a substituted or unsubstituted aryl group, or a substituted or unsubstituted heterocyclic group, $X_1$, $X_2$, $X_3$, and $X_4$ may be the same or different and each represents a hydrogen atom, a halogen atom, a lower alkyl group, a lower haloalkyl group; a lower alkoxy group; a cyano group; a nitro group; an acyl group; or an aryl group, Y represents —CO— or —$SO_2$—, and Z represents a hydrogen atom or a mercapto-protecting group, or a prodrug compound, a pharmaceutically acceptable salt, or hydrate or solvate thereof. The compounds represented by the formula (I) can increase HDL and at the same time decrease LDL through selective inhibition of CETP activity and, therefore, is expected to be useful as a new type of a preventive or therapeutic agent for atherosclerosis or hyperlipidemia.

17 Claims, No Drawings

OTHER PUBLICATIONS

Nagarajan, K. et al "Condensed heterocycles" Indian J. Chem. (1974) vol 12, No. 3, pp. 227–235.*

Connolly, D.T., et al., Biochem. Biophys. Res. Com., vol. 223, pp. 42–47, 1996.

Egan, R. W., et al. "Specific Inhibition and Oxidative Regulation of 5–Lipoxygenase" Adv. Prostaglandin, Thromboxane, and Leukotriene Res. vol. 11, pp. 151–157, (1983).

* cited by examiner

CETP ACTIVITY INHIBITOR

This application is a continuation of U.S. application Ser. No. 09/367,299, filed on Dec. 23, 1999, now U.S. Pat. No. 6,426,365, which is the U.S. national phase of International Patent Application PCT/JP98/00542, filed on Feb. 10, 1998.

TECHNICAL FIELD

This invention relates to a novel CETP activity inhibitor which comprises as an active ingredient a compound having a bis-(2-aminophenyl) disulfide structure or a 2-aminophenylthio structure and more particularly to a pharmaceutical composition for treating or preventing atherosclerosis or hyperlipidemia. This invention also relates to a compound having a bis-(2-aminophehyl) disulfide structure or a 2-aminophenylthio structure, a prodrug compound, a pharmaceutically acceptable salt, hydrates or solvates of these compounds.

BACKGROUND ART

From the results of many epidemiological studies, it has been considered that there exists certain relation between atherosclerotic diseases and serum lipoprotein. For example, Badimon et al. (J. Clin. Invest. 85, 1234–1241 (1990)) reported that not only the prevention of development but also regression of atherosclerotic lesions were observed after intravenous injection of fractions containing HDL (high density lipoprotein) and VHDL (very high density lipoprotein) to cholesterol-loaded rabbits. Thus, regarding the relation between atherosclerotic diseases and serum lipoproteins, it is expected that HDL and VHDL may have antiatherosclerotic activity.

Recently, it has been elucidated that there are proteins that transfer lipids among serum lipoproteins, i.e., CETP (cholesterol ester transfer protein). The presence of CETP was first indicated by Nichols and Smith in 1965 (J. Lipid Res. 6, 206 (1965)). cDNA of the protein was later cloned by Drayna et al. in 1987. Molecular weight of the protein as glycoprotein is 74,000 Da. It is about 58,000 Da after complete removal of sugar chain. cDNA of this protein is composed of 1656 nucleotide residues and codes for 476 amino acids following signal peptide of 17 amino acid residues. Since around 44% of these amino acids are hydrophobic, the protein is highly hydrophobic and liable to be inactivated by oxidation. CETP is synthesized in organs like liver, spleen, adrenal, fat tissue, small intestine, kidney, skeletal muscle, and myocardium. It has been confirmed that CETP is synthesized in cells like macrophages derived from human monocytes, B lymphocytes, fat cells, small intestinal epithelial cells, $CaCo_2$ cells, and liver cells (for example, HepG2 cells derived from human hepatoma cells). In addition to these tissues, it is present in cerebrospinal fluid and seminal fluid, too. The presence is also confirmed in culture media of neuroblastoma and neuroglioma cells, and in chorioid plexus of sheep.

It has become apparent that CETP participates in metabolism of all the lipoproteins in vivo and plays important roles in reverse transfer system of cholesterol. It attracted attention as a system that prevents the accumulation of cholesterol into peripheral cells and functions as protective mechanism against atherosclerosis. In relation to HDL, which plays important roles in the reverse transfer system of cholesterol, a great number of epidemiological studies have shown that a decrease in CE (cholesterol esters) of HDL in blood represents one of the risk factors for coronary artery diseases. Activity of CETP differ depending on the species of animals and it has become apparent that cholesterol load does not bring about atherosclerosis in animals with low CETP activity, while it is easily produced in animals with high CETP activity. Absence of CETP results in high HDL-emia+low LDL (low density lipoprotein)-emia and brings about a state resistant to atherosclerosis. Thus, the importance of CETP as mediators of transfer of CE in HDL to blood LDL has become recognized in addition to the importance of HDL in blood.

Free cholesterol (FC) synthesized in the liver and secreted therefrom is taken up into very low density lipoprotein (VLDL). Next, VLDL is metabolized in the blood to LDL via intermediate density lipoprotein (IDL) by the action of lipoprotein lipase (LPL) and liver triglyceride lipase (HTGL). LDL is taken up to peripheral cells mediated by LDL receptor and, thus, FC is supplied to the cells.

Contrary to this flow from the liver to peripheral cells, there exists another flow of cholesterol from peripheral cells to the liver called cholesterol reverse transfer system. FC accumulated in peripheral cells is extracted by HDL, esterified on HDL through the action of LCAT (Lecithin: cholesterol acyltransferase) to form CE, transferred to the hydrophobic core portion of HDL, and HDL becomes matured to globular HDL particles. CE in HDL is transferred to apoB-containing lipoproteins such as VLDL, IDL, and LDL by CETP present in the blood. In exchange, TG is transferred to HDL in mole ratio of 1:1. CE that is transferred to apoB-containing lipoprotein is taken up by the liver via LDL receptor on it and, thus, cholesterol is transferred indirectly to the liver. There is mechanisms, too, by which HDL becomes CE-rich, apoprotein E-containing HDL by taking up apoprotein E secreted by macrophages and the like, which is then taken up directly to the liver via LDL receptor or remnant receptor. In another, the liver cells do not take up HDL particles, but take up selectively only CE in HDL. In still another, HDL particles are taken up by the liver cells via so-called HDL receptor.

In a state, in which CETP activity is augmented, CE in HDL is decreased and CE in VLDL, IDL and LDL is increased due to augmentation of CE transfer from HDL. Increases in uptake of IDL and LDL to the liver result in down-regulation of LDL receptor and increases in LDL in the blood. In contrast, in a state of CETP deficiency, HDL removes cholesterol from peripheral cells with the aid of LCAT, increases its size gradually and acquires apoE. HDL that becomes apoE-rich is taken up by the liver via LDL receptor of the liver and catabolized. However, as the operation of this mechanism is not adequate in the human, retention of large HDL in the blood occurs and, as a result, cholesterol pool in the liver becomes smaller. LDL receptor becomes up-regulated and LDL is decreased.

Hence, by selectively inhibiting CETP, it is possible to decrease IDL, VLDL, and LDL that accelerate atherosclerosis and increase HDL that exhibits inhibitory action. Thus, it is anticipated that hitherto non-existent drugs useful for prevention or therapy of atherosclerosis or hyperlipidemia may be provided.

Very recently there have been reports on chemical compounds that aim at inhibition of such CETP activity.

For example, in Biochemical and Biophysical Research Communications ZZS, 42–47 (1996), dithiodipyridine derivatives and substituted dithiobenzene derivatives are disclosed as compounds capable of inactivating CETP through modification of cysteine residues. However, the literature neither discloses nor suggests the compounds such as those of the present invention which have a bis-(2-aminophenyl) disulfide structure or a 2-aminophenylthio structure.

WO95/06626 discloses Wiedendiol-A and Wiedendiol-B as CETP activity inhibitors, but there is no description suggesting the compounds of the present invention.

Furthermore, in JP-B-Sho 45-11132, JP-B-Sho 45-2892, JP-B-Sho 45-2891, JP-B-Sho 45-2731, and JP-B-Sho 45-2730, mercaptoanilides substituted with higher fatty acids such as o-isostearoylamino thiophenol are disclosed. However, in these publications, the atherosclerosis-preventing action is only referred to and there is no description of test examples that substantiate the action. There is also no description of CETP inhibitory activity. Nor is there description suggestive of compounds of the present invention.

There are several reports on the compounds having a bis-(2-aminophenyl) disulfide structure or a 2-aminophenylthio structure similar to those of the present application of invention.

For example, WO96/09406 discloses disulfide compounds such as 2-acetylaminophenyl disulfide and the like. However, the compounds of the publication are the ones that are useful for retrovirus, i.e., HIV-1, and usefulness as regards inhibitors of CETP activity has not been disclosed. There also is no description suggestive of the usefulness.

In JP-A-Hei 8-253454, diphenyl disulfide compounds such as 2,2'-di(pyrimidylamino)diphenyldisulfide and the like are disclosed. However, the compounds in this publication are the ones that have inhibitory action on production of IL-1β and on release of TNFα and there are no disclosure as regards the usefulness as inhibitors of CETP activity. There is even no description suggestive of the usefulness.

In JP-A-Hei 2-155937, bis-(acylaminophenyl) disulfide compounds such as 2,2'-diacetylaminodiphenyl disulfide and the like are disclosed. However, the compounds in this publication relates to the method of making vulcanized rubber filled with carbon black and there are no disclosure as regards the usefulness as inhibitors of CETP activity. There is also no description suggestive of the usefulness. In the claims recited in the publication, $C_1$–$C_{12}$ cycloalkyl and cycloalkenyl are defined as $R^9$ and $R^{10}$, and as specific examples cyclohexyl and cyclohexenyl are described. However, in the publication no example that substantiates the use of the compound is shown and there is no description of the general method of production of the compounds.

JP-A-Hei 2-501772 discloses acylamino phenyl disulfide derivatives such as o-pivaloylaminophenyl disulfide and the like as intermediates for production of pyrazolone photocoupler. However, the invention described in this publication relates to the photo-element and not suggestive of the present invention. This publication also describes 2-cyclohexane carbonylamino phenylthio group as an example of coupling-off group of the coupler, but there is no description of examples that substantiate the use of the compound.

JP-A-Hei 8-171167 discloses thiophenol derivatives or disulfide derivatives such as 2-acetylamino thiophenol. However, the invention described in this publication relates to the silver halide emulsion and not suggestive of the present invention.

In JP-A-Hei 4-233908, disulfide derivatives such as bis-(2-acetoamidephenyl) disulfide and the like are disclosed. However, the compounds of this publication is disclosed as chain transfer agents and, thus, the publication does not suggest the present invention. As specific examples of $R_3$ in X,Y, a cyclohexyl group is disclosed, but the example substantiating the use and the general method of production are not described.

JP-A-Sho 63-157150 discloses amidophenyl disulfide derivatives such as o-pivalamidophenyl disulfide and the like as stabilizers. However, the invention of this publication relates to photo-element and is not suggestive of the present invention. In the claim recited in this publication, a cycloalkyl group is defined as R in the substituents V or Y of the stabilizer compounds, but the example substantiating the use and the general method of production are not described.

Bis-(amidophenyl) disulfide derivatives are also disclosed in JP-A-Hei 8-59900, JP-A-Hei 7-258472, JP-A-Hei 7-224028, JP-A-Hei 7-49554, JP-A-Hei 6-19037, JP-A-Hei 6-19024, JP-A-Hei 3-226750, JP-A-Hei 2-284146, JP-A-Hei 2-23338, JP-A-Hei 1-321432, JP-A-Hei 1-278543, and JP-B-Sho 47-357786. However, none of them discloses usefulness as inhibitors of CETP activity and there is no description suggestive of the usefulness.

DISCLOSURE OF THE INVENTION

As described above, the present inventors studied ardently in order to provide the compounds that selectively inhibit CETP activity and, as a result, found compounds useful as novel preventive or therapeutic agents of atherosclerosis or hyperlipidemia with new action mechanism which could increase HDL and at the same time decrease LDL, thereby completing the present invention.

The present invention relates to the compounds and medicaments as shown in the following (1) to (19) which have CETP activity inhibitory effect.

(1) A CETP activity inhibitor comprising as an active ingredient a compound represented by the formula (I):

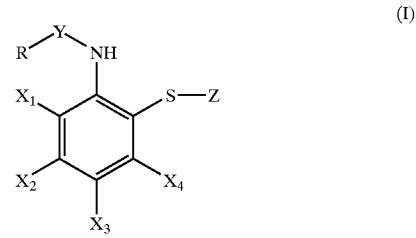

wherein
R represents
  a straight chain or branched $C_{1-10}$ alkyl group;
  a straight chain or branched $C_{2-10}$ alkenyl group;
  a halo-$C_{1-4}$ lower alkyl group;
  a substituted or unsubstituted $C_{3-10}$ cycloalkyl group;
  a substituted or unsubstituted $C_{1-8}$ cycloalkenyl group;
  a substituted or unsubstituted $C_{3-10}$ cycloalkyl $C_{10}$ alkyl group;
  a substituted or unsubstituted aryl group;
  a substituted or unsubstituted aralkyl group; or
  a substituted or unsubstituted 5- or 6-membered heterocyclic group having 1–3 nitrogen, oxygen or sulfur atoms, $X_1$, $X_2$, $X_3$, and $X_4$ may be the same or different and represents
  a hydrogen atom;
  a halogen atom;
  a $C_{1-4}$ lower alkyl group;
  a halo-$C_{1-4}$ lower alkyl group;
  a $C_{1-4}$ lower alkoxy group;
  a cyano group;
  a nitro group;
  an acyl group; or
  an aryl group, Y represents
—CO—; or
—SO$_2$, and Z represents
a hydrogen atom; or
a mercapto-protecting group,
a prodrug compound, a pharmaceutically acceptable salt, hydrate, or solvate thereof.

(2) A CETP activity inhibitor comprising as an active ingredient the compound described in the above (1), wherein
R represents
a straight chain or branched C$_{1-10}$ alkyl group;
a straight chain or branched C$_{2-10}$ alkenyl group;
a halo-C$_{1-4}$ lower alkyl group substituted with 1–3 halogen atoms selected from fluorine, chlorine, and bromine;
a C$_{3-10}$ cycloalkyl group, a C$_{5-8}$ cycloalkenyl group, or a C$_{3-10}$ cycloalkyl C$_{1-10}$ alkyl group, each of which may have 1–4 substituents selected from the group consisting of
a straight chain or branched C$_{1-10}$ alkyl group,
a straight chain or branched C$_{2-10}$ alkenyl group,
a C$_{3-10}$ cycloalkyl group,
a C$_{5-8}$ cycloalkenyl group,
a C$_{3-10}$ cycloalkyl C$_{1-10}$ alkyl group,
an aryl group selected from phenyl, biphenyl, and naphthyl,
an oxo group, and
an aralkyl group having an aryl group selected from phenyl, biphenyl, and naphthyl; or
an aryl, aralkyl, or 5- or 6-membered heterocyclic group with 1–3 nitrogen, oxygen or sulfur atoms, each of which may have 1–4 substituents selected from the group consisting of
a straight chain or branched C$_{1-10}$ alkyl group,
a straight chain or branched C$_{2-10}$ alkenyl group,
a halogen atom selected from fluorine, chlorine, and bromine,
a nitro group, and
a halo-C$_{1-4}$ lower alkyl group having a halogen atom selected from fluorine, chlorine, and bromine;
Z represents
a hydrogen atom;
a mercapto-protecting group selected from the group consisting of
a C$_{1-4}$ lower alkoxymethyl group,
a C$_{1-4}$ lower alkylthiomethyl group,
an aralkyloxymethyl group having an aryl group selected from phenyl, biphenyl, and naphthyl,
an aralkylthiomethyl group having an aryl group selected from phenyl, biphenyl, and naphthyl,
a C$_{3-10}$ cycloalkyloxymethyl group,
a C$_{5-8}$ cycloalkenyloxymethyl group,
a C$_{3-10}$ cycloalkyl C$_{10}$ alkoxymethyl group,
an aryloxymethyl group having an aryl group selected from phenyl, biphenyl, and naphthyl,
an arylthiomethyl group having an aryl group selected from phenyl, biphenyl, and naphthyl,
an acyl group,
an acyloxy group,
an aminocarbonyloxymethyl group,
a thiocarbonyl group, and
a thio group, a prodrug compound thereof, a pharmaceutically acceptable salt, hydrate, or solvate thereof.

(3) A CETP activity inhibitor comprising as an active ingredient the compound as described in the above (2), which is represented by the formula (I-1):

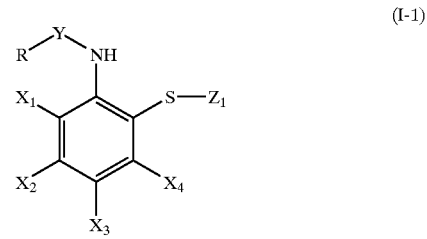

(I-1)

wherein R, X$_1$, X$_2$, X$_3$, X$_4$, and Y are the same as in the above (2) and Z$_1$ represents
a hydrogen atom;
a group represented by the formula

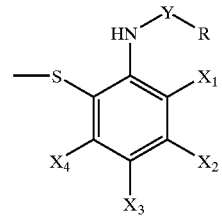

wherein R, X$_1$, X$_2$, X$_3$, X$_4$, and Y are the same as described above;
—Y$_1$R$_1$,
wherein Y$_1$ represents —CO—; or
—CS—, and
R$_1$ represents
a substituted or unsubstituted straight chain or branched C$_{1-10}$ alkyl group;
a C$_{1-4}$ lower alkoxy group;
a C$_{1-4}$ lower alkylthio group;
a substituted or unsubstituted amino group;
a substituted or unsubstituted ureido group;
a substituted or unsubstituted C$_{3-10}$ cycloalkyl group;
a substituted or unsubstituted C$_{3-10}$ cycloalkyl C$_{1-10}$ alkyl group;
a substituted or unsubstituted aryl group;
a substituted or unsubstituted aralkyl group;
a substituted or unsubstituted arylalkenyl group;
a substituted or unsubstituted arylthio group;
a substituted or unsubstituted 5- or 6-membered heterocyclic group having 1–3 nitrogen, oxygen, or sulfur atoms; or
a substituted or unsubstituted 5- or 6-membered heteroarylalkyl group; or
—S—R$_2$,
wherein R$_2$ represents
a substituted or unsubstituted C$_{1-4}$ lower alkyl group; or
a substituted or unsubstituted aryl group,
a prodrug compound, a pharmaceutically acceptable salt, hydrate, or solvate thereof.

(4) A CETP activity inhibitor comprising as an active ingredient the compound as described in the above (3), wherein $R_1$ represents
 a straight chain or branched $C_{1-10}$ alkyl group which may have 1–3 substituents selected from the group consisting of
  a halogen atom selected from fluorine, chlorine, and bromine,
  a $C_{1-4}$ lower alkoxy group,
  an amino group that may be substituted with a $C_{1-4}$ lower alkyl, acyl, or hydroxyl group,
  a $C_{1-4}$ lower alkylthio group,
  a carbamoyl group,
  a hydroxyl group,
  an acyl group,
  an acyloxy group having an acyl group,
  a carboxyl group, and
  an aryloxy group that may be substituted with a halogen atom selected from fluorine, chlorine, and bromine;
  a $C_{1-4}$ lower alkoxy group;
  a $C_{1-4}$ lower alkylthio group;
  an amino or ureido group that may have 1–2 substituents selected from the group consisting of
   a $C_{1-4}$ lower alkyl group,
   a hydroxyl group,
   an acyl group, and
   an aryl group that may be substituted with a lower $C_{1-4}$ alkoxy group;
 a $C_{3-10}$ cycloalkyl or $C_{3-10}$ cycloalkyl $C_{1-10}$ alkyl group that may have substituents selected from the group consisting of
  a straight or branched $C_{1-10}$ alkyl group,
  a $C_{3-10}$ cycloalkyl group,
  a $C_{5-8}$ cycloalkenyl group,
  an aryl group,
  an amino group,
  a $C_{1-4}$ lower alkylamino group having a $C_{1-4}$ lower alkyl group, and
  an acylamino group having an acyl group;
 an aryl group, an aralkyl group, an arylalkenyl group, or an arylthio group, each of which may have 1–4 substituents selected from the group consisting of
  a $C_{1-10}$ alkyl group,
  a halogen atom selected from fluorine, chlorine, and bromine,
  a nitro group,
  a hydroxyl group,
  a $C_{1-4}$ lower alkoxy group,
  a $C_{1-4}$ lower alkylthio group,
  an acyl group,
  a halo- $C_{1-4}$ lower alkyl group having a halogen atom selected from fluorine, chlorine, and bromine, and
  an amino group that may be substituted with a $C_{1-4}$ lower alkyl or acyl group;
 a 5- or 6-membered heterocyclic group having 1–3 nitrogen, oxygen or sulfur atoms or a 5- or 6-membered heteroarylalkyl group that may have 1–4 substituents selected from the group consisting of
  a straight chain or branched $C_{1-10}$ alkyl group,
  a halogen atom selected from fluorine, chlorine, and bromine,
  an acyl group,
  an oxo group, and
  an halo-$C_{1-4}$ lower alkyl group having a halogen atom selected from fluorine, chlorine, and bromine; and $R_2$ represents
 a $C_{1-4}$ lower alkyl group that may have 1–3 substituents selected from the group consisting of
  a $C_{1-4}$ lower alkoxy groups,
  an amino group that may be substituted with a $C_{1-4}$ lower alkyl or acyl group,
  a $C_{1-4}$ lower alkylthio group,
  a carbamoyl group,
  a hydroxyl group,
  a carboxyl group,
  an acyl group, and
  a 5- or 6-membered heterocyclic group having 1–3 nitrogen, oxygen, or sulfur atoms; or
 an aryl group that may have 1–4 substituents selected from the group consisting of
  a $C_{1-4}$ lower alkyl group,
  a halogen atom selected from fluorine, chlorine, and bromine,
  a nitro group,
  a hydroxyl group,
  a $C_{1-4}$ lower alkoxy group,
  a $C_{1-4}$ lower alkylthio group,
  an acyl group,
  an amino group that may be substituted with a $C_{1-4}$ lower alkyl or acyl group, and
  a halo-$C_{1-4}$ lower alkyl group having a halogen atom selected from fluorine, chlorine, and bromine,
a prodrug compound, a pharmaceutically acceptable salt, hydrate, or solvate thereof.

(5) A CETP activity inhibitor comprising as an active ingredient the compound as described in the above (1), which is selected from the group consisting of
 bis-[2-(pivaloylamino)phenyl] disulfide;
 bis-[2-(2-propylpentanoylamino)phenyl]disulfide;
 bis-[2-(1-methylcyclohexanecarbonylamino)phenyl] disulfide;
 bis-[2-(1-isopentylcyclopentanecarbonylamino)phenyl] disulfide;
 bis-[2-(1-isopentylcyclohexanecarbonylamino)phenyl] disulfide;
 N-(2-mercaptophenyl)-2,2-dimethylpropionamide;
 N-(2-mercaptophenyl)-1-isopentylcyclohexanecarboxamide;
 N-(2-mercaptophenyl)-1-methylcyclohexanecarboxamide;
 N-(2-mercaptophenyl)-1-isopentylcyclopentanecarboxamide;
 N-(2-mercaptophenyl)-1-isopropylcyclohexanecarboxamide;
 N-(4,5-dichloro-2-mercaptophenyl)-1-isopentylcyclohexanecarboxamide;
 N-(4,5-dichloro-2-mercaptophenyl)-1-isopentylcyclopentanecarboxamide;
 N-(2-mercapto-5-methylphenyl)-1-isopentylcyclohexanecarboxamide;
 N-(2-mercapto-4-methylphenyl)-1-isopentylcyclohexanecarboxamide;
 S-[2-(1-isopentylcyclohexanecarbonylamino)phenyl] thioacetate;
 S-[2-(1-methylcyclohexanecarbonylamino)phenyl] 2,2-dimethylthiopropionate;
 S-[2-(pivaloylamino)phenyl]phenylthioacetate;

S-[2-(1-isopentylcyclohexanecarbonylamino)phenyl] 2,2-dimethylthiopropionate;
S-[2-(1-isopentylcyclohexanecarbonylamino)phenyl] 2-acetylamino-3-phenylthiopropionate;
S-[2-(1-isopentylcyclohexanecarbonylamino)phenyl] 3-pyridinethiocarboxylate;
S-[2-(1-isopentylcyclohexanecarbonylamino)phenyl] chlorothioacetate;
S-[2-(1-isopentylcyclohexanecarbonylamino)phenyl] methoxythioacetate;
S-[2-(1-isopentylcyclohexanecarbonylamino)phenyl] thiopropionate;
S-[2-(1-isopentylcyclohexanecarbonylamino)phenyl] phenoxy-thioacetate;
S-[2-(1-isopentylcyclohexanecarbonylamino)phenyl] 2-methylthiopropionate;
S-[2-(1-isopentylcyclohexanecarbonylamino)phenyl] 4-chlorophenoxythioacetate;
S-[2-(1-isopentylcyclohexanecarbonylamino)phenyl] cyclopropanethiocarboxylate;
S-[2-(1-isopentylcyclohexanecarbonylamino)phenyl] 2-acetylamino-4-carbamoylthiobutyrate;
S-[2-(1-isopentylcyclohexanecarbonylamino)phenyl] 2-hydroxy-2-methylthiopropionate;
S-[2-(1-isopentylcyclopentanecarbonylamino)phenyl] 2,2-dimethylthiopropionate;
S-[2-(1-isopentylcyclopentanecarbonylamino)phenyl] thioacetate;
S-[4,5-dichloro-2-(1-isopentylcyclohexanecarbonylamino)-phenyl] 2,2-dimethylthiopropionate;
S-[4,5-dichloro-2-(1-isopentylcyclopentanecarbonylamino)-phenyl] 2,2-dimethylthiopropionate;
S-[2-(1-isopentylcyclohexanecarbonylamino)-4-trifluoromethylphenyl] 2,2-dimethylthiopropionate;
O-methyl S-[2-(1-isopentylcyclohexanecarbonylamino) phenyl monothiocarbonate;
S-[2-(1-methylcyclohexanecarbonylamino)phenyl] S-phenyl dithiocarbonate;
S-[2-(1-isopentylcyclohexanecarbonylamino)phenyl] N-phenylthiocarbamate;
S-[2-(pivaloylamino)-4-trifluoromethylphenyl] 2,2-dimethylthiopropionate;
S-[4,5-dichloro-2-(1-cyclopropylcyclohexanecarbonylamino) phenyl] 2,2-dimethylthiopropionate;
S-[4,5-dichloro-2-(2-cyclohexylpropionylamino)phenyl] 2,2-dimethylthiopropionate;
S-[4,5-dichloro-2-(1-pentylcyclohexanecarbonylamino)-phenyl] 2,2-dimethylthiopropionate;
S-[4,5-dichloro-2-(1-cyclopropylmethylcyclohexane carbonylamino)phenyl] 2,2-dimethylthiopropionate;
S-[4,5-dichloro-2-(1-cyclohexylmethylcyclohexanecarbonylamino)phenyl] 2,2-dimethylthiopropionate;
S-[4,5-dichloro-2-(1-isopropylcyclohexanecarbonylamino)-phenyl] 2,2-dimethylthiopropionate;
S-[4,5-dichloro-2-(1-isopentylcycloheptanecarbonylamino)-phenyl] 2,2-dimethylthiopropionate;
S-[4,5-dichloro-2-(1-isopentylcyclobutanecarbonylamino)-phenyl] 2,2-dimethylthiopropionate;
S-[2-(1-isopentylcyclohexanecarbonylamino)-4-nitrophenyl] 2,2-dimethylthiopropionate;
S-[4-cyano-2-(1-isopentylcyclohexanecarbonylamino) phenyl] 2,2-dimethylthiopropionate;
S-[4-chloro-2-(1-isopentylcyclohexanecarbonylamino) phenyl] 2,2-dimethylthiopropionate;
S-[5-chloro-2-(1-isopentylcyclohexanecarbonylamino) phenyl] 2,2-dimethylthiopropionate;
S-[4-fluoro-2-(1-isopentylcyclohexanecarbonylamino) phenyl] 2,2-dimethylthiopropionate;
S-[4,5-difluoro-2-(1-isopentylcyclohexanecarbonylamino)-phenyl] 2,2-dimethylthiopropionate;
S-[5-fluoro-2-(1-isopentylcyclohexanecarbonylamino) phenyl] 2,2-dimethylthiopropionate;
bis-[4,5-dichloro-2-(1-isopentylcyclohexanecarbonylamino)-phenyl] disulfide;
2-tetrahydrofurylmethyl 2-(1-isopentylcyclohexanecarbonyl amino)phenyl disulfide;
N-(2-mercaptophenyl)-1-ethylcyclohexanecarboxamide;
N-(2-mercaptophenyl)-1-propylcyclohexanecarboxamide;
N-(2-mercaptophenyl)-1-butylcyclohexanecarboxamide;
N-(2-mercaptophenyl)-1-isobutylcyclohexanecarboxamide;
S-[2-(1-isopentylcyclohexanecarbonylamino)phenyl] cyclohexanethiocarboxylate;
S-[2-(1-isopentylcyclohexanecarbonylamino)phenyl] thiobenzoate;
S-[2-(1-isopentylcyclohexanecarbonylamino)phenyl] 5-carboxythiopentanoate;
S-[2-(1-isopentylcyclohexanecarbonylamino)-4-methylphenyl] thioacetate;
bis-[2-[1-(2-ethylbutyl)cyclohexanecarbonylamino] phenyl] disulfide;
N-(2-mercaptophenyl)-1-(2-ethylbutyl) cyclohexanecarboxamide;
S-[2-[1-(2-ethylbutyl)cyclohexanecarbonylamino] phenyl] 2-methylthiopropionate;
S-[2-(1-isobutylcyclohexanecarbonylamino)phenyl] 2-methylthiopropionate;
S-[2-[1-(2-ethylbutyl)cyclohexanecarbonylamino] phenyl] 1-acetylpiperidine-4-thiocarboxylate;
S-[2-[1-(2-ethylbutyl)cyclohexanecarbonylamino] phenyl] thioacetate;
S-[2-[1-(2-ethylbutyl)cyclohexanecarbonylamino]phenyl] 2,2-dimethylthiopropionate;
S-[2-[1-(2-ethylbutyl)cyclohexanecarbonylamino] phenyl] methoxythioacetate;
S-[2-[1-(2-ethylbutyl)cyclohexanecarbonylamino] phenyl] 2-hydroxy-2-methylthiopropionate;
S-[2-[1-(2-ethylbutyl)cyclohexanecarbonylamino] phenyl] 4-chlorophenoxythioacetate;
S-[2-(1-isobutylcyclohexanecarbonylamino)phenyl] 4-chlorophenoxythioacetate; and
S-[2-(1-isobutylcyclohexanecarbonylamino)phenyl]-1-acetyl-piperidine-4-thiocarboxylate,
a prodrug compound, a pharmaceutically acceptable salt, hydrate, or solvate thereof.

(6) A prophylactic or therapeutic agent for hyperlipidemia comprising as an active ingredient the compound as described in the above in (1)–(5), a prodrug compound, a pharmaceutically acceptable salt, hydrate, or solvate thereof.

(7) A prophylactic or therapeutic agent for atherosclerosis comprising as an active ingredient the compound as described in the above in (1)–(5), a prodrug compound, a pharmaceutically acceptable salt, or hydrate or solvate thereof.

(8) A Compound represented by the formula (I-2):

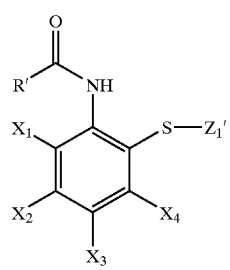

(I-2)

wherein R' represents
a substituted or unsubstituted $C_{3-10}$ cycloalkyl group or
a substituted or unsubstituted $C_{5-8}$ cycloalkenyl group;
$X_1$, $X_2$, $X_3$, and $X_4$ are as in the above (1); and
$Z_1'$ represents
a hydrogen atom;
a group represented by the formula:

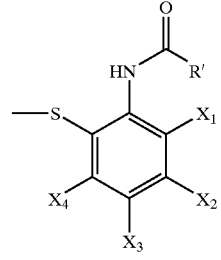

wherein R', $X_1$, $X_2$, $X_3$, and $X_4$ are as described above;
—$Y_1R_1$,
wherein $Y_1$ and $R_1$ are the same as in the above (3) or
—S—$R_2$,
wherein $R_2$ is the same as in the above (3),
a prodrug compound, a pharmaceutically acceptable salt, hydrate, or solvate thereof.

(9) A compound as described above in (8), which is represented by the formula (I-3):

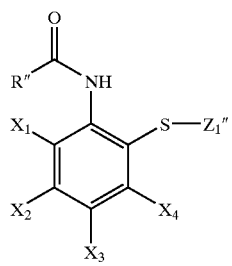

(I-3)

wherein R" represents
a 1-substituted-$C_{3-10}$ cycloalkyl group or
a 1-substituted-$C_{5-8}$ cycloalkenyl group;
$X_1$, $X_2$, $X_3$, and $X_4$ are the same as in the above (1); and
$Z_1"$ represents
a hydrogen atoms;
a group represented by the formula:

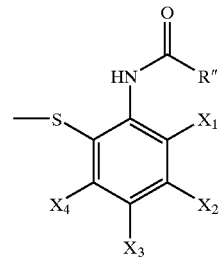

wherein R", $X_1$, $X_2$, $X_3$, and X, are as described above;
—$Y_1R_1$,
wherein $Y_1$ and $R_1$ are the same as in the above (3); or
—S—$R_2$,
wherein $R_2$ is the same as in the above (3),
a prodrug compound, a pharmaceutically acceptable salt, hydrate, or solvate thereof.

(10) A compound as described in the above (8), which is represented by the formula (II):

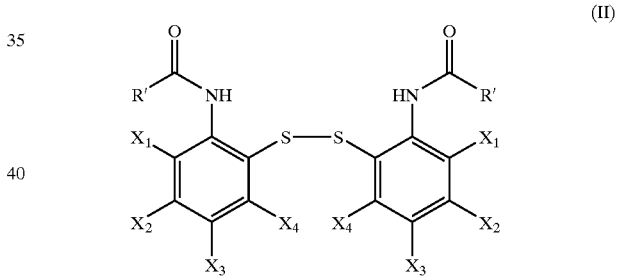

(II)

wherein R', $X_1$, $X_2$, $X_3$, and $X_4$ are the same as in the above (8), a prodrug compound, a pharmaceutically acceptable salt, hydrate, or solvate thereof.

(11) A compound as described in the above (9), which is represented by formula (II-1):

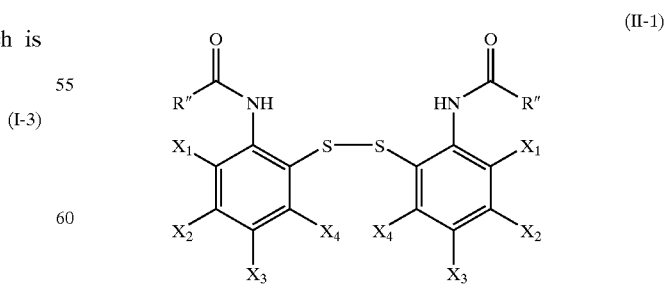

(II-1)

wherein R", $X_1$, $X_2$, $X_3$, and $X_4$ are the same as in the above (9), a prodrug compound, a pharmaceutically acceptable salt, hydrate, or solvate thereof.

(12) A compound as described in the above (8), which represented by the formula (III):

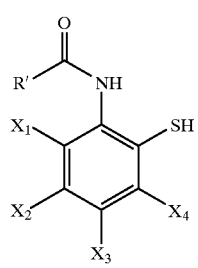

(III)

wherein R', $X_1$, $X_2$, $X_3$, and $X_4$ are the same as in the above (8), a prodrug compound, a pharmaceutically acceptable salt, hydrate, or solvate thereof.

(13) A compound as described in the above (9), which is represented by formula (III-1):

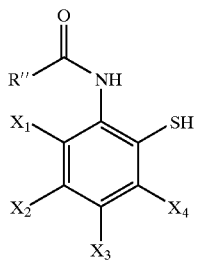

(III-1)

wherein R", $X_1$, $X_2$, $X_3$, and $X_4$ are the same as in the above (9), a prodrug compound, a pharmaceutically acceptable salt, hydrate, or solvate thereof.

(14) A compound as described in the above (8), which is represented by formula (IV):

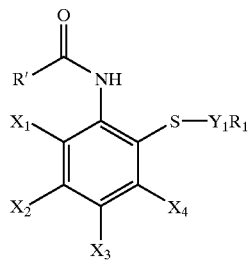

(IV)

wherein R', $X_1$, $X_2$, $X_3$, $X_4$, $Y_1$ and $R_1$ are the same as in the above (8), a prodrug compound, a pharmaceutically acceptable salt, hydrate, or solvate thereof.

(15) A compound as described in the above (9), which is represented by formula (IV-1):

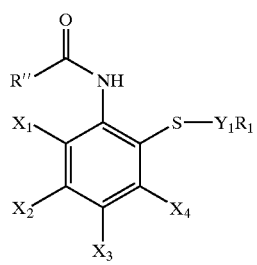

(IV-1)

wherein R", $X_1$, $X_2$, $X_3$, $X_4$, $Y_1$, and $R_1$ are the same as in the above (9), a prodrug compound, a pharmaceutically acceptable salt, hydrate, or solvate thereof.

(16) A compound as described in the above (8), which is represented by formula (V):

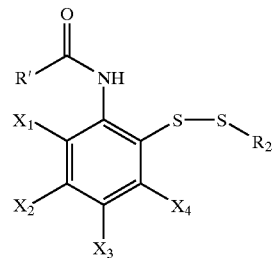

(V)

wherein R', $X_1$, $X_2$, $X_3$, $X_4$, and $R_2$ are the same as in the above (8), a prodrug compound, a pharmaceutically acceptable salt, hydrate, or solvate thereof.

(17) A compound as described in the above (9), which is represented by formula (V-1):

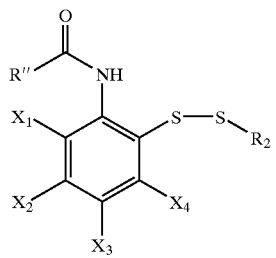

(V-1)

wherein R", $X_1$I $X_2$, $X_3$, $X_4$, and $R_2$ are the same as in the above (9), a prodrug compound, a pharmaceutically acceptable salt, hydrate, or solvate thereof.

(18) A compound as described in the above (8), which is selected from the group consisting of
bis-[2-(1-methylcyclohexanecarbonylamino)phenyl] disulfide;
bis-[2-(1-isopentylcyclopentanecarbonylamino)phenyl] disulfide;
bis-[2-(1-isopentylcyclohexanecarbonylamino)phenyl] disulfide;
N-(2-mercaptophenyl)-1-isopentylcyclohexanecarboxamide;
N-(2-mercaptophenyl)-1-methylcyclohexanecarboxamide;

N-(2-mercaptophenyl)-1-isopentylcyclopentanecarboxamide;
N-(2-mercaptophenyl)-1-isopropylcyclohexanecarboxamide;
N-(4,5-dichloro-2-mercaptophenyl)-1-isopentylcyclohexanecarboxamide;
N-(4,5-dichloro-2-mercaptophenyl)-1-isopentylcyclopentanecarboxamide;
N-(2-mercapto-5-methylphenyl)-1-isopentylcyclohexanecarboxamide;
N-(2-mercapto-4-methylphenyl)-1-isopentylcyclohexanecarboxamide;
S-[2-(1-isopentylcyclohexanecarbonylamino)phenyl] thioacetate;
S-[2-(1-methylcyclohexanecarbonylamino)phenyl] 2,2-dimethylthiopropionate;
S-[2-(1-isopentylcyclohexanecarbonylamino)phenyl] 2,2-dimethylthiopropionate;
S-[2-(1-isopentylcyclohexanecarbonylamino)phenyl] 2-acetylamino-3-phenylthiopropionate;
S-[2-(1-isopentylcyclohexanecarbonylamino)phenyl] 3-pyridinethiocarboxylate;
S-[2-(1-isopentylcyclohexanecarbonylamino)phenyl] chlorothioacetate;
S-[2-(1-isopentylcyclohexanecarbonylamino)phenyl] methoxythioacetate;
S-[2-(1-isopentylcyclohexanecarbonylamino)phenyl] thiopropionate;
S-[2-(1-isopentylcyclohexanecarbonylamino)phenyl] phenoxythioacetate;
S-[2-(1-isopentylcyclohexanecarbonylamino)phenyl] 2-methylthiopropionate;
S-[2-(1-isopentylcyclohexanecarbonylamino)phenyl] 4-chlorophenoxythioacetate;
S-[2-(1-isopentylcyclohexanecarbonylamino)phenyl] cyclopropanethiocarboxylate;
S-[2-(1-isopentylcyclohexanecarbonylamino)phenyl] 2-acetylamino-4-carbamoylthiobutyrate;
S-[2-(1-isopentylcyclohexanecarbonylamino)phenyl] 2-hydroxy-2-methylthiopropionate;
S-[2-(1-isopentylcyclopentanecarbonylamino)phenyl] 2,2-dimethylpropionate;
S-[2-(1-isopentylcyclopentanecarbonylamino)phenyl] thioacetate;
S-[4,5-dichloro-2-(1-isopentylcyclohexanecarbonylamino)-phenyl] 2,2-dimethylthiopropionate;
S-[4,5-dichloro-2-(1-isopentylcyclopentanecarbonylamino)-phenyl] 2,2-dimethylthiopropionate;
S-[2-(1-isopentylcyclohexanecarbonylamino)-4-trifluoromethylphenyl] 2,2-dimethylthiopropionate;
O-methyl S-[2-(1-isopentylcyclohexanecarbonylamino)phenyl] monothiocarbonate;
S-[2-(1-methylcyclohexanecarbonylamino)phenyl] S-phenyl dithiocarbonate;
S-[2-(1-isopentylcyclohexanecarbonylamino)phenyl] N-phenylthiocarbamate;
S-[4,5-dichloro-2-(1-cyclopropylcyclohexanecarbonylamino)-phenyl] 2,2-dimethylthiopropionate;
S-[4,5-dichloro-2-(1-pentylcyclohexanecarbonylamino)-phenyl] 2,2-dimethylthiopropionate;
S-[4,5-dichloro-2-(1-cyclopropylmethylcyclohexanecarbonylamino)phenyl] 2,2-dimethylthiopropionate;
S-[4,5-dichloro-2-(1-cyclohexylmethylcyclohexanecarbonylamino)phenyl] 2,2-dimethylthiopropioate;
S-[4,5-dichloro-2-(1-isopropylcyclohexanecarbonylamino)-phenyl] 2,2-dimethylthiopropionate;
S-[4,5-dichloro-2-(1-isopentylcycloheptanecarbonylamino)-phenyl] 2,2-dimethylthiopropionate;
S-[4,5-dichloro-2-(1-isopentylcyclobutanecarbonylamino)-phenyl] 2,2-dimethylthiopropionate;
S-[2-(1-isopentylcyclohexanecarbonylamino)-4-nitrophenyl] 2,2-dimethylthiopropionate;
S-[4-cyano-2-(1-isopentylcyclohexanecarbonylamino)phenyl] 2,2-dimethylthiopropionate;
S-[4-chloro-2-(1-isopentylcyclohexanecarbonylamino)phenyl] 2,2-dimethylthiopropionate;
S-[5-chloro-2-(1-isopentylcyclohexanecarbonylamino)phenyl] 2,2-dimethylthiopropionate;
S-[4-fluoro-2-(1-isopentylcyclohexanecarbonylamino)phenyl] 2,2-dimethylthiopropionate;
S-[4,5-difluoro-2-(1-isopentylcyclohexanecarbonylamino)-phenyl] 2,2-dimethylthiopropionate;
S-[5-fluoro-2-(1-isopentylcyclohexanecarbonylamino)-phenyl] 2,2-dimethylthiopropionate;
bis-[4,5-dichloro-2-(1-isopentylcyclohexanecarbonylamino)-phenyl] disulfide;
2-tetrahydrofurylmethyl 2-(1-isopentylcyclohexanecarbonyl-amino)phenyl disulfide;
N-(2-mercaptophenyl)-1-ethylcyclohexanecarboxamide;
N-(2-mercaptophenyl)-propylcyclohexanecarboxamide;
N-(2-mercaptophenyl)-1-butylcyclohexanecarboxamide;
N-(2-mercaptophenyl)-1-isobutylcyclohexanecarboxamide;
S-[2-(1-isopentylcyclohexanecarbonylamino)phenyl] cyclohexanethiocarboxylate;
S-[2-(1-isopentylcyclohexanecarbonylamino)phenyl] thiobenzoate;
S-[2-(1-isopentylcyclohexanecarbonylamino)phenyl] 5-carboxythiopentanoate;
S-[2-(1-isopentylcyclohexanecarbonylamino)-4-methylphenyl] thioacetate;
bis-[2-[1-(2-ethylbutyl)cyclohexanecarbonylamino]phenyl]-disulfide;
N-(2-mercaptophenyl)-1-(2-ethylbutyl)cyclohexanecarboxamide;
S-[2-[1-(2-ethylbutyl)cyclohexanecarbonylamino]phenyl] 2-methylthiopropionate;
S-[2-[1-isobutylcyclohexanecarbonylamino]phenyl] 2-methylthiopropionate;
S-[2-[1-(2-ethylbutyl)cyclohexanecarbonylamino]phenyl] 1-acetylpiperidine-4-thiocarboxylate;
S-[2-[1-(2-ethylbutyl)cyclohexanecarbonylamino]phenyl] thioacetate;
S-[2-[1-(2-ethylbutyl)cyclohexanecarbonylamino]phenyl] 2,2-dimethylthiopropionate;

S-[2-[1-(2-ethylbutyl)cyclohexanecarbonylamino]
phenyl] methoxythioacetate;

S-[2-[1-(2-ethylbutyl)cyclohexanecarbonylamino]
phenyl] 2-hydroxy-2-methylpropionate;

S-(2-[1-[2-ethylbutyl)cyclohexanecarbonylamino]
phenyl] 4-chlorophenoxythioacetate;

S-[2-(1-isobutylcyclohexanecarbonylamino)phenyl]
4-chlorophenoxythioacetate; and S-[2-(1-isobutylcyclohexanecarbonylamino)phenyl]
1-acetylpiperidine-4-thiocarboxylate, a prodrug compound, a pharmaceutically acceptable salt, hydrate, or solvate thereof.

(19) A phamaceutical composition comprising as an active ingredient the compound as described in the above (8)–(18), a prodrug compound, a pharmaceutically acceptable salt, hydrate, or solvate thereof.

(20) Use of the compound represented by the above formula (I), a prodrug compound, a pharmaceutically acceptable salt, hydrate, or solvate thereof, for production of a CETP activity inhibitor.

(21) Use of the compound represented by the above formula (I), a prodrug compound, a pharmaceutically acceptable salt, hydrate, or solvate thereof, for production of a prophylactic or therapeutic agent for hyperlipidemia.

(22) Use of the compound represented by the above formula (I), a prodrug compound, a pharmaceutically acceptable salt, hydrate, or solvate thereof, for production of a prophylactic or therapeutic agent for atherosclerosis.

(23) A method for inhibition of CETP activity comprising administering to patients the compound represented by the above formula (I), a prodrug compound, a pharmaceutically acceptable salt, hydrate, or solvate thereof.

(24) A method for prevention or therapy of hyperlipidemia comprising administering to patients the compound represented by the above formula (I), a prodrug compound, a pharmaceutically acceptable salt, hydrate, or solvate thereof.

(25) A method for prevention or therapy of atherosclerosis comprising administering to patients the compound represented by the above formula (I), a prodrug compound, a pharmaceutically acceptable salt, or hydrate, or solvate thereof.

The term "straight chain or branched $C_{11}$, alkyl group" used herein means an alkyl group having 1–10 carbon atoms which may be straight or branched. Specific examples thereof include methyl, ethyl, propyl, isopropyl, butyl, isobutyl, sec-butyl, tert-butyl, pentyl, isopentyl, neopentyl, tert-pentyl, 1-ethylbutyl, 2-ethylbutyl, 1-propylbutyl, 1,1-dimethylbutyl, 1-isobutyl-3-methylbutyl, 1-ethylpentyl, 1-propylpentyl, 1-isobutylpentyl, 2-ethylpentyl, 2-isopropylpentyl, 2-tert-butylpentyl, 3-ethylpentyl, 3-isopropylpentyl, 4-methylpentyl, 1,4-dimethylpentyl, 2,4-dimethylpentyl, 1-ethyl-4-methylpentyl, hexyl, 1-ethylhexyl, 1-propylhexyl, 2-ethylhexyl, 2-isopropylhexyl, 2-tert-butylhexyl, 3-ethylhexyl, 3-isopropylhexyl, 3-tert-butylhexyl, 4-ethylhexyl, 5-methylhexyl, heptyl, 1-ethylheptyl, 1-isopropylheptyl, 2-ethylheptyl, 2-isopropylheptyl, 3-propylheptyl, 4-propylheptyl, 5-ethylheptyl, 6-methylheptyl, octyl, 1-ethyloctyl, 2-ethyloctyl, nonyl, 1-methylnonyl, 2-methylnonyl, decyl, and the like groups. A straight chain or branched alkyl group having 1–8 carbon atoms is preferred.

The term "$C_{1-4}$ lower alkyl group" used herein means an alkyl group having 1–4 carbon atoms, and specifically includes methyl, ethyl, propyl, isopropyl, butyl, isobutyl, sec-butyl, tert-butyl, and the like groups.

The term "straight chain or branched $C_{2-10}$ alkenyl group" means an alkenyl group having 2–10 carbon atoms with at least one or more double bonds, which may be straight or branched. Specific examples thereof include allyl, vinyl, isopropenyl, 1-propenyl, 1-methyl-2-propenyl, 2-methyl-2-propenyl, 1-methyl-1-butenyl, crotyl, 1-methyl-3-butenyl, 3-methyl-2-butenyl, 1,3-dimethyl-2-butenyl, 1-pentenyl, 1-methyl-2-pentenyl, 1-ethyl-3-pentenyl, 4-pentenyl, 1,3-pentadienyl, 2,4-pentadienyl, 1-hexenyl, 1-methyl-2-hexenyl, 3-hexenyl, 4-hexenyl, 1-butyl-5-hexenyl, 1,3-hexadienyl, 2,4-hexadienyl, 1-heptenyl, 2-heptenyl, 3-heptenyl, 4-heptenyl, 5-heptenyl, 6-heptenyl, 1,3-heptadienyl, 2,4-heptadienyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 9-decenyl, and the like groups. An alkenyl group having 2–8 carbon atoms, which may be straight or branched, is preferred.

The term "halogen atom" means fluorine, chlorine, and bromine atoms.

The term "halo-$C_{1-4}$ alkyl group" means the above-described $C_{1-4}$ lower alkyl group substituted with 1–3 halogens, which may be the same or different. Specific examples thereof include fluoromethyl, chloromethyl, bromomethyl, difluoromethyl, dichloromethyl, trifluoromethyl, trichloromethyl, chloroethyl, difluoroethyl, trifluoroethyl, pentachloroethyl, bromopropyl, dichloropropyl, trifluorobutyl, and the like groups. Trifluoromethyl and chloroethyl are preferred.

The term "$C_{1-4}$ lower alkoxy group" means the alkoxy group containing the $C_{1-4}$ lower alkyl group as described above. Examples thereof include methoxy, ethoxy, propoxy, isopropoxy, butoxy, isobutoxy, sec-butoxy, tert-butoxy, and the like groups.

The term "$C_{1-4}$ lower alkylthio group" means the alkylthio group containing the $C_{1-4}$ lower alkyl group as described above. Examples thereof include methylthio, ethylthio, propylthio, isopropylthio, butylthio, isobutylthio, sec-butylthio, tert-butylthio, and the like groups.

The term "$C_{3-10}$ cycloalkyl group" means a cycloalkyl group having 3–10 carbon atoms, which may be monocyclic or polycyclic. Examples thereof include cyclopropyl, cyclobutyl, cyclopentyl, cyclohexyl, cycloheptyl, cyclooctyl, octahydroindenyl, decahydronaphthyl, bicyclo[2.2.1]heptyl, adamantyl, and the like groups. Preferred are those having 5–7 carbon atoms, including cyclopentyl, cyclohexyl, and cycloheptyl.

The term "$C_{5-8}$ cycloalkenyl group" means a cycloalkenyl group having 5–8 carbon atoms with one or more double bonds on the ring. Examples thereof include cyclopentenyl, cyclohexenyl, cycloheptenyl, cyclooctenyl, cyclopentadienyl, cyclohexadienyl, cycloheptadienyl, cyclooctadienyl, and the like groups. Preferred are those with 5–7 carbon atoms, including cyclopentenyl, cyclohexenyl, and cycloheptenyl.

The term "$C_{3-10}$ cycloalkyl $C_{1-10}$ alkyl group" means the above-described straight chain or branched $C_{1-10}$ alkyl group substituted with the above-described $C_{3-10}$ cycloalkyl group. Specific examples thereof include cyclopropylmethyl, cyclopentylmethyl, cyclohexylmethyl, cyclohexyl cyclopentylmethyl, dicyclohexylmethyl, 1-cyclopentylethyl, 1-cyclohexylethyl, 2-cyclopropylethyl, 2-cyclopentylethyl, 2-cyclohexylethyl, 2-cycloheptylethyl, 1-cyclohexyl-1-methylethyl, 1-cyclohexylpropyl, 2-cyclopentylpropyl, 3-cyclobutylpropyl, 3-cyclopentylpropyl, 3-cyclohexylpropyl, 3-cycloheptylpropyl, 1-cyclopropyl-1-methylpropyl, 1-cyclohexyl-2-methylpropyl, 1-cyclopentylbutyl, 1-cyclohexylbutyl, 3-cyclohexylbutyl, 4-cyclopropylbutyl, 4-cyclobutylbutyl, 4-cyclopentylbutyl, 1-cyclohexyl-1-methylbutyl, 1-cyclopentyl-2-ethylbutyl, 1-cyclohexyl-3-methylbutyl, 1-cyclopentylpentyl, 1-cyclohexylpentyl, 1-cyclohexylmethylpentyl, 2-cyclohexylpentyl, 2-cyclohexylmethylpentyl, 3-cyclopentylpentyl, 1-cyclohexyl-4-methylpentyl, 5-cyclopentylpentyl, 1-cyclopentylhexyl, 1-cyclohexylhexyl, 1-cyclopentylmethylhexyl, 2-cyclopentylhexyl, 2-cyclopropylethylhexyl, 3-cyclopentylhexyl, 1-cyclohexylheptyl, 1-cyclopentyl-1-methylheptyl, 1-cyclohexyl-1,6-dimethylheptyl, 1-cycloheptyloctyl, 2-cyclopentyloctyl, 3-cyclohexyloctyl, 2-cyclopentylmethyloctyl, 1-cyclopentylnonyl, 1-cyclohexylnonyl, 3-cyclopropylnonyl, 1-cyclopentyldecyl, 1-cyclohexylundecyl, 1-cyclopentyltridecyl, 2-cyclohexyltridecyl, and the like groups.

The "aryl group" includes phenyl, naphthyl, anthlryl, phenanthryl, biphenyl, and the like groups. Phenyl, naphthyl, and biphenyl groups are preferred.

The "aralkyl group" means the above-described $C_{1-4}$ lower alkyl group substituted with one or more aryl groups as described above. Examples thereof include benzyl, benzhydryl, trityl, phenethyl, 3-phenylpropyl, 2-phenylpropyl, 4-phenylbutyl, naphthylmethyl, 2-naphthylethyl, 4-biphenylmethyl, 3-(4-biphenyl) propyl, and the like groups.

The "arylalkenyl group" means an alkenyl group having 2–4 carbon atoms substituted with the above-described aryl group. Examples thereof include 2-phenylvinyl, 3-phenyl-2-propenyl, 3-phenyl-2-methyl-2-propenyl, 4-phenyl-3-butenyl, 2-(1-naphthyl)vinyl, 2-(2-naphthyl)vinyl, 2-(4-biphenyl)vinyl, and the like groups.

The "arylthio group" means an arylthio group containing the above-described aryl group and specifically include phenylthio, naphthylthio, and the like groups.

The "heterocyclic ring group" means 5- and 6-membered aromatic or non-aromatic heterocyclic ring groups containing at least one or more, specifically 1–4, preferably 1–3, hetero atoms selected from nitrogen, oxygen, and sulfur atoms. Specific examples thereof include aromatic heterocyclic rings such as thiatriazolyl, tetrazolyl, dithiazolyl, oxadiazolyl, thiadiazolyl, triazolyl, oxazolyl, pyrazolyl, pyrrolyl, furyl, thienyl, tetrazinyl, triazinyl, pyrazinyl, pyridazinyl, pyrimidinyl, pyridyl, or the like groups and non-aromatic heterocyclic rings such as dioxoranyl, pyrrolidinyl, tetrahydrofuryl, tetrahydrothienyl, dithiadiazinyl, thiadiazinyl, morpholino, morpholinyl, oxazinyl, thiazinyl, piperazinyl, piperidyl, piperidino, pyranyl, thiopyranyl, or the like groups. Preferable groups are aromatic heterocyclic (heteroaryl) groups including furyl, thienyl, pyrrolyl, pyridyl, and the like and non-aromatic heterocyclic groups containing at least one nitrogen atom, including pyrrolidinyl, tetrahydrofuryl, piperazinyl, piperidyl, piperidino, and the like groups.

The "heteroarylalkyl group" means the above-described $C_{1-4}$ lower alkyl group substituted with the above-described 5- or 6-membered aromatic heterocyclic (heteroaryl) group and specifically include 2-thienylmethyl, 2-furylmethyl, 2-pyridylmethyl, 3-pyridylmethyl, 2-thienyl-2-ethyl, 3-furyl-1-ethyl, 2-pyridyl-3-propyl, and the like groups.

The "acyl group" specifically includes formyl, acetyl, propionyl, butyryl, isobutyryl, valeryl, isovaleryl, pivaloyl, hexanoyl, acryloyl, propioloyl, metacryloyl, crotonoyl, benzoyl, naphthoyl, toluoyl, hydroatropoyl, atropoyl, cinnamoyl, furoyl, thenoyl, nicotinoyl, isonicotinoyl, glucoloyl, lactoyl, glyceroyl, tropoyl, benzyloyl, salicyloyl, anisoyl, vaniloyl, veratoroyl, piperoniroyl, protocatechoyl, galloyl, cyclopentanecarbonyl, cyclohexanecarbonyl, cycloheptanecarbonyl, 1-methyl cyclohexanecarbonyl, 1-isopentylcyclopentanecarbonyl, 1-isopentyl cyclohexanecarbonyl, tert-butoxycarbonyl, methoxycarbonyl, ethoxycarbonyl, 2-(1-isopentylcyclohexanecarbonylamino)phenylthiocarbonyl, and the like groups. Preferred are acetyl, tert-butoxycarbonyl, benzoyl, 1-methylcyclohexanecarbonyl, 1-isopentylcyclopentanecarbonyl, 1-isopentylcyclohexanecarbonyl, and 2-(1-isopentylcyclohexanecarbonylamino)phenylthiocarbonyl.

The term "substituted or unsubstituted" of the "substituted or unsubstituted $C_{3-10}$ cycloalkyl group", the "substituted or unsubstituted $C_{5-8}$ cycloalkenyl group", and the "substituted or unsubstituted $C_{3-10}$ cycloalkyl $C_{1-10}$ alkyl group" described for R, $R_1$, and the like means that the group may be substituted with 1–4 substituents which may be the same or different and any position may be arbitrarily substituted without any limitation. Specific examples of these groups are the above-described straight chain or branched $C_{1-10}$ alkyl group; the above-described straight chain or branched $C_{2-10}$ alkenyl group; the above-described $C_{3-10}$ cycloalkyl group; the above-described $C_{5-8}$ H cycloalkenyl group; the above-described $C_{3-10}$ cycloalkyl $C_{1-10}$ alkyl group; the above-described aryl group; an amino group; a $C_{1-4}$ lower alkylamino group such as methylamino, ethylamino, or the like groups; an acylamino group such as acetylamino, propionylamino, benzylamino, or the like groups; an oxo group; the above-described aralkyl group; the above-described arylalkenyl group, and the like.

The above substituents are recommended as substituents for R. Among these, preferred for $R_1$ are the above-described straight chain or branched $C_{1-10}$ alkyl group, the above-described $C_{3-10}$ cycloalkyl group, the above-described $C_{5-8}$ cycloalkenyl group, the above-described aryl group, and the above-described amino group.

The term "substituted or unsubstitueted" of the "substituted or unsubstitueted aryl group", the "5- or 6-membered heterocyclic group containing 1–3 nitrogen, oxygen, or sulfur atoms", the "substituted or unsubstitueted aralkyl group", the "substituted or unsubstitueted arylalkenyl group", the "substituted or unsubstitueted arylthio group", and the "substituted or unsubstitueted 5- or 6-membered heteroarylalkyl group" described with respect to R, $R_1$, and the like means that the groups may be substituted with 1–4, preferably 1–3, substituents which may be the same or different and any position may be arbitrarily substituted without particular restriction. Examples of these groups include the above-described straight chain or branched $C_{1-10}$ alkyl group, preferably a straight chain or branched $C_{1-6}$ aralkyl group; the above-described straight chain or branched $C_{2-10}$alkenyl group, preferably a straight chain or branched $C_{2-6}$ alkenyl group; the above-described halogen atom; a nitro group; the above-described amino group that may be substituted with the above-described $C_{1-4}$ lower alkyl group or the above-described acyl group; a hydroxyl group; the above-described $C_{1-4}$ lower alkoxy group; the above-described $C_{1-4}$ lower alkylthio group; the above-described halo-$C_{1-4}$ lower alkyl group; the above-described acyl group; an oxo group, and the like.

The above substituents are recommended as substituents mainly for $R_1$. Among these, preferred for R the above-described straight chain or branched $C_{1-6}$ alkyl group, the above-described halogen atom, and a nitro group.

The "substituted or unsubstituted" of the "substituted or unsubstituted straight chain or branched $C_{1-10}$ alkyl group" described for R, and the like means that the group may be substituted with 1–3 substituents which may be the same or different and any position may be arbitrarily substituted without particular restriction. Examples of these groups are the above-described $C_{1-4}$ lower alkoxy group; the above-described $C_{1-4}$ lower alkyl group; the above-described amino group that may be substituted with an acyl or hydroxyl group; the above-described lower $C_{1-4}$ alkylthio group; a carbamoyl group; a hydroxyl group; the above-described halogen atom; the above-described acyloxy group containing an acyl group; a carboxyl group; the above-described acyl group; the above-described aryloxy group containing an aryl group that may be substituted; and the like.

The "substituted or unsubstituted" of the "$C_{1-4}$ lower alkyl group" described with respect to $R_2$ and the like means that the group may be substituted with 1–3 substituents which may be the same or different and any position may be arbitrarily substituted without particular restriction. Examples of the group include the above-described $C_{1-4}$ lower alkoxy group; the above-described amino group that may be substituted with the above-described $C_{1-4}$ lower alkyl group or the above-described acyl group; the above-described $C_{1-4}$ lower alkylthio group; a carbamoyl group; a hydroxyl group; a carboxyl group; the above-described acyl group; the above-described heterocyclic group (particularly aromatic heterocyclic groups such as thienyl or non-aromatic heterocyclic group such as tetrahydrofuryl); and the like.

The term "substituted or unsubstituted" of the "substituted or unsubstituted amino group" and the "substituted or unsubstituted ureido group" described with respect to R, means that the groups may be substituted with one or more, preferably 1–2, substituents which may be the same or different and any position may be arbitrarily substituted without particular restriction. Examples of these groups are the above-described $C_{1-4}$ lower alkyl group; a hydroxyl group; the above-described acyl group; the above-described aryl group which may be substituted with the above-described $C_{1-4}$ lower alkoxy group; and the like.

The "mercapto-protecting group" described with respect to z means commonly used mercapto protecting groups. Any organic residues that can be dissociated in vivo may be used without particular restriction. It may form a disulfide structure, that is dimer. Examples thereof include $C_{1-4}$ lower alkylthiomethyl;$C_{1-4}$ lower alkylthiomethyl; aralkyloxymethyl;aralkylthiomethyl; $C_{3-10}$ cycloalkyloxymethyl; C., cycloalkenyloxymethyl; $C_{3-10}$ cycloalkyl $C_{1-10}$ alkoxymethyl; aryloxymethyl; arylthiomethyl; acyl; acyloxy; aminocarbonyloxymethyl; thiocarbonyl; and thio groups. Specific examples thereof include a $C_{1-4}$ lower alkoxymethyl group with the above-described $C_{1-4}$ lower alkoxy group; a $C_{1-4}$ lower alkylthiomethyl group with the above-described $C_{1-4}$ lower alkylthio group; an aralkyloxymethyl group with the above-described aralkyl group; an aralkylthiomethyl group with the above-described aralkyl group; a $C_{3-10}$ cycloalkyloxymethyl group with the above-described $C_{3-10}$ cycloalkyl group; a $C_{1-8}$ cycloalkenyloxymethyl group with the above-described $C_{5-8}$ cycloalkenyl group; a $C_{3-10}$ cycloalkyl $C_{1-10}$alkoxymethyl group with the above-described $C_{3-10}$ cycloalkyl $C_{1-10}$ alkyl group; an aryloxymethyl group with the above-described aryl group; an arylthiomethyl group with the above-described arylthio group; an acyl group containing the above-described substituted or unsubstituted straight chain or branched $C_{1-10}$ alkyl group, the above-described halo-$C_{1-4}$ lower alkyl group, the above-described $C_{1-4}$ lower alkoxy group, the above-described $C_{1-4}$ lower alkylthio group, the above-described substituted or unsubstituted amino group, the above-described substituted or unsubstituted ureido group, the above-described substituted or unsubstituted $C_{3-10}$ cycloalkyl group, the above-described substituted or unsubstituted $C_{3-10}$ cycloalkyl $C_{1-10}$ alkyl group, the above-described substituted or unsubstituted aryl group, the above-described substituted or unsubstituted aralkyl group, the above-described substituted or unsubstituted arylalkenyl group, the above-described substituted or unsubstituted arylthio group, the above-described substituted or unsubstituted 5- or 6-membered heterocyclic group with 1–3 nitrogen, oxygen, or sulfur atoms, or the above-described substituted or unsubstituted 5- or 6-membered heteroarylalkyl group; an acyloxy group containing the above-described substituted or unsubstituted straight chain or branched $C_{1-10}$ alkyl group, the above-described halo-$C_{1-4}$ lower alkyl group, the above-described $C_{1-4}$ lower alkoxy group, the above-described $C_{1-4}$ lower alkylthio group, the above-described substituted or unsubstituted amino group, the above-described substituted or unsubstituted ureido group, the above-described substituted or unsubstituted $C_{3-10}$ cycloalkyl group, the above-described substituted or unsubstituted $C_{3-10}$ cycloalkyl $C_{1-10}$ alkyl group, the above-described substituted or unsubstituted aryl group, the above-described substituted or unsubstituted aralkyl group, the above-described substituted or unsubstituted arylalkenyl group, the above-described substituted or unsubstituted arylthio group, the above-described substituted or unsubstituted 5- or 6-membered heterocyclic group with 1–3 nitrogen, oxygen, or sulfur atoms, or the above-described substituted or unsubstituted 5- or 6-membered heteroarylalkyl group; an aminocarbonyloxymethyl group that may be substituted with the above-described substituted or unsubstituted straight chain or branched $C_{1-10}$ alkyl group, the above-described halo-$C_{1-4}$ alkyl group, the above-described $C_{1-4}$ lower alkoxy group, the above-described $C_{1-4}$ lower alkylthio group, the above-described substituted or unsubstituted $C_{3-10}$ cycloalkyl group, the above-described substituted or unsubstituted $C_{3-10}$ cycloalkyl $C_{1-10}$ alkyl group, the above-described substituted or unsubstituted aryl group, the above-described substituted or unsubstituted aralkyl group, the above-described substituted or unsubstituted arylalkenyl group, the above-described substituted or unsubstituted 5- or 6-membered heterocyclic group with 1–3 nitrogen, oxygen, or sulfur atoms, or the above-described substituted or unsubstituted 5- or 6-membered heteroarylalkyl group; a thiocarbonyl group containing the above-described substituted or unsubstituted straight chain or branched $C_{1-10}$ alkyl group, the above-described halo-$C_{1-4}$ lower alkyl group, the above-described $C_{1-4}$ lower alkoxy group, the above-described $C_{1-4}$ lower alkylthio group, the above-described substituted or unsubstituted amino group, the above-described substituted or unsubstituted ureido group, the above-described substituted or unsubstituted $C_{1-10}$ cycloalkyl group, the above-described substituted or unsubstituted $C_{3-10}$ cycloalkyl $C_{1-10}$ alkyl group, the above-described substituted or unsubstituted aryl group, the above-described substituted or unsubstituted aralkyl group, the above-described substituted or unsubstituted arylalkenyl group, the above-described substituted or unsubstituted arylthio group, the above-described substituted or unsubstituted 5- or 6-membered heterocyclic group with 1–3 nitrogen, oxygen, or sulfur atoms, or the above-described substituted or unsubstituted 5- or 6-membered heteroarylalkyl group; and a thio group containing the above-described substituted or unsubstituted $C_{1-4}$ lower alkyl or aryl group.

More specifically, preferred as the "straight chain or branched $C_{1-10}$ alkyl group" for R are methyl, ethyl, isopropyl, butyl, isobutyl, tert-butyl, heptyl, 1-propylbutyl, and 1-isobutyl-3-methylbutyl.

The "straight chain or branched $C_{2-10}$ alkenyl group" referred to as R are preferably allyl, vinyl, isopropenyl, 1-methyl-2-propenyl, 2-methyl-2-propenyl, 1-methyl-1-butenyl, crotyl, 1,3-dimethyl-2-butenyl, 1-pentenyl, and 1-methyl-2-pentenyl.

The "halo-$C_{1-4}$ lower alkyl group" for R means a $C_{1-4}$ lower alkyl group, particularly preferably a methyl group, substituted with the above-described halogen atom, particularly preferably fluorine and chlorine, with being a trifluoromethyl group preferred.

The "substituted or unsubstituted $C_{3-10}$ cycloalkyl group" for R means a $C_{3-10}$ cycloalkyl group (particularly preferably cyclopropyl, cyclobutyl, cyclopentyl, cyclohexyl, cycloheptyl, octahydroindenyl, decahydronaphthyl, adamantyl, and bicyclo[2.2.1]-heptyl) that may be substituted with 1–4 substituents selected from the above-described straight chain or branched $C_{1-10}$ alkyl group, (particularly preferably a $C_{2-8}$ alkyl group such as methyl, ethyl, propyl, isopropyl, butyl, isobutyl, tert-butyl, pentyl, isopentyl, 2,2-dimethylpropyl, 4-methylpentyl, 2-ethylbutyl, or the like), the above-described straight chain or branched $C_{2-10}$ alkenyl group (particularly preferably a $C_{2-8}$ alkenyl group such as 1-methylvinyl, 2-methylvinyl, 3-methyl-3-propenyl, or the like), the above-described $C_{3-10}$ cycloalkyl group (particularly preferably a $C_{3-7}$ cycloalkyl group such as cyclopropyl, cyclopentyl, cyclohexyl, or the like), the above-described $C_{5-8}$ cycloalkenyl group (particularly preferably a $C_{5-6}$ cycloalkenyl group such as cyclopentenyl, cyclohexenyl, or the like), the above-described $C_{3-10}$ cycloalkyl $C_{3-10}$ alkyl group (particularly preferably a $C_{3-7}$ cycloalkyl $C_{1-4}$ alkyl group such as cyclopropylmethyl, 2-cyclopropylethyl, 2-cyclopentylethyl, cyclohexylmethyl, 2-cyclohexylethyl, or the like), the above-described aryl group (particularly preferably a phenyl group), an oxo group, the above described aralkyl group (particularly preferably a phenyl $C_{1-4}$ lower alkyl group such as benzyl, phenethyl, or the like), and the above-described arylalkenyl group (particularly preferably a 2-phenylvinyl group). Preferable examples thereof include 2,2,3,3-tetramethylcyclopropyl, 1-isopentylcyclobutyl, 1-isopropylcyclopentyl, 1-isobutylcyclopentyl, 1-isopentylcyclopentyl, 1-cyclohexylmethylcyclopentyl, cyclohexyl, 1-methylcyclohexyl, 1-ethylcyclohexyl, 1-propylcyclohexyl, 1-isopropylcyclohexyl, 1-butylcyclohexyl, 1-isobutylcyclohexyl, 1-pentylcyclohexyl, 1-isopentylcyclohexyl, 1-(2,2-dimethylpropyl)-cyclohexyl, 1-(4-methylpentyl)cyclohexyl, 1-(2-ethylbutyl) cyclohexyl, 4-tert-butyl-1-isopentylcyclohexyl, 1-cyclopropylcyclohexyl, 1-bicyclohexyl, 1-phenylcyclohexyl, 1-cyclopropylmethylcyclohexyl, 1-cyclohexylmethylcyclohexyl, 1-(2-cyclopropylethyl)cyclohexyl, 1-(2-cyclopentylethyl)cyclohexyl, 1-(2-cyclohexylethyl)cyclohexyl, 4-methylcyclohexyl, 4-propylcyclohexyl, 4-isopropylcyclohexyl, 4-tert-butylcyclohexyl, 4-pentylcyclohexyl, 4-bicyclohexyl, 1-isopentylcycloheptyl, 3a-octahydroindenyl, 4a-decahydronaphthyl, 1-adamantyl, and 7,7-dimethyl-1-(2-oxo)-bicyclo[2.2.1]heptyl. The site of substitution is not specifically limited, but particularly preferably at position 1. Any substitution group as described above may be used, but the straight chain or branched $C_{1-10}$ alkyl group is particularly preferred.

The substituent for the "substituted or unsubstituted $C_{5-8}$ cycloalkenyl group" for R is the same as that for the above "substituted or unsubstituted $C_{3-10}$ cycloalkyl group". Specifically, it means a cycloalkenyl group (especially cyclopentenyl and cyclohexenyl) that may have 1–4 substituents selected from the above-described straight chain or branched $C_{1-10}$ alkyl group (particularly preferably a $C_{1-8}$ alkyl group such as methyl, ethyl, propyl, isopropyl, butyl, isobutyl, pentyl, isopentyl, 2,2-dimethylpropyl, 4-methylpentyl, or the like), the above-described straight chain or branched $C_{2-10}$ alkenyl group (particularly preferably a $C_{2-8}$ H alkenyl group such as 1-methylvinyl, 2-methylvinyl, 3-methyl-3-propenyl, and the like), the above-described $C_{3-10}$ cycloalkyl group (particularly preferably a $C_{3-7}$ cycloalkyl group such as cyclopropyl, cyclopentyl, cyclohexyl, or the like), the above-described $C_{5-8}$ cycloalkenyl group (particularly preferably a $C_{5-6}$ cycloalkenyl group like cyclopentenyl, cyclohexenyl, or the like), the above-described $C_{3-10}$ cycloalkyl $C_{1-10}$ alkyl group (particularly preferably a $C_{3-7}$ cycloalkyl $C_{1-4}$ lower alkyl group such as cyclopropyl methyl, 2-cyclopropylethyl, 2-cyclopentylethyl, cyclohexylmethyl, 2-cyclohexylethyl, or the like), the above-described aryl group (particularly preferably a phenyl group), an oxo group, the above-described aralkyl group (particularly preferably a phenyl $C_{1-4}$ lower alkyl group such as benzyl, phenethyl, or the like), and arylalkenyl group (particularly preferably 2-phenylvinyl). Preferable examples of the cycloalkenyl group includes 1-isopropyl-2-cyclopentenyl, 1-isopropyl-3-cyclopentenyl, 1-isobutyl-2-cyclopentenyl, 1-isobutyl-3-cyclopentenyl, 1-isopentyl-2-cyclopentenyl, 1-isopentyl-3-cyclopentenyl, 1-cyclohexylmethyl-2-cyclopentenyl, 1-cyclohexylmethyl-3-cyclopentenyl, 1-cyclohexenyl, 2-cyclohexenyl, 3-cyclohexenyl, 1-methyl-2-cyclohexenyl, 1-methyl-3-cyclohexenyl, 1-ethyl-2-cyclohexenyl, 1-ethyl-3-cyclohexenyl, 1-propyl-2-cyclohexenyl, 1-propyl-3-cyclohexenyl, 1-isopropyl-3-cyclohexenyl, 1-butyl-2-cyclohexenyl, 1-butyl-3-cyclohexenyl, 1-isobutyl-2-cyclohexenyl, 1-isobutyl-3-cyclohexenyl, 1-pentyl-2-cyclohexenyl, 1-pentyl-3-cyclohexenyl, 1-iso pentyl-2-cyclohexenyl, 1-iso pentyl-3- cyclohexenyl, 1-(2,2-dimethylpropyl)-2-cyclohexenyl, 1-(2,2-dimethylpropyl)-3-cyclohexenyl, 1-(4-methylpentyl)-2-cyclohexenyl, 1-(4-methylpentyl)-3-cyclohexenyl, 1-cyclopropyl-2-cyclohexenyl, 1-cyclopropyl-3-cyclohexenyl, 1-cyclohexyl-2-cyclohexenyl, 1-cyclohexyl-3-cyclohexenyl, 1-phenyl-2-cyclohexenyl, 1-phenyl-3-cyclohexenyl, 1-cyclopropylmethyl-2-cyclohexenyl, 1-cyclo propylmethyl-3-cyclohexenyl, 1-cyclohexylmethyl-2-cyclohexenyl, 1-cyclohexylmethyl-3-cyclohexenyl, 1-(2-cyclopropylethyl)-2-cyclohexenyl, 1-(2-cyclopropylethyl)-3-cyclohexenyl, 1-(2-cyclopentylethyl)-2-cyclohexenyl, 1-(2-cyclopentylethyl)-3-cyclohexenyl, 1-(2-cyclohexylethyl)-2-cyclohexenyl, and 1-(2-cyclohexylethyl)-3-cyclohexenyl. There is no special restriction on the substitution position, but the particularly preferred position is position 1. Any one of the above substituents may be used, but the straight chain or branched $C_{1-10}$ alkyl group or the $C_{3-10}$ cycloalkyl $C_{1-4}$ alkyl group is particularly preferred.

The "substituted or unsubstituted $C_{3-10}$ cycloalkyl $C_{1-10}$ alkyl group" for R means a $C_{3-10}$ cycloalkyl $C_{1-10}$ alkyl group (particularly preferably cyclohexylmethyl, 1-cyclohexylethyl, 1-cyclohexyl-1-methylethyl, 1-cyclohexyl-2-methylpropyl, 1-cyclohexyl-3-methylbutyl, 1-cyclohexylhexyl, 1-cyclohexyl-4-methylpentyl, and 1-cyclohexylheptyl) $C_{1-10}$ alkyl group of which is straight chain or branched and which may have 1–4 substituents selected from the above-described $C_{3-10}$ cycloalkyl group (particularly preferably a $C_{3-7}$ cycloalkyl group such as cyclopentyl or cyclohexyl), the above-described $C_{5-8}$ cycloalkenyl group (particularly preferably a C,-7 cycloalkenyl group such as cyclopentenyl or cyclohexenyl), and the above-described aryl group (particularly preferably a phenyl group). There is no special restriction on the substitution position. The above-described substituents may be placed at the straight chain or branched $C_{1-10}$ alkyl moiety. Preferable examples of the $C_{3-10}$ cycloalkyl $C_{1-10}$ alkyl group include cyclohexylmethyl, 1-cyclohexylethyl, cyclohexylcyclopentylmethyl, dicyclohexylmethyl, 1-cyclohexyl-1-methylethyl, 1-cyclohexyl-2-methylpropyl, 1-cyclohexyl-3-methylbutyl, 1-cyclohexyl-4-methylpentyl, 1-cyclohexylhexyl, and 1-cyclohexylheptyl.

The "substituted or unsubstituted aryl group" for R means an aryl group (particularly preferably a phenyl group) that may have 1–4 substituents selected from the above-described straight chain or branched $C_{1-6}$ alkyl group (particularly preferably a tert-butyl group), the above-described halogen atom (particularly preferably fluorine and chlorine), and a nitro group. Preferable examples of the aryl group are phenyl, 2-chlorophenyl, 4-nitrophenyl, and 3,5-di-tert-butylphenyl.

The "substituted or unsubstituted aralkyl" for R means an aralkyl group (particularly preferably benzyl, benzhydryl, and trityl) which may have substituents selected from the above-described halogen atom (particularly preferably fluorine and chlorine), a nitro group, and a hydroxy group, and in which the $C_{1-4}$ lower alkyl group is straight chain or branched. There is no special restriction on the position of substitution. The straight chain or branched $C_{1-4}$ lower alkyl moiety may be substituted. Preferable examples of the aralkyl group are benzyl and trityl.

The "substituted or unsubstituted 5- or 6-membered heterocyclic group having 1–3 nitrogen, oxygen or sulfur atoms" for R means the above-described heterocyclic group that may have 1–4 substituents selected from the above-described straight chain or branched $C_{1-6}$ alkyl group (particularly preferably a tert-butyl group), the above-described halogen atom (particularly preferably fluorine and chlorine), and a nitro group. The heterocyclic group is preferably an aromatic heterocyclic group, particularly preferably furyl, thienyl, and pyridyl.

The "substituted or unsubstituted straight chain or branched $C_{1-10}$ alkyl group" for R, means a straight chain or branched $C_{1-10}$ alkyl group that may have a substituent selected from the above-described halogen atom (particularly preferably fluorine and chlorine), the above-described $C_{1-4}$ lower alkoxy group (particularly preferably a methoxy group), an amino group that may be substituted with the above-described $C_{1-4}$ lower alkyl group (particularly preferably a methyl group), the above-described acyl group (particularly preferably an acetyl group), or a hydroxyl group, the above-described $C_{1-4}$ lower alkylthio group (particularly preferably a methylthio group), a carbamoyl group, a hydroxyl group, an acyloxy group having the above-described acyl group (particularly preferably an acetyloxy group), a carboxyl group, an acyl group (particularly preferably a methoxycarbonyl group), and an aryloxy group having the above-described substituted or unsubstituted aryl group (particularly preferably a phenoxy group and a 4-chlorophenoxy group). Preferable examples of the alkyl group include methyl, chloromethyl, ethyl, isopropyl, 1-methyl-2-pentyl, octyl, methoxymethyl, dimethylaminomethyl, acetylaminomethyl, 1-acetyl aminoethyl, 1-acetylamino-2-methylpropyl, 1-acetylamino-3-methylbutyl, 1-acetylamino-3-methylthiopropyl, 1-acetylamino-3-carbamoylpropyl, 1-hydroxy-1-methylethyl, 1-acetyloxy-1-methylethyl, 4-carboxybutyl, 2-methoxycarbonylethyl, phenoxymethyl, and 4-chlorophenoxymethyl.

The "$C_{1-4}$ lower alkoxy group" for $R_1$ is preferably a methoxy group and a tert-butoxy group.

The "$C_{1-4}$ lower alkylthio group" for $R_1$ is preferably a methylthio group.

The "substituted or unsubstituted amino group" for $R_1$ means an amino group that may have a substituent selected from the above-described $C_{1-4}$ lower alkyl group (particularly preferably ethyl, isopropyl, and tert-butyl), the above-described acyl group (particularly preferably acetyl and benzoyl), and the above-described aryl group (particularly preferably phenyl and 4-methoxyphenyl) that may be substituted with the above-described $C_{1-4}$ lower alkoxy group. Preferable examples of the amino group are ethylamino, isopropylamino, tert-butylamino, phenylamino, and 4-methoxyphenylamino.

The "substituted or unsubstituted ureido group" for $R_1$ means a ureido group that may have a substituent selected from the above-described $C_{1-4}$ lower alkyl group (particularly preferably methyl and ethyl), the above-described acyl group (particularly preferably acetyl and benzoyl), and the above-described aryl group (particularly preferably phenyl and 4-methoxyphenyl) that may be substituted with the above-described $C_{1-4}$ lower alkoxy group, with an N,N'-diphenylureido group being preferred.

The "substituted or unsubstituted $C_{3-10}$ cycloalkyl group" for $R_1$ means a $C_{3-10}$ cycloalkyl group (particularly preferably cyclopropyl and cyclohexyl) that may have a substituent selected from the above-described straight chain or branched $C_{1-10}$ alkyl group (particularly preferably methyl, tert-butyl, and isopentyl), an amino group, an amino group (particularly preferably methylamino, ethylamino, acetylamino, and benzylamino) that may be substituted with the above-described $C_{1-4}$ lower alkyl or acyl groups. Preferable examples the cycloalkyl group are cyclopropyl, cyclohexyl, 1-methylcyclohexyl, 1-isopentylcyclohexyl, 1-aminocyclohexyl, 1-acetylaminocyclohexyl, and 4-tert-butylcyclohexyl.

The "substituted or unsubstituted $C_{3-10}$ cycloalkyl $C_{1-10}$ alkyl group" for $R_1$ means a $C_{3-10}$ cycloalkyl $C_{1-10}$ alkyl group which may have a substituent selected from the above-described $C_{3-10}$ cycloalkyl group (particularly preferably cyclopentyl and cyclohexyl), the above-described $C_{5-8}$ cycloalkenyl group (particularly preferably cyclopentenyl and cyclohexenyl), and the above-described aryl group (particularly preferably a phenyl group) and in which the $C_{1-10}$ alkyl moiety is straight chain or branched. There is no special restriction on the position of substitution. The straight chain or branched $C_{1-10}$ alkyl moiety may be substituted. A cyclohexylmethyl group is preferred as the $C_{1-10}$ cycloalkyl $C_{1-10}$ alkyl group.

The "substituted or unsubstituted aryl group" for $R_1$ means an aryl group (particularly preferably phenyl and naphthyl) that may have a substituent selected from the above-described straight chain or branched $C_{1-6}$ alkyl group (particularly preferably methyl and tert-butyl group), the above-described halogen atom (particularly preferably fluorine and chlorine), a nitro group, a hydroxyl group, the above-described $C_{1-4}$ lower alkoxy group (particularly preferably a methoxy group), and the above-described acyl group (particularly preferably a 2-(1-isopentylcyclohexanecarbonylamino)phenylthiocarbonyl group). Preferable examples of the aryl group include phenyl, 1-naphthyl, 2-naphthyl, 2-chlorophenyl, 2,6-dichlorophenyl, 2,6-dimethylphenyl, 2-methoxyphenyl, 2-nitrophenyl, 4-nitrophenyl, 3,5-di-tert-butyl-4-hydroxyphenyl, and 4-[2-(1-isopentylcyclohexanecarbonylamino)phenylthiocarbonyl] phenyl.

The "substituted or unsubstituted aralkyl group" for $R_1$ means an aralkyl group (particularly preferably benzyl, phenethyl, 3-phenylpropyl, naphthylmethyl, and biphenylmethyl) that may have a substituent selected from the above-described halogen atom (particularly preferably fluorine and chlorine), a nitro group, an amino group (particularly preferably amino, acetylamino, pivaloylamino, 1-methylcyclohexanecarbonyl-amino, tert-butoxycarbonylamino, and benzoylamino) that may be substituted with the above-described $C_{1-4}$ lower alkyl group or the above-described acyl group, and a hydroxyl group, and in which the $C_{1-4}$ lower alkyl group are straight chain or branched. There is no special restriction on the position of substitution. The straight chain or branched $C_{1-4}$ lower alkyl moiety may be substituted. Preferable examples of the aralkyl group include benzyl, phenethyl, 3-phenylpropyl, 2-naphthylmethyl, 4-biphenylmethyl, benzhydryl, 2-chlorophenylmethyl, 3-chloro phenylmethyl, 4-chlorophenylmethyl, 2-nitrophenylmethyl, 4-nitrophenylmethyl, 2-pivaloylaminophenylmethyl, 2-(1-methylcyclohexanecarbonylamino)phenylmethyl, 2-tert-butoxy-carbonylaminophenylmethyl, 3-acetylaminophenylmethyl, 3-(1-methylcyclohexanecarbonylamino)phenylmethyl, α-aminobenzyl, α-acetylaminobenzyl, α-(1-methylcyclohexanecarbonylamino)benzyl, α-benzoylaminobenzyl, α-aminophenethyl, α-acetylaminophenethyl, and 1-acetylamino-2-(4-hydorxyphenyl) ethyl.

The "substituted or unsubstituted arylalkenyl group" for $R_1$ means an arylalkenyl group (particularly phenylvinyl) that may have a substituent selected from the above-described straight chain or branched $C_{1-6}$ lower alkyl group (particularly preferably methyl and tert-butyl), the above-described halogen atom (particularly preferably fluorine and chlorine), a nitro group, and a hydroxyl group, with a 2-phenylvinyl group being preferred.

The "substituted or unsubstituted arylthio group" for $R_1$ means an arylthio group (particularly preferably a phenylthio group) that may have a substituent selected from the above-described halogen atom (particularly preferably fluorine and chlorine), a nitro group, and an amino group that may be substituted with the above-described $C_{1-4}$ lower alkyl group or the above-described acyl group (particularly preferably amino, acetylamino, pivaloylamino, 1-methylcyclohexanecarbonylamino, and benzoylamino), a hydroxyl group, and the above-described halo-$C_{1-4}$ lower alkyl group (particularly preferably a trifluoromethyl group). Preferably examples of the arylthio group include phenylthio, 2-pivaloylaminophenylthio, 2-(1-methylcyclohexanecarbonylamino)phenylthio, and 2-(1-methyl cyclohexanecarbonylamino-4-trifluoromethyl) phenylthio.

The "substituted or unsubstituted 5- or 6-membered heterocyclic ring groups with 1–3 nitrogen, oxygen, or sulfur atoms" for $R_1$ means heterocyclic ring groups (particularly preferably an aromatic heterocyclic group such as pyridyl or a non-aromatic heterocyclic group such as piperidyl or pyrrolidinyl) that may have substituents selected from the above-described straight chain or branched $C_1$ alkyl group (particularly preferably a methyl group), a halogen atom (particularly preferably fluorine and chlorine), the above-described acyl group (particularly preferably acetyl and benzoyl), and an oxo group. Preferable examples thereof are 3-pyridyl, 1-methyl-4-piperidyl, 1-acetyl-4-piperidyl, 5-oxo-2-pyrrolidinyl, 1-acetyl-2-pyrrolidinyl, and 1-benzoyl-2-pyrrolidinyl. A 4-piperidyl group such as 1-methyl-4-piperidyl or 1-acetyl-4-piperidyl group is particularly preferred.

The "substituted or unsubstituted 5- or 6-membered heteroarylalkyl group" for $R_1$ means the above-described heteroarylalkyl group (particularly preferably a 2-tenyl group) that may be substituted with the above-described straight chain or branched $C_{1-6}$ alkyl group (particularly preferably a methyl group) and the above-described halogen atom (particularly preferably fluorine and chlorine). A 2-tenyl group is preferred.

The "substituted or unsubstituted $C_{1-4}$ lower alkyl group" for $R_2$ means a $C_{1-4}$ lower alkyl group (particularly preferably a methyl group) that may have 1–3 substituents selected from the above-described $C_{1-4}$ lower alkoxy group (particularly preferably a methoxy group), an amino group that may be substituted with the above-described $C_{1-4}$ lower alkyl or acyl group (particularly preferably a dimethylamino group), the above-described $C_{1-4}$ lower alkylthio group (particularly preferably a methylthio group), a carbamoyl group, a hydroxyl group, a carboxyl group, the above-described acyl group (particularly preferably a methoxycarbonyl group), and the above-described heterocyclic group (particularly preferably an aromatic heterocyclic group such as thienyl or a non-aromatic heterocyclic group such as tetrahydrofuryl). A tetrahydrofurylmethyl group is preferred.

The "substituted or unsubstituted aryl group" for $R_2$ is the same as that for $R_1$. Preferable examples thereof are a phenyl group, a halogenated phenyl group, an acylamino-substituted phenyl group, and the like.

The "halogen atom" for $X_1$, $X_2$, $X_3$, and $X_4$ means a halogen atom including fluorine, chlorine, bromine, and the like, with fluorine and chlorine being preferred.

The "$C_{1-4}$ lower alkyl group" for $X_1$, $X_2$, $X_3$, and $X_4$ is preferably a methyl group.

The "halo-$C_{1-4}$ lower alkyl group" for $X_1$, $X_2$, $X_3$, and $X_4$ means a $C_{1-4}$ lower alkyl group (particularly preferably a methyl group) substituted with the above-described halogen atom (particularly preferably fluorine and chlorine). A trifluoromethyl group is preferred.

The "$C_{1-4}$ lower alkoxy group" for $X_1$, $X_2$, $X_3$, and $X_4$, is preferably a methoxy group.

The "acyl group" for $X_1$, $X_{21}$ $X_3$, and $X_4$ is preferably a benzoyl group.

The "aryl group" for $X_1$, $X_2$, $X_3$, and $X_4$ is preferably a phenyl group.

The "1-substituted-$C_{3-10}$ cycloalkyl group" for R" means a cycloalkyl group (for example, cyclopropyl, cyclobutyl, cyclopentyl, cyclohexyl, and cycloheptyl, preferably a $C_{5-7}$ cycloalkyl group, particularly preferably a cyclohexyl group) that is substituted at position 1 with substituents selected from the above-described straight chain or branched $C_{1-10}$ alkyl group (particularly preferably a $C_{1-8}$ alkyl group such as methyl, ethyl, propyl, isopropyl, butyl, isobutyl, pentyl, isopentyl, 2,2-dimethylpropyl, 4-methylpentyl, or 2-ethylbutyl), the above-described straight chain or branched $C_{2-10}$ alkenyl group (particularly preferably a $C_{2-8}$ alkenyl group such as 1-methylvinyl, 2-methylvinyl, or 3-methyl-3-propenyl), the above-described $C_{3-10}$ cycloalkyl (particularly preferably a $C_{3-7}$ cycloalkyl group such as cyclopropyl, cyclopentyl, or cyclohexyl), the above-described $C_{5-8}$ cycloalkenyl group (particularly preferably a C., cycloalkenyl group such as cyclopentenyl or cyclohexenyl), the above-described $C_{3-10}$ cycloalkyl $C_{1-10}$ alkyl group (particularly preferably a $C_{3-7}$ cycloalkyl $C_{1-4}$ lower alkyl group such as cyclopropylmethyl, 2-cyclopropylethyl, 2-cyclopentylethyl, cyclohexylmethyl, or 2-cyclohexylethyl), the above-described aryl group (particularly preferably a phenyl group), the above-described aralkyl group (particularly preferably a phenyl $C_{1-4}$ lower alkyl group such benzyl and phenethyl), and an arylalkenyl group (particularly preferably 2-phenylvinyl). Preferable examples of the 1-substituted-$C_{3-10}$ cycloalkyl group include 1-isopentylcyclobutyl, 1-isopropylcyclopentyl, 1-isobutylcyclopentyl, 1-isopentyl cyclopentyl, 1-cyclohexylmethylcyclopentyl, 1-methylcyclohexyl, 1-ethylcyclohexyl, 1-propylcyclohexyl, 1-isopropylcyclohexyl, 1-butylcyclohexyl, 1-isobutylcyclohexyl, 1-pentylcyclohexyl, 1-isopentylcyclohexyl, 1-(2,2-dimethylpropyl)cyclohexyl, 1-(4-methylpentyl)cyclohexyl, 1-(2-ethylbutyl)cyclohexyl, 1-cyclopropylcyclohexyl, 1-bicyclohexyl, 1-phenylcyclohexyl, 1-cyclopropylmethylcyclohexyl, 1-cyclohexylmethylcyclohexyl, 1-(2-cyclopropylethyl) cyclohexyl, 1-(2-cyclopentylethyl)cyclohexyl, 1-(2-cyclohexylethyl)cyclohexyl, and 1-isopentylcycloheptyl. The straight chain or branched $C_{1-10}$ alkyl group is particularly preferable as a substituent at position 1.

The "1-substituted-$C_{5-8}$ cycloalkenyl group" for R" means a cycloalkenyl groups (particularly preferably a $C_{5-6}$ cycloalkenyl group such as cyclopentenyl or cyclohexenyl) that is substituted at position 1 with substituents selected from the above-described straight chain or branched $C_{1-10}$ alkyl group (particularly preferably a $C_1$ alkyl group such as methyl, ethyl, propyl, isopropyl, butyl, isobutyl, pentyl, isopentyl, 2,2-dimethyl propyl, and 4-methylpentyl), the above-described straight chain or branched $C_{2-10}$ alkenyl group (particularly preferably a $C_{2-8}$ alkenyl group such as 1-methylvinyl, 2-methylvinyl, or 3-methyl-3-propenyl), the above-described $C_{3-10}$ cycloalkyl group (particularly preferably a $C_{3-7}$ cycloalkyl group such as cyclopropyl, cyclopentyl, or cyclohexyl), the above-described $C_{5-8}$ cycloalkenyl group (particularly preferably a $C_{1-6}$ cycloalkenyl group such as cyclopentenyl or cyclohexenyl), the above-described $C_{3-10}$ cycloalkyl $C_{1-10}$ alkyl group (particularly preferably a $C_{3-7}$ cycloalkyl $C_{1-4}$ lower alkyl group such as cyclopropylmethyl, 2-cyclopropylethyl, 2-cyclopentylethyl, cyclohexylmethyl, or 2-cyclohexylethyl), the above-described aryl group (particularly preferably a phenyl group), the above-described aralkyl group (particularly preferably a phenyl $C_{1-4}$ lower alkyl group such as benzyl or phenethyl), and the above-described arylalkenyl group (particularly preferably a 2-phenylvinyl group). Preferable examples of the 1-substituted-$C_{5-8}$ cycloalkenyl group include 1-isopropyl-2-cyclopentenyl, 1-isopropyl-3-cyclopentenyl, 1-isobutyl-2-cyclopentenyl, 1-isobutyl-3-cyclopentenyl, 1-isopentyl-2-cyclopentenyl, 1-isopentyl-3-cyclopentenyl, 1-cyclohexylmethyl-2-cyclopentenyl, 1-cyclohexylmethyl-3-cyclopentenyl, 1-methyl-2-cyclohexenyl, 1-methyl-3-cyclohexenyl, 1-ethyl-2-cyclohexenyl, 1-ethyl-3-cyclohexenyl, 1-propyl-2-cyclohexenyl, 1-propyl-3-cyclohexenyl, 1-isopropyl-2-cyclohexenyl, 1-isopropyl-3-cyclohexenyl, 1-butyl-2-cyclohexenyl, 1-butyl-3-cyclohexenyl, 1-isobutyl-2-cyclohexenyl, 1-isobutyl-3-cyclohexenyl, 1-pentyl-2-cyclohexenyl, 1-pentyl-3-cyclohexenyl, 1-isopentyl-2-cyclohexenyl, 1-isopentyl-3-cyclohexenyl, 1-(2,2-dimethylpropyl)-2-cyclohexenyl, 1-(2,2-dimethylpropyl)-3-cyclohexenyl, 1-(4-methylpentyl)-2-cyclohexenyl, 1-(4-methylpentyl)-3-cyclohexenyl, 1-cyclopropyl-2-cyclohexenyl, 1-cyclopropyl-3-cyclohexenyl, 1-cyclohexyl-2-cyclohexenyl, 1-cyclohexyl-3-cyclohexenyl, 1-phenyl-2-cyclohexenyl, 1-phenyl-3-cyclohexenyl, 1-cyclopropylmethyl-2-cyclohexenyl, 1-cyclopropylmethyl-3-cyclohexenyl, 1-cyclohexylmethyl-2-cyclohexenyl, 1-cyclohexylmethyl-3-cyclohexenyl, 1-(2-cyclopropylethyl)-2-cyclohexenyl, 1-(2-cyclopropylethyl)-3-cyclohexenyl, 1-(2-cyclopentylethyl)-2-cyclohexenyl, 1-(2-cyclopentylethyl)-3-cyclohexenyl, 1-(2-cyclohexylethyl)-2-cyclohexenyl, and 1-(2-cyclohexylethyl)-3-cyclohexenyl. The straight chain or branched $C_{1-10}$ alkyl group is particularly preferable as a substituent at position 1.

The "prodrug compound" means the derivatives of compounds of the present invention having a chemically or metabolically degradable group, which exhibit pharmaceutical activity by degradation through hydrolysis or solvolysis, or under physiological conditions.

The "pharmaceutically acceptable salt" means any compound that is an atoxic salt formed with the compound represented by the above formula (I). Examples of such a salt include inorganic acid salts such as hydrochlorides, hydrobromides, hydroiodides, sulfates, nitrates, phosphates, carbonates, bicarbonates, or perchlorates; organic acid salts such as formates, acetates, trifluoroacetates, propionates, tartrates, glycolates, succinates, lactates, maleates, hydroxymaleates, methylmaleates, fumarates, adipiates, tartrates, malates, citrates, benzoates, cinnamates, ascorbates, salicylates, 2-acetoxybenzoates, nicotinates, or isonicotinates; sulfonates such as methane sulfonates, ethane sulfonates, isethionates, benzene sulfonates, p-toluene sulfonates, or naphthalene sulfonates; salts of acidic amino acids such as aspargates or glutamates; alkali metal salts such as sodium salts or potassium salts, alkaline earth metal salts such as magnesium salts or calcium salts; ammonium salts; organic base salts such as trimethylamines, triethylamnes, pyridine salts, picoline salts, dicyclohexylamine salts or N,N'-dibenzyl ethylenediamine salts; and salts of amino acids such as lysine salts or arginine salts. Depending on the circumstances, hydrates or solvates with alcohols may be used.

More specifically, a 1-isobutylcyclohexyl group, a 1-(2-ethylbutyl) cyclohexyl group, and a 1-isopentylcyclohexyl group are particularly preferable as R in the formula (I), —CO— is particularly preferable as Y, a hydrogen atom is particularly preferable as $X_1$, $X_2$, $X_3$, and $X_4$, and an isobutyryl group and a I-acetyl-4-piperidine carbonyl group are particularly preferable as Z.

The compound of the present invention inhibits CETP activity and is expected as a conventionally unknown, new type of a preventive or therapeutic agent for hyperlipidemia or atherosclerotic diseases.

When used as a pharmaceutical preparation, the compound of the present invention represented by the formula (I) or a pharmaceutically acceptable salt thereof can be usually used together with known pharmacologically acceptable carriers, excipients, diluents, extenders, disintegrators, stabilizers, preservatives, buffers, emulsifiers, aromatics, colorants, sweeteners, viscosity increasing agents, flavor improving agents, solubilizers, and other additives. More specifically, the compound can be formulated into dosage forms, such as tablets, pills, powders, granules, suppositories, injections, eye drops, liquid drugs, capsules, troches, aerosols, elixirs, suspensions, emulsions, or syrup, together with water, plant oil, alcohols such as ethanol or benzyl alcohol, polyethylene glycol, glyceroltriacetate gelatin, lactose, carbohydrates such as starch, magnesium stearates, talc, lanolin, and vaseline, which can be administered orally or parenterally.

The above pharmaceutical preparations contain the compound of the present invention represented by the formula (I) or a pharmaceutically acceptable salt thereof in an amount effective to inhibit CETP activity and prevent or treat hyperlipidemia, atherosclerotic diseases, or the like diseases attributable to CETP activity. One skilled in the art can easily determine such an effective amount.

Doses may vary depending on the type and degree of diseases, the compounds to be administered, the route of administration, the age, sex, and body weight of the patients. In the case of oral administration, it is usually desirable to administer the compound (I) to an adult 1–1000 mg, particularly 50–800 mg per day.

The compound of the present invention can be produced using the following method, but it is needless to say that the method of producing the compound of the present invention is not limited to this method.

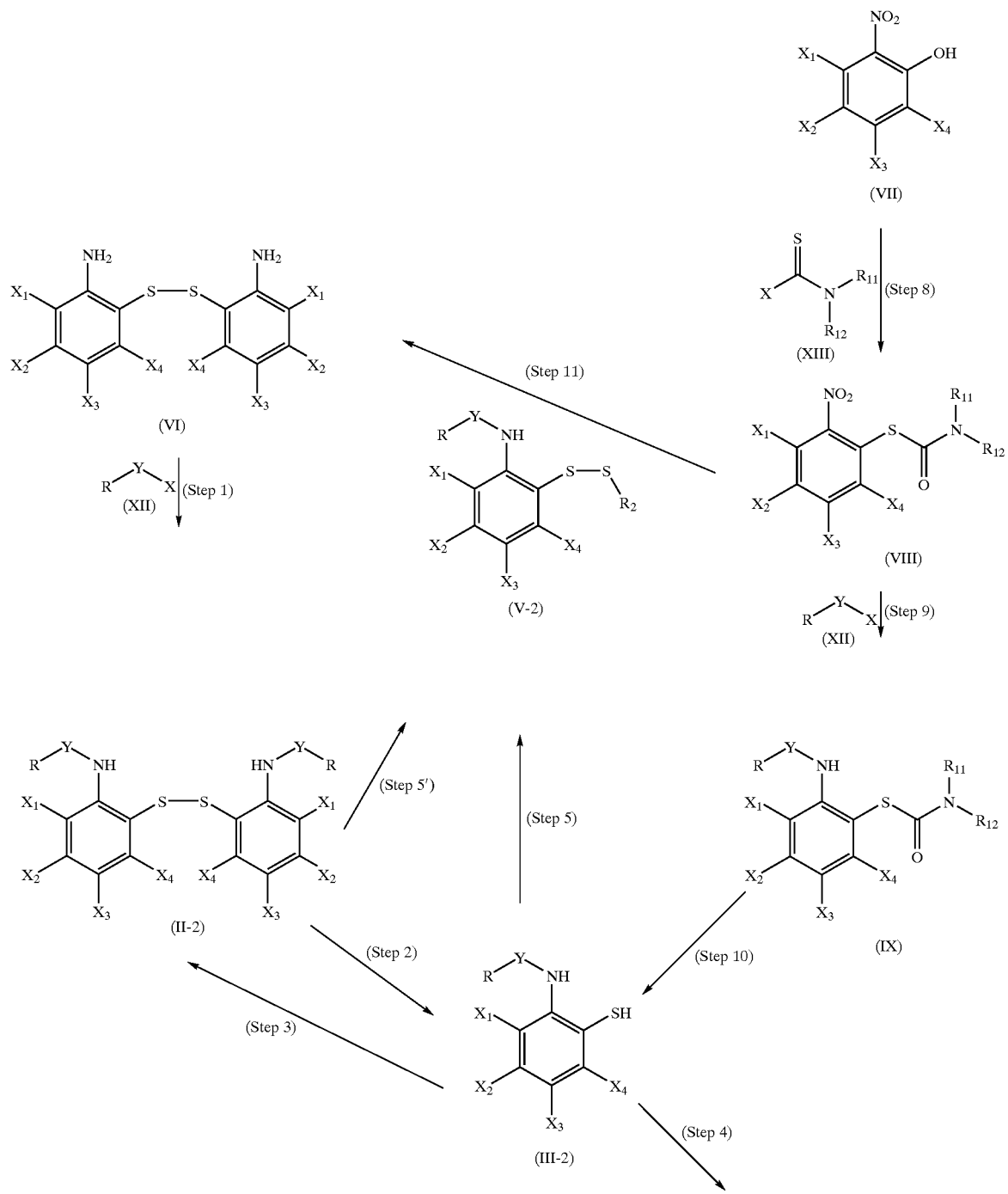

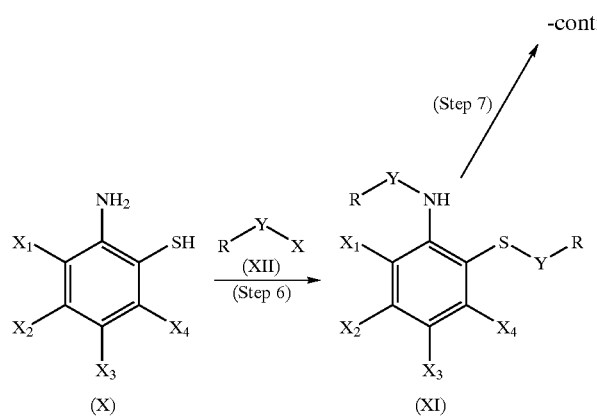

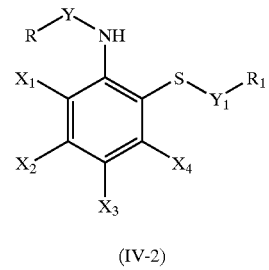

(IV-2)

[Step 1]

The compound (II-2) (in the formula R, $X_1$, $X_2$, $X_3$, $X_4$, and Y are as described above) can be synthesized by reacting the compound (VI) (in the formula $X_1$, $X_2$, $X_3$, and $X_4$ are as described above) with the compound (XII) (in the formula X represents a halogen atom and R and Y are as described above) in the presence of a base such as pyridine, triethylamine, N-methylmorpholine, or N-methylpiperazine in an organic solvent such as methylene chloride, chloroform, toluene, ether, tetrahydrofuran, dioxane, diisopropyl ether, dimethoxyethane, or hexane, water, or a mixture of these solvents, or in the absence of a solvent, under cooling through heating temperature.

The compound (III-2) can be synthesized from the compound (II-2) by the following step 2.

[Step 2]

The compound (III-2) (in the formula R, $X_1$, $X_2$, $X_3$, $X_4$, and Y are as described above) can be synthesized by allowing the compound (II-2) (in the formula R, $X_1$, $X_2$, $X_3$, $X_4$, and Y are as described above) to react in the presence of a reducing agent such as sodium borohydride, lithium borohydride, aluminum lithium hydride, triphenylphosphine, zinc, or tin, in an organic solvent such as methanol, ethanol, ether, dioxane, tetrahydrofuran, diisopropyl ether, dimethoxyethane, toluene, hexane, acetone, or acetic acid, water, or a mixture of these solvents, under cooling through heating temperature.

The compound (II-2) or (IV-2) can also be synthesized from the compound (III-2) using the following step 3 or 4.

[Step 3]

The compound (II-2) (in the formula R, $X_1$, $X_2$, $X_3$, $X_4$, and Y are as described above) can be synthesized by allowing the compound (III-2) (in the formula R, $X_1$, $X_2$, $X_3$, $X_4$, and Y are as described above) to react in the presence of an oxidizing agent such as iodine, hydrogen peroxide, potassium permanganate, or dimethylsulfoxide, in an organic solvent such as methanol, ethanol, ether, dioxane, tetrahydrofuran, diisopropyl ether, dimethoxyethane, acetone, toluene, hexane, dimethylformamide, or acetic acid, water, or a mixture of these solvents, or in the absence of a solvent, under cooling through heating temperature.

[Step 4]

The compound (IV-2) (in the formula R, $R_1$, $X_1$, $X_2$, $X_3$, $X_4$, Y, and $Y_1$ are as described above) can be synthesized by reacting the compound (III-2) (in the formula R, $X_1$, $X_2$, $X_3$, $X_4$, and Y are as described above) with acid halide $R_1$—YX (in the formula $R_1$, X, and Y are as described above), isocyanate $R_1$—NY (in the formula $R_1$ and Y are as described above), carbonic halide $R_1$—O—YX (in the formula $R_1$, X, and Y are as described above), or thiocarbonic halides $R_1$—S—YX (in the formula $R_1$, X and Y are as described above) in the presence of a base such as pyridine, triethylamine, N-methylmorpholine, or N-methylbipiperazine, in an organic solvent such as methylene chloride, chloroform, toluene, ether, dioxane, tetrahydrofuran, diisopropyl ether, dimethoxy ethane, or hexane, water, or a mixture of these solvents, or in the absence of a solvent, under cooling through heating temperature. Alternatively, the compound (IV-2) can be synthesized by reacting the compound (III-2) with carboxylic acid $R_1$—COOH (in the formula $R_1$ is as described above) or thiocarboxylic acid $R_1$—YSH (in the formula $R_1$ and Y are as described above) using a coupling agent such as 1-ethyl-3-(3-dimethylaminopropyl)carbodiimide hydrochloride, dicyclohexylcarbodiimide, diphenylphosphorylazide, or carbonyldiimidazole, in the presence of an activating agent, if required, such as 1-hydroxybenzotriazole, hydroxysuccinimide, or N-hydroxy-5-norbornene-2,3-dicarboxylic acid imide, in an organic solvent such as dimethylformamide, dichloromethane, chloroform, acetonitrile, tetrahydrofuran, dimethylsufoxide, carbon tetrachloride, or toluene, or a mixture of these solvents, under cooling through heating temperature. (The reaction may be carried out in the presence of a base such as pyridine or triethylamine.) Furthermore, the compound (IV-2) can be synthesized by reacting the compound (III-2) with carboxylic acid $R_1$—COOH (in the formula $R_1$ is as described above) in the presence of a base such as triethylamine or pyridine and in the presence of ethyl chlorocarbonate or the like, in a organic solvent such as ethyl acetate or tetrahydrofuran, or a mixture of these solvents, under cooling through heating temperature. When $R_1$ has a carboxyl group, this above step may be conducted using the corresponding ester to obtain the compound by hydrolysis with acid using the known method.

The compound (IV-2) can also be synthesized by subsequently conducting the step 4 following the above step 2 or the step 7 below, or the step 10 below, without isolating the compound (III-2).

The compound (V-2) can be synthesized by conducting the following step 5 or 5'. The step 5 is suitable especially when $R_2$ is the lower alkyl group that may have substituents and the step 5' is suitable especially when $R_2$ is the aryl group that may have substituents.

[Step 5]

The compound (V-2) (in the formula R, $R_2$, $X_1$, $X_2$, $X_3$, $X_4$, and Y are as described above) can be synthesized by allowing $R_2$—X (in the formula $R_2$ and X is as described above) and a sulfur compound like sodium thiosulfate to react in an organic solvent such as ethanol, methanol, tetrahydrofuran, dioxane, dimethoxyethane, acetone, or acetonitrile, water, or a mixture of these solvents, at room temperature through heating temperature, and adding the compound (III-2) (in the formula R, $X_1$, $X_2$, $X_3$, $X_4$, and Y are as described above) and a basic aqueous solution such as sodium hydroxide, potassium hydroxide, sodium carbonate, potassium carbonate, or sodium bicarbonate to the resulting solution under ice-cooling through heating temperature.

[Step 5']

The compound (V-2) (in the formula R, $R_2$, $X_1$, $X_2$, $X_3$, $X_4$, and Y are as described above) can be synthesized by reacting $R_2$—SH (in the formula $R_2$ is as described above) with trimethylsilane-imidazole in carbon tetrachloride under ice-cooling through room temperature, adding to the resulting solution a reaction mixture resulted from reacting the compound (II-2) (in the formula R, $X_1$, $X_2$, $X_3$, $X_4$, and Y are as described above) with sulfuryl chloride in carbon tetrachloride in the presence of a base such as triethylamine, pyridine, N-methylmorpholine, or N-methylpiperazine under ice-cooling through room temperature, and allowing the resulting mixture to react.

The compound (III-2) can also be synthesized using the following scheme.

[Step 6]

The compound (XI) (in the formula R, $X_1$, $X_2$, $X_3$, $X_4$, and Y are as described above) can be synthesized by reacting the compound (X) (in the formula $X_1$, $X_2$, $X_3$, and $X_4$ are as described above) with the compound (XII) (in the formula R, X, and Y are as described above) in the presence of a base such as pyridine, triethylamine, N-methylmorpholine, or N-methylpiperazine, in an organic solvent such as methylene chloride, chloroform, toluene, ether, dioxane, tetrahydrofuran, diisopropyl ether, dimethoxyethane, or hexane, water, or a mixture of these solvents, or in the absence of a solvent, under cooling through heating temperature.

[Step 7]

The compound (III-2) (in the formula R, $X_1$, $X_2$, $X_3$, $X_4$, and Y are as described above) can be synthesized by allowing the compound (XI) (in the formula R, $X_1$, $X_2$, $X_3$, $X_4$, and Y are as described above) to react in the presence of a base such as sodium acetate, sodium hydroxide, potassium hydroxide, potassium carbonate, sodium carbonate, or sodium bicarbonate, in an organic solvent such as methanol, ethanol, tetrahydrofuran, dioxane, dimethoxyethane, ether, or diisopropyl ether, water, or a mixture of these solvents, under ice-cooling through heating temperature.

The compound (III-2) can also be synthesized by the following scheme.

[Step 8]

The compound (VIII) (in the formula $R_{11}$ and $R_{12}$ may be-the same or different and are a lower alkyl group such as methyl or ethyl, and $X_1$, $X_2$, $X_3$, and $X_4$ are as described above) can be synthesized by reacting the compound (VII) (in the formula $X_1$, $X_2$, $X_3$, and $X_4$ are as described above) with the compound (XIII) (in the formula $R_{11}$, $R_{12}$, and X are as described above) in the presence of a base such as sodium hydride, triethylamine, or N-methylmorpholine, in an organic solvent such as dimethylformamide, tetrahydrofuran, dioxane, or dimethoxyethane or a mixture of these solvents, under cooling through heating temperature, and allowing the resulting product to react in an organic solvent such as phenylether or sulfolane or a mixture of these solvents, or in the absence of a solvent, under heating.

[Step 9]

The compound (IX) (in the formula R, $R_{11}$, $R_{12}$, $X_1$, $X_2$, $X_3$, $X_4$, and Y are as described above) can be synthesized by allowing the compound (VIII) (in the formula $R_{11}$, $R_{12}$, $X_1$, $X_2$, $X_3$, and $X_4$ are as described above) to react in the presence of a reducing agent such as stannous chloride, zinc, iron, sodium dithionite, sodium sulfide, or sodium disulfide, in an organic solvent such as ethyl acetate, acetic acid, methanol, ethanol, tetrahydrofuran, dioxane, diisopropyl ether, dimethoxyethane, or toluene, water, or a mixture of these solvents, under cooling through heating temperature, and reacting the resulting product with the compound (XII) (in the formula R, X, and Y are as described above) in the presence of a base such as pyridine, triethylamine, N-methylmorpholine, or N-methylpiperazine, in an organic solvent such as chloroform, methylene chloride, tetrahydrofuran, ether, dioxane, diisopropyl ether, dimethoxyethane, toluene, or hexane, water or a mixture of these solvents, or in the absence of a solvent, under cooling through heating temperature.

[Step 10]

The compound (III-2) (in the formula R, $X_1$, $X_2$, $X_3$, $X_4$, and Y are as described above) can be synthesized by allowing the compound (IX) (in the formula R, $R_{11}$, $R_{12}$, $X_1$, $X_2$, $X_3$, $X_4$, and Y are as described above) to react in the presence of a base such as potassium hydroxide, sodium hydroxide, potassium carbonate, sodium carbonate, or sodium bicarbonate, in an organic solvent such as methanol, ethanol, tetrahydrofuran, dioxane, dimethoxyethane, ether, or diisopropyl ether, water, or a mixture of these solvents, under cooling through heating temperature.

The compound (VI) can also be synthesized from the compound (VIII) by the following step 11.

[Step 11]

The compound (VI) (in the formula $X_1$, $X_2$, $X_3$, and $X_4$ are as described above) can be synthesized by allowing the compound (VIII) (in the formula $R_{11}$, $R_{12}$, $X_1$, $X_2$, $X_3$, and $X_4$ are as described above) to react in the presence of a reducing agent such as stannous chloride, zinc, iron, sodium dithionite, sodium sulfide, and sodium disulfide, in an organic solvent such as ethyl acetate, acetic acid, methanol, ethanol, ether, tetrahydrofuran, dioxane, diisopropyl ether, dimethoxyethane, and toluene, water or a mixture of these solvents, under cooling through heating temperature, allowing the resulting product to react in the presence of a base such as potassium hydroxide, sodium hydroxide, potassium carbonate, sodium carbonate, or sodium bicarbonate, in an organic solvents such as methanol, tetrahydrofuran, ethanol, dioxane, ether, diisopropyl ether, or dimethoxyethane, water, or a mixture of these solvents, under cooling through heating temperature, and allowing the product to react in the presence of an oxidizing agent such as iodine, hydrogen peroxide, potassium permanganate, or dimethylsufoxide, in an organic solvent such as methanol, ethanol, ether, dioxane, tetrahydrofuran, diisopropyl ether, dimethoxyethane, acetone, toluene, hexane, dimethylformamide, or acetic acid, water, or a mixture of these solvents, or in the absence of a solvent, under cooling through heating temperature.

The compound (I) thus obtained can be isolated and purified using the known method for separation and purification, such as concentration, concentration under reduced pressure, extraction, crystallization, recrystallization, or chromatography.

The compound of the present invention contains one or more of stereoisomers due to the presence of the asymmetric carbon. Such isomers and mixtures thereof are all included in the scope of the present invention.

BEST MODE FOR CARRYING OUT THE INVENTION

In the following the present invention will be described in detail with reference to Examples and Test Example, but the present invention is not limited thereto.

EXAMPLE 1

Synthesis of bis-[2-(pivaloylamino)phenyl] disulfide (formula (I); R=t-butyl, $X_1$, $X_2$, $X_3$, $X_4$= a hydrogen atom, Y=carbonyl, Z=2-(pivaloylamino)phenylthio)

Step 1) A mixture of bis-(2-aminophenyl) disulfide (8.00 g), pyridine (6.5 ml), and chloroform (150 ml) was stirred at 0° C., to which pivaloyl chloride (83 ml) was added dropwise. After completion of addition, the organic layer was washed with water and saturated brine. After drying the organic layer over anhydrous sodium sulfate and evapolation, solid material was obtained. The solid thus obtained was washed with ether-hexane and collected by filtration to give the desired compound (11.15 g, yield: 83%).

EXAMPLE 2

Synthesis of bis-[2-[1-(2-ethylbutyl)cyclohexanecarbonylamino]-phenyl disulfide (formula (I); R=1-(2-ethylbutyl)cyclohexyl, $X_1$, $X_2$, $X_3$, $X_4$=a hydrogen atom, Y=carbonyl, Z=2-[1-(2-ethylbutyl)-cyclohexanecarbonylamino]phenylthio).

i) A suspension of 60% sodium hydride (980 mg) in tetrahydrofuran (80 ml) was stirred at room temperature and a tetrahydrofuran solution (10 ml) containing cyclohexanecarboxylic acid (3.00 g) was added dropwise thereto. After completion of addition, a mixture was stirred for 1 hour and cooled to 0° C., followed by adding a cyclohexane solution (18.7 ml) containing 1.5 M lithium isopropylamide dropwise thereto. Then, after stirring at room temperature for 1.5 hours and cooling to 0° C., a tetrahydrofuran solution (10 ml) containing 1-bromo-2-ethylbutane (4.64 g) was added dropwise thereto. The solution was gradually warmed to room temperature and stirred overnight. Water and a 10% hydrochloride solution were added to this reaction solution and the solution was extracted with ethyl acetate. The organic layer was washed with saturated brine and dried over anhydrous sodium sulfate. After drying, the resulting solution was concentrated to obtain 1-(2-ethylbutyl)cyclohexanecarboxylic acid (3.17 g, yield: 64%).

ii) A mixture of 1-(2-ethylbutyl)cyclohexane carboxylic acid (1.50 g) obtained in the above i), oxalyl chloride (0.85 ml), methylene chloride (20 ml), and a small amount of dimethylformamide was stirred at room temperature for 1 hour, concentrated under reduced pressure to obtain 1-(2-ethylbutyl) cyclohexanecarbonyl chloride as a crude product.

Step 1) A pyridine solution (20 ml) containing bis-(2-aminophenyl) disulfide (825 mg) was stirred at room temperature and a crude product of 1-(2-ethylbutyl) cyclohexanecarbonylchloride obtained in the above ii) was added dropwise thereto. After completion of addition, the solution was stirred overnight at 100° C. After concentration under reduced pressure, water was added to the reaction solution and the solution was extracted with ethyl acetate. The organic layer was washed with saturated brine and dried over anhydrous sodium sulfate, followed by concentration. The resulting residue was purified by silica gel column chromatography (a developing solvent; hexane:ethyl acetate=15:1) to obtain the desired compound (667 mg, yield: 32%).

EXAMPLES 3–8

The compounds shown in Tables 1 and 2 were obtained in the same manner as in Examples 1 and 2.

TABLE 1

| Example | Compound | m.p. (° C.) | $^1$H NMR (CDCl$_3$ 300MHz) |
|---|---|---|---|
| 1 | (structure) | 86–87 | 8.52(2H, brs)<br>8.46(2H, dd, J=1.5, 8.4Hz)<br>7.40(2H, ddd, J=1.5, 7.8, 8.4Hz)<br>7.21(2H, dd, J=1.5, 7.8Hz)<br>6.94(2H, dt, J=1.5, 7.8Hz)<br>1.25(18H, s) |
| 2 | (structure) | Amorphous | 8.58(2H, brs)<br>8.48(2H, dd, J=1.5, 8.4Hz)<br>7.42(2H, ddd, J=1.5, 7.8, 8.4Hz)<br>7.13(2H, dd, J=1.5, 7.8Hz)<br>6.92(2H, dt, J=1.5, 7.8Hz)<br>1.90–2.10(4H, m)<br>1.10–1.80(30H, m)<br>0.78(12H, t, J=7.2Hz) |

TABLE 1-continued

| Example | Compound | m.p. (° C.) | ¹H NMR (CDCl₃ 300MHz) |
|---|---|---|---|
| 3 | | 144–145 | 8.93(2H, brs)<br>8.50(2H, dd, J=1.5, 8.4Hz)<br>7.69(4H, dd, J=1.5, 8.4Hz)<br>7.40–7.60(8H, m)<br>7.31(2H, dt, J=1.5, 8.4Hz)<br>6.95(2H, dt, J=1.5, 7.8Hz) |
| 4 | | 156–157 | 8.78(2H, brs)<br>8.40(2H, dd, J=1.5, 8.4Hz)<br>7.55(2H, dd, J=1.2, 5.1Hz)<br>7.20–7.45(6H, m)<br>7.10(2H, dt, J=1.2, 5.1Hz)<br>6.95(2H, dt, J=1.5, 7.8Hz) |
| 5 | | 157–158 | 8.44(2H, dd, J=1.5, 8.4Hz)<br>8.04(2H, brs)<br>7.41(2H, ddd, J=1.5, 7.8, 8.4Hz)<br>7.24(2H, dd, J=1.5, 7.8Hz)<br>6.96(2H, dt, J=1.5, 7.8Hz)<br>2.05–2.20(2H, m)<br>1.20–1.70(16H, m)<br>0.93(12H, t, J=7.2Hz) |
| 6 | | Amorphous | 8.51(2H, brs)<br>8.48(2H, dd, J=1.5, 8.4Hz)<br>7.40(2H, ddd, J=1.5, 7.8, 8.4Hz)<br>7.22(2H, dd, J=1.5, 7.8Hz)-<br>6.95(2H, dt, J=1.5, 7.8Hz)<br>1.80–2.00(4H, m)<br>1.25–1.70(16H, m)<br>1.18(6H, s) |

TABLE 2

| Example | Compound | m.p. (° C.) | ¹H NMR (CDCl₃ 300MHz) |
|---|---|---|---|
| 7 | | Amorphous | 8.46(2H, dd, J=1.5, 8.4Hz)8.41(2H, brs)<br>7.40(2H, ddd, J=1.5, 7.8, 8.4Hz)<br>7.13(2H, dd, J=1.5, 7.8Hz)<br>6.91(2H, dt, J=1.5, 7.8Hz)<br>2.00–2.15(4H, m)<br>1.45–1.75(18H, m)<br>1.15–1.25(4H, m)<br>0.87(12H, d, J=6.6Hz) |
| 8 | | Amorphous | 8.50(2H, brs)<br>8.49(2H, dd, J=1.5, 8.4Hz)<br>7.41(2H, ddd, J=1.5, 7.8, 8.4Hz)<br>7.15(2H, dd, J=1.5, 7.8Hz)<br>6.92(2H, dt, J=1.5, 7.8Hz)<br>1.89–2.00(4H, m)<br>1.10–1.66(26H, m)<br>0.85(12H, d, J=6.6Hz) |

The compounds 1-1 through 1-19 shown in Tables 3 and 4 were obtained in the same manner as in Examples 1 and 2.

TABLE 3

| No. | Compound |
|---|---|
| 1-1 | (isobutyramide-phenyl disulfide) |
| 1-2 | (pentanamide-phenyl disulfide) |
| 1-3 | (acetamide-phenyl disulfide) |
| 1-4 | (propionamide-phenyl disulfide) |
| 1-5 | (furan-2-carboxamide-phenyl disulfide) |
| 1-6 | (cyclohexanecarboxamide-phenyl disulfide) |

TABLE 3-continued

| No. | Compound |
|---|---|
| 1-7 | (isonicotinamide-phenyl disulfide) |
| 1-8 | (octanamide-phenyl disulfide, $H_3C-(CH_2)_6-$) |
| 1-9 | (isovaleramide-phenyl disulfide) |
| 1-10 | (2-chlorobenzamide-phenyl disulfide) |
| 1-11 | (phenylacetamide-phenyl disulfide) |
| 1-12 | (adamantane-1-carboxamide-phenyl disulfide) |

TABLE 4

| No. | Compound |
|---|---|
| 1-13 | Cyclohexanecarboxamide with 4-t-Bu substituent, linked via NH to 2-position of phenyl, disulfide bridge to symmetric partner |
| 1-14 | 2,2,2-triphenylacetamide-NH-phenyl-S-S-phenyl-NH-acetamide(Ph)₃ |
| 1-15 | 3,5-di-t-butylbenzamide-NH-phenyl-S-S-phenyl-NH-benzamide-3,5-di-t-Bu |
| 1-16 | Trifluoroacetamide-NH-phenyl-S-S-phenyl-NH-COCF₃ |
| 1-17 | 4-nitrobenzamide-NH-phenyl-S-S-phenyl-NH-benzamide-4-NO₂ |
| 1-18 | Camphorsulfonamide derivative, bis, S-S bridged |

TABLE 4-continued

| No. | Compound |
|---|---|
| 1-19 | Phenylsulfonamide-NH-phenyl-S-S-phenyl-NH-SO₂Ph |

EXAMPLE 9

Synthesis of N-(2-mercaptophenyl)-2,2-dimethylpropioneamide (formula (I); R=t-butyl, $X_1$, $X_2$, $X_3$, $X_4$=a hydrogen atom, Y=carbonyl, Z=a hydrogen atom).

Step 2) A mixture of bis-[2-(pivaloylamino)phenyl] disulfide (300 mg) obtained in Example 1 above in methanol (0.4 ml)-tetrahydrofuran (4 ml) was stirred at room temperature. Sodium borohydride (70 mg) was added thereto and the resulting solution was refluxed under heating for 4 hours. After cooling and addition of 10% hydrochloric acid, the resulting solution was extracted with ethyl acetate. The organic layer was washed with water, and saturated brine, and was dried over anhydrous sodium sulfate. After drying, the solution was concentrated and the resulting residue was separated and purified by silica gel column chromatography (a developing solvent; hexane:ethyl acetate=10:1) to obtain the desired compound (84 mg, yield: 28%3.

EXAMPLE 10

Synthesis of N-(2-mercaptophenyl)-1-(2-ethylbutyl) cyclohexanecarboxamide (formula (I); R=1-(2-ethylbutyl) cyclohexyl, $X_1$, $X_{21}$ $X_3$, $X_4$=a hydrogen atom, Y=carbonyl, Z=a hydrogen atom)

Step 2) A mixture of bis-[2-[1-(2-ethylbutyl)cyclohexanecarbonylamino]phenyl] disulfide (667 mg) obtained in Example 2 above, triphenylphosphine (577 mg), dioxane (8 ml), and water (4 ml) was stirred for 1 hour at 50° C. After allowing the mixture to cool, a 1 N aqueous sodium hydroxide was added thereto. The aqueous layer was washed with hexane and neutralized with a 10% hydrochloride solution. After extraction with ethyl acetate, the solution was washed with saturated brine and dried over anhydrous sodium sulfate. After drying, the solution was concentrated and the thus-obtained residue was purified by silica gel column chromatography (a developing solvent; hexane:ethyl acetate=15:1), which resulted in the desired compound (378 mg, yield: 56%).

TABLE 5

| Example | Compound | m.p. (° C.) | ¹H NMR (CDCl₃ 300MHz) |
|---|---|---|---|
| 9 | Pivaloylamino-2-mercaptophenyl (t-Bu-C(O)-NH-C₆H₄-SH) | 69–71 | 8.42(1H, brs)<br>8.31(1H, dd, J=1.5, 8.4Hz)<br>7.50(1H, dd, J=1.5, 7.8Hz)<br>7.30(1H, ddd, J=1.5, 7.8, 8.4Hz)<br>7.00(1H, dt, J=1.5, 7.8Hz)<br>3.08(1H, s)<br>1.36(9H, s) |

TABLE 5-continued

| Example | Compound | m.p. (° C.) | $^1$H NMR (CDCl$_3$ 300MHz) |
|---|---|---|---|
| 10 | (structure: 1-(2-ethylbutyl)-N-(2-mercaptophenyl)cyclohexanecarboxamide) | 68.5–74.0 | 8.45(1H, brs)<br>8.33(1H, dd, J=1.5, 8.4Hz)<br>7.51(1H, dd, J=1.5, 7.8Hz)<br>7.31(1H, ddd, J=1.5, 7.8, 8.4Hz)<br>7.00(1H, dt, J=1.5, 7.8Hz)<br>3.07(1H, s)<br>2.05–2.25(2H, m)<br>1.20–1.80(15H, m)<br>0.79(6H, t, J=6.9Hz) |

EXAMPLE 11

Synthesis of N-(2-mercaptophenyl)-1-isopentylcyclohexane-carboxamide (formula (I); R=1-isopentylcyclohexyl, $X_1$, $X_2$, $X_3$, $X_4$=a hydrogen atom, Y=carbonyl, Z=a hydrogen atom).

Step 6) N-[2-(1-isopentylcyclohexane)carbonylthiophenyl]-1isopentylcyclohexanecarboxamide (formula (XI); R=1-isopentylcyclohexyl, $X_1$, $X_2$, $X_3$, $X_4$=a hydrogen atom, Y=carbonyl)

A pyridine solution (500 ml) containing 2-aminothiophenol (15.8 g) was stirred at room temperature and 2 equal volumes of 1-isopentylcyclohexanecarbonyl chloride was added dropwise thereto. After completion of addition, the solution was stirred for 2 hours at 60° C. and allowed to cool. After removal of pyridine under reduced pressure, water was added and the solution was extracted with ethyl acetate. The organic layer was washed with an aqueous solution of saturated sodium bicarbonate, hydrochloric acid, and saturated brine, in this order, and dried over anhydrous sodium sulfate. The resulting solution was concentrated under reduced pressure to give the desired compound in the form of a crude oily substance (60 g).

Step 7) The crude product obtained in the above step 6) (60 g) was dissolved in a mixed solvent of methanol (60 ml)-tetrahydrofuran (60 ml) in the atmosphere of argon. Potassium hydroxide (24.2 g) was added thereto and the solution was stirred for 1 hour at room temperature. After stirring, water (50 ml) was added, the solution was washed with hexane (50 ml×3), and the aqueous layer was acidified with potassium hydrogen sulfate, followed by extraction with chloroform. The organic layer was washed with water and saturated brine, dried over anhydrous sodium sulfate, and the solvent was removed by evapolation under reduced pressure. The resulting deposited crystalline product was washed with pentane and collected by filtration to obtain the desired compound (23.1 g, yield: 60%).

EXAMPLES 12–18

The compounds shown in Tables 6 and 7 were obtained in the same manner as in Example 11.

TABLE 6

| Example | Compound | m.p. (° C.) | $^1$H NMR (CDCl$_3$ 300MHz) |
|---|---|---|---|
| 11 | (structure: 1-isopentyl-N-(2-mercaptophenyl)cyclohexanecarboxamide) | 109–110 | 8.34(1H, brs)<br>8.30(1H, dd, J=1.5, 8.4Hz)<br>7.50(1H, dd, J=1.5, 7.8Hz)<br>7.31(1H, ddd, J=1.5, 7.8, 8.4Hz)<br>7.00(1H, dt, J=1.5, 7.8Hz)<br>3.01(1H, s)<br>1.10–2.20(15H, m)<br>0.85(6H, d, J=6.6Hz) |
| 12 | (structure: 1-methyl-N-(2-mercaptophenyl)cyclohexanecarboxamide) | 82–83 | 8.42(1H, brs)<br>8.31(1H, dd, J=1.5, 8.4Hz)<br>7.50(1H, dd, J=1.5, 7.8Hz)<br>7.31(1H, ddd, J=1.5, 7.8, 8.4Hz)<br>7.00(1H, dt, J=1.5, 7.8Hz)<br>3.07(1H, s)<br>2.04–2.20(2H, m)<br>1.25–1.75(8H, m)<br>1.30(3H, s) |

TABLE 6-continued

| Example | Compound | m.p. (° C.) | ¹H NMR (CDCl₃ 300MHz) |
|---|---|---|---|
| 13 | | 66–68 | 8.17(1H, dd, J=1.5, 8.4Hz)<br>8.26(1H, brs)<br>7.50(1H, dd, J=1.5, 7.8Hz)<br>7.30(1H, ddd, J=1.5, 7.8, 8.4Hz)<br>7.00(1H, dt, J=1.5, 7.8Hz)<br>3.06(1H, s)<br>2.15–2.30(2H, m)<br>1.40–1.80(9H, m)<br>1.15(2H, m)<br>0.85(6H, d, J=6.6Hz) |
| 14 | | 120–121 | 8.37(1H, brs)<br>8.35(1H, dd, J=1.5, 8.4Hz)<br>7.50(1H, dd, J=1.5, 7.8Hz)<br>7.31(1H, ddd, J=1.5, 7.8, 8.4Hz)<br>7.00(1H, dt, J=1.5, 7.8Hz)<br>3.07(1H, s)<br>2.12–2.20(2H, m)<br>1.15–1.83(9H, m)<br>0.97(6H, d, J=6.9Hz) |
| 15 | | 84–85 | 8.38(1H, brs)<br>8.32(1H, dd, J=1.5, 8.4Hz)<br>7.50(1H, dd, J=1.5, 7.8Hz)<br>7.31(1H, ddd, J=1.5, 7.8, 8.4Hz)<br>7.00(1H, dt, J=1.5, 7.8Hz)<br>3.07(1H, s)<br>2.05–2.19(2H, m)<br>1.20–1.70(10H, m)<br>0.90(3H, t, J=7.2Hz) |
| 16 | | 93–94 | 8.38(1H, brs)<br>8.32(1H, dd, J=1.5, 8.4Hz)<br>7.50(1H, dd, J=1.5, 7.8Hz)<br>7.30(1H, ddd, J=1.5, 7.8, 8.4Hz)<br>7.00(1H, dt, J=1.5, 7.8Hz)<br>3.07(1H, s)<br>2.05–2.20(2H, m)<br>1.20–1.70(12H, m)<br>0.88(3H, t, J=7.2Hz) |

TABLE 7

| Example | Compound | m.p. (° C.) | ¹H NMR (CDCl₃ 300MHz) |
|---|---|---|---|
| 17 | | 97–98 | 8.37(1H, brs)<br>8.31(1H, dd, J=1.5, 8.4Hz)<br>7.50(1H, dd, J=1.5, 7.8Hz)<br>7.301H, ddd, J=1.5, 7.8, 8.4Hz)<br>7.00(1H, dt, J=1.5, 7.8Hz)<br>3.07(1H, s)<br>2.05–2.20(2H, m)<br>1.20–1.70(14H, m)<br>0.87(3H, t, J=7.2Hz) |

TABLE 7-continued

| Example | Compound | m.p. (° C.) | $^1$H NMR (CDCl$_3$ 300MHz) |
|---|---|---|---|
| 18 | (structure: 1-isobutylcyclohexanecarboxamide with 2-mercaptophenyl group) | 92–93 | 8.42(1H, brs)<br>8.32(1H, dd, J=1.5, 8.4Hz)<br>7.51(1H, dd, J=1.5, 7.8Hz)<br>7.31(1H, ddd, J=1.5, 7.8, 8.4Hz)<br>7.00(1H, dt, J=1.5, 7.8Hz)<br>3.07(1H, s)<br>2.06–2.20(2H, m)<br>1.20–1.95(11H, m)<br>0.89(6H, d, J=6.6Hz) |

Further, the compounds 11-1 and 11-2 shown in Table 8 were obtained in the same manner as in Example 11.

TABLE 8

| No. | Compound |
|---|---|
| 11-1 | (structure: 4-nitrobenzamide with 2-mercaptophenyl group) |
| 11-2 | (structure: 1-isobutylcyclohexanecarboxamide with 2-mercapto-4-trifluoromethylphenyl group) |

EXAMPLE 19

Synthesis of N-(2-mercapto-5-methoxyphenyl)-1-methylcyclohexanecarboxamide (formula (I); R=1-methylcyclohexyl, $X_1$, $X_3$, $X_4$=a hydrogen atom, $X_2$=methoxy, Y=carbonyl, Z=a hydrogen atom Step 8) S-(4-methoxy-2-nitrophenyl) N,N-dimethylthiocarbamate (formula (VIII); $R_{11}$, $R_{12}$=methyl, $X_1$, $X_3$, $X_4$=a hydrogen atom, $X_2$-methoxy).

A dimethylformamide solution (20 ml) containing 4-methoxy-2-nitrophenol (4.00 g) was added dropwise to a suspension of sodium hydride (1.04 g) in dimethylformamide (40 ml) at 0° C. under stirring. After completion of addition, the mixture was stirred for 30 minutes at room temperature, dimethylthiocarbamoyl chloride (3.65 g) was further added thereto and the solution was stirred for 1 hour at 80° C. After allowing the solution to cool, water was added thereto and the solution was extracted with ethyl acetate. The organic layer was washed with 5% hydrochloric acid, water, and saturated brine, and was dried over anhydrous sodium sulfate. The solution was concentrated and ether-hexane was added to the residue thus obtained. A deposited solid was collected by filtration to obtain a yellow solid (5.11 g, yield: 84%). Then, phenyl ether (10 ml) was added to the resulting product (3.50 g). After stirring for 1 hour at 210° C., the solution was allowed to cool. The resulting solution was purified by silica gel column chromatography (a developing solvent; hexane ethyl acetate= 7:1-3:2) to obtain the desired compound (3.35 g, yield: 96%).

Step 9) S-[2-(1-methylcyclohexanecarbonylamino)-4-methoxyphenyl] N,N-dimethylthiocarbamate (formula (IX); R=1-methylcyclohexyl, $R_{11}$, $R_{12}$=methyl, $X_1$, $X_3$, $X_4$=a hydrogen atom, $X_3$=methoxy, Y=carbonyl)

An ethyl acetate solution (75 ml) containing the compound (2.00 g) obtained in the above step 8) and SnCl$_2$·2H$_2$O (3.65 g) was stirred at room temperature overnight. Ethyl acetate (100 ml) was added to the solution and, then, an aqueous sodium hydroxide was further added thereto. Magnesium sulfate was added to the mixture and solid deposited was filtered off. The filtrate was concentrated to obtain S-(2-amino-4-methoxyphenyl) N,N-dimethylthiocarbamate (1.64 g, yield: 93%). After addition of pyridine (2.9 ml) and chloroform (20 ml) thereto, 1-methylcyclohexanecarbonyl chloride (1.39 g) was added dropwise thereto at room temperature under stirring, followed by stirring for 1 hour. After distilling off the solvent, water was added and the solution was extracted with ethyl acetate. The organic layer was washed with water and saturated brine, and was dried over anhydrous sodium sulfate. The residue obtained by concentration was purified by silica gel column chromatography (a developing solvent; hexane:ethyl acetate=3:1) to obtain the desired compound (2.41 g, yield: 95%).

Step 10) The compound obtained in the above step 9) (250 mg) was added to a solution containing potassium hydroxide (140 mg) and methanol (1.5 ml)-tetrahydrofuran (0.5 ml), and the mixture was refluxed for 30 minutes under heating. After allowing to cool, water was added and the aqueous layer was washed with hexane. The solution was acidified by adding an aqueous potassium hydrogensulfate, followed by extraction with ethyl acetate. The organic layer was washed with water and a saturated brine, and was dried over anhydrous sodium sulfate. The residue obtained after concentration was purified by column chromatography (a developing solvent; hexane:ethyl acetate=40:1) to obtain the desired compound (104 mg, yield: 52%)

EXAMPLES 20–24

The compounds shown in Table 9 were obtained in the same manner as in Example 19.

TABLE 9
| Example | Compound | m.p. (° C.) | ¹H NMR (CDCl₃ 300MHz) |
|---|---|---|---|
| 19 | 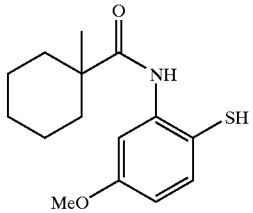 | Oil | 8.75(1H, brs)<br>8.19(1H, dd, J=2.7Hz)<br>7.42(1H, d, J=8.4Hz)<br>6.57(1H, dd, J=2.7, 8.4Hz)<br>3.82(3H, s)<br>2.91(1H, s)<br>2.05–2.15(2H, m)<br>1.25–1.70(8H, m)<br>1.30(3H, s) |
| 20 | 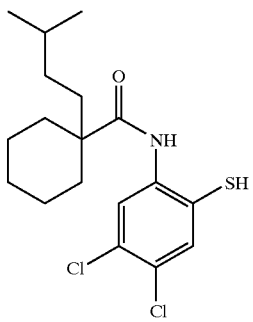 | 103–107 | 8.59(1H, s)<br>8.34(1H, brs)<br>7.61(1H, s)<br>3.10(1H, s)<br>2.00–2.20(2H, m)<br>1.10–1.75(13H, m)<br>0.86(6H, d, J=6.6Hz) |
| 21 | 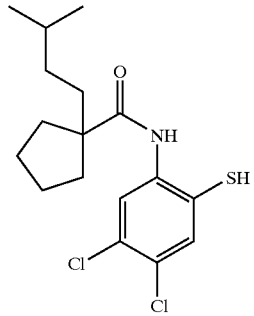 | 56–57 | 8.75(1H, s)<br>8.55(1H, brs)<br>7.60(1H, s)<br>3.09(1H, s)<br>1.10–2.20(13H, m)<br>0.87(6H, d, J=6.6Hz) |
| 22 | 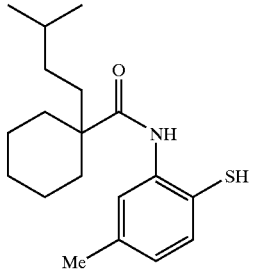 | 83.5–85.5 | 8.44(1H, brs)<br>8.22(1H, d, J=1.5Hz)<br>7.33(1H, d, J=7.8Hz)<br>6.83(1H, dd, J=1.5, 7.8Hz)<br>2.96(1H, s)<br>2.34(3H, s)<br>1.10–2.20(15H, m)<br>0.85(6H, d, J=6.6Hz) |
| 23 | 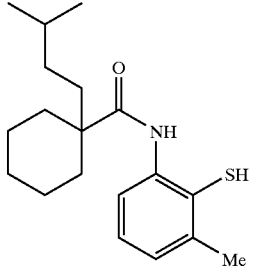 | 85–87 | 8.50(1H, brs)<br>8.17(1H, dd, J=1.5, 8.4Hz)<br>7.21(1H, t, J=8.4Hz)<br>7.00(1H, dd, J=1.5, 8.4Hz)<br>2.73(1H, brs)<br>2.47(3H, s)<br>2.05–2.20(2H, m)<br>1.10–1.75(13H, m)<br>0.86(6H, d, J=6.6Hz) |

TABLE 9-continued

| Example | Compound | m.p. (° C.) | $^1$H NMR (CDCl$_3$ 300MHz) |
|---------|----------|-------------|------------------------------|
| 24 | (structure) | 71–72 | 8.20(1H, brs)<br>8.12(1H, d, J=8.4Hz)<br>7.31(1H, s,)<br>7.10(1H, d, J=8.4Hz)<br>3.05(1H, s)<br>2.28(3H, s)<br>2.08–2.16(2H, m)<br>1.13–1.60(13H, m)<br>0.85(6H, d, J=6.6Hz) |

The compounds 19-1 through 19-9 shown in Table 10 were also obtained in the same manner as in Example 19.

TABLE 10

| No. | Compound |
|-----|----------|
| 19-1 | (structure) |
| 19-2 | (structure) |
| 19-3 | (structure) |
| 19-4 | (structure) |
| 19-5 | (structure) |
| 19-6 | (structure) |
| 19-7 | (structure) |
| 19-8 | (structure) |

TABLE 10-continued

| No. | Compound |
| --- | --- |
| 19-9 | (structure: 1-methylcyclohexane-1-carboxamide with N-H attached to a benzene ring bearing F ortho, SH, and F para; carbonyl C=O on cyclohexane) |

EXAMPLE 25

Synthesis of S-[2-(1-isopentylcyclohexanecarbonylamino) phenyl] thioacetate (formula (I); R=l-isopentylcyclohexyl, $X_1$, $X_2$, $X_3$, $X_4$=a hydrogen atom, Y=carbonyl, Z=acetyl)

Step 4) Acetyl chloride (0.17 ml) was added dropwise to a chloroform solution (10 ml) containing N-(2-mercaptophenyl)-1-isopentylcyclohexanecarboxamide (600 mg) obtained in the same manner as in step 2) of Example 9, step 7) of Example 11, or the step 10) of Example 19 and pyridine (0.48 ml) at room temperature under stirring. The solution was stirred for 1 hour. The residue obtained after concentration was purified by silica gel column chromatography (a developing solvent hexane:ethyl acetate=12:1) to obtain the desired compound (666 mg, yield: 98%).

EXAMPLE 26

Synthesis of S-[2-[1-(2-ethylbutyl) cyclohexanecarbonylamino]-phenyl] 2-methylthiopropionate (formula (I); R=1-(2-ethylbutyl)cyclohexyl, $X_1$, $X_2$, $X_3$, $X_4$=a hydrogen atom, Y=carbonyl, Z=isobutyryl)

Step 4) Isobutyryl chloride (15.0 ml) was added dropwise to a chloroform solution (300 ml) containing N-(2-mercaptophenyl)-1-(2-ethylbutyl)cyclohexanecarboxamide (43.72 g) obtained in Example 10 and pyridine (27.7 ml) at room temperature under stirring. The solution was stirred for 1 hour. After concentration, hexane was added and the deposited solid was filtered off. The filtrate was concentrated and the resulting residue was purified by silica gel column chromatography (a developing solvent; hexane:ethyl acetate=15:1) to obtain the desired compound (50.72 g, yield: 95%).

EXAMPLE 27

Synthesis of S-[2-(1-isobutylcyclohexanecarbonylamino) phenyl] 2-methylthiopropionate (formula (I); R=l-isobutylcyclohexyl, $X_1$, $X_2$, $X_3$, $X_4$=a hydrogen atom, Y=carbonyl, Z=isobutyryl)

Step 4) Isobutyryl chloride (0.92 ml) was added dropwise to a chloroform solution (25 ml) containing N-(2-mercaptophenyl)-1-isobutylcyclohexanecarboxamide (2.50 g) obtained in Example 18 and pyridine (1.8 ml) at room temperature under stirring. The solution was stirred for 1 hour. The residue obtained after concentration was purified by silica gel column chromatography (a developing solvent; hexane:ethyl acetate=15:1) to obtain the desired compound (2.94 g, yield: 95%).

EXAMPLE 28

Synthesis of S-(2-(1-(2-ethylbutyl) cyclohexanecarbonylamino)-phenyl] 1-acetylpiperidine-4-thiocarboxylate (formula (I); R=1-(2-ethylbutyl)cyclohexyl, $X_1$, $X_2$, $X_3$, $X_4$=a hydrogen atom, Y=carbonyl, z=1-acetyl-4-piperidinecarbonyl)

Step 4) A chloroform solution (10 ml) containing N-(2-mercaptophenyl)-1-(2-ethylbutyl)cyclohexanecarboxamide (933 mg) obtained in Example 10 and pyridine (0.5 ml) was added dropwise to a chloroform solution (10 ml) containing 1-acetylisonipecotic acid (500 mg), 1-ethyl-3-(3-dimethylaminopropyl)carbodiimide hydrochloride (616 mg), and 1-hydroxybenzotriazole (435 mg) at room temperature. The solution was stirred for 1 hour. After stirring, water was added and the solution was extracted with ethyl acetate. The organic layer was washed with a saturated brine and dried over anhydrous sodium sulfate. The residue obtained after concentration was purified by silica gel column chromatography (a developing solvent; hexane ethyl acetate=4:1-chloroform:methanol=10:1) to obtain the desired compound (1.08 g, yield: 79%).

EXAMPLE 28'

The compound of Example 28 (formula (I); R=1-(2-ethylbutyl)-cyclohexyl, $X_1$, $X_2$, $X_3$, $X_4$=a hydrogen atom, Y=carbonyl, Z=1-acetyl-4-piperidinecarbonyl) was synthesized using another synthesis method.

Step 4) Triethylamine (541 ml) was added to an ethylacetate suspension (2 liters) containing 1-acetylisonipecotic acid (331 g) under a stream of argon. The solution was stirred under ice cooling. An ethyl acetate solution (400 ml) containing ethyl chlorocarbonate (185 ml) was added dropwise thereto and the mixture was further stirred for 100 min under spontaneous elevation of the temperature. After ice-cooling, an ethyl acetate solution (2 liters) of N-(2-mercaptophenyl)-1-(2-ethylbutyl)cyclohexanecarboxamide (618 g) obtained in Example 10 was added dropwise to the reaction solution, which was stirred further for 15 minutes under ice-cooling. After stirring, 1 N hydrochloric acid (1.3 liter) was added, the organic layer was washed successively with water, an aqueous saturated sodium bicarbonate, water, and a saturated brine, and dried over anhydrous sodium sulfate. The residue obtained after concentration was dissolved in diisopropyl ether (2.5 liter) and the solution was stirred for crystallization to obtain a crude crystal. The crystal was further dissolved in diisopropyl ether (5.5 liter) under heating and the solution was stirred for crystallization to obtain the desired compound (505 g, yield: 55%).

EXAMPLE 29–65

The compounds shown in Tables 11–17 were obtained in the same manner as in Examples 25, 26, 27, 28, or 28'.

TABLE 11

| Example | Compound | m.p. (° C.) | $^1$H NMR (CDCl$_3$ 300MHz) |
|---|---|---|---|
| 25 | 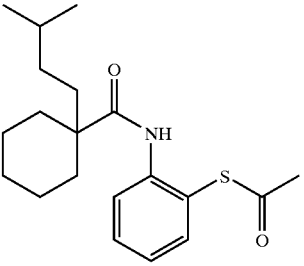 | 54–55 | 8.34(1H, dd, J=1.5, 8.4Hz)<br>8.05(1H, brs)<br>7.46(1H, ddd, J=1.5, 7.8, 8.4Hz)<br>7.39(1H, dd, J=1.5, 7.8Hz)<br>7.12(1H, dt, J=1.5, 7.8Hz)<br>2.45(3H, s)<br>2.03(2H, m)<br>1.10–1.61(13H, m)<br>0.85(6H, d, J=6.6Hz) |
| 26 | 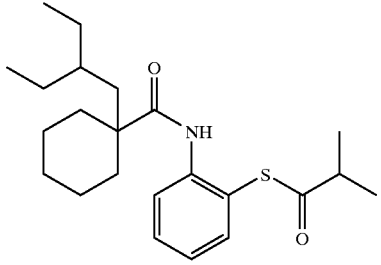 | 63.0–63.5 | 8.40(1H, dd, J=1.5, 8.4Hz)<br>8.12(1H, brs)<br>7.45(1H, ddd, J=1.5, 7.8, 8.4Hz)<br>7.38(1H, dd, J=1.5, 7.8Hz)<br>7.11(1H, dt, J=1.5, 7.8Hz)<br>2.94(2H, sept, J=6.9Hz)<br>1.95–2.20(2H, m)<br>1.15–1.75(15H, m)<br>1.30(6H, d, J=6.9Hz)<br>0.78(6H, t, J=6.9Hz) |
| 27 | 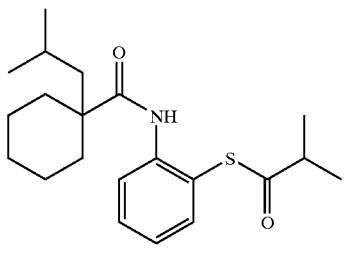 | 63.5–65.5 | 8.39(1H, dd, J=1.5, 8.4Hz)<br>8.10(1H, brs)<br>7.45(1H, ddd, J=1.5, 7.8, 8.4Hz)<br>7.38(1H, dd, J=1.5, 7.8Hz)<br>7.11(1H, dt, J=1.5, 7.8Hz)<br>2.94(2H, sept, J=6.9Hz)<br>1.95–2.10(2H, m)<br>1.10–1.85(11H, m)<br>1.29(6H, d, J=6.9Hz)<br>0.87(6H, d, J=6.6Hz) |
| 28 | 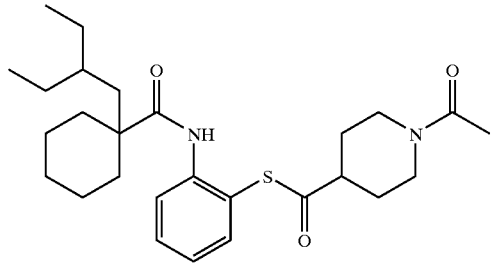 | 89.0–91.5 | 8.37(1H, dd, J=1.5, 8.4Hz)<br>8.03(1H, brs)<br>7.46(1H, ddd, J=1.5, 7.8, 8.4Hz)<br>7.36(1H, dd, J=1.5, 7.8Hz)<br>7.11(1H, dt, J=1.5, 7.8Hz)<br>4.58(1H, m)<br>3.88(1H, m)<br>3.18(1H, m)<br>2.91(1H, m)<br>2.82(1H, m)<br>1.95–2.20(4H, m)<br>2.11(3H, s)<br>1.15–1.85(17H, m)<br>0.78(6H, t, J=6.9Hz) |
| 29 | 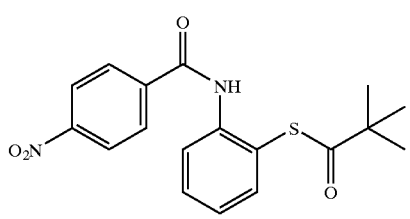 | 144–145 | 8.52(1H, brs)<br>8.42(1H, dd, J=1.5, 8.1Hz)<br>8.34(2H, dd, J=1.8, 6.9Hz)<br>8.00(2H, dd, J=1.8, 6.9Hz)<br>7.54(1H, ddd, J=1.5, 7.5, 8:1Hz)<br>7.45(1H, dd, J=1.5, 7.5Hz)<br>7.23(1H, dt, J=1.5, 7.5Hz)<br>1.34(9H, s) |
| 30 | 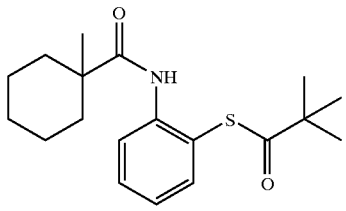 | 41–42 | 8.39(1H, dd, J=1.5, 8.4Hz)<br>8.07(1H, brs)<br>7.44(1H, ddd, J=1.5, 7.8, 8.4Hz)<br>7.36(1H, dd, J=1.5, 7.8Hz)<br>7.10(1H, dt, J=1.5, 7.8Hz)<br>1.96–2.05(2H, m)<br>1.15–1.65(8H, m)<br>1.35(9H, s)<br>1.22(3H, s) |

TABLE 12

| Example | Compound | m.p. (° C.) | ¹H NMR (CDCl₃ 300MHz) |
|---|---|---|---|
| 31 | | 61–62 | 8.32(1H, dd, J=1.5, 8.4Hz)<br>7.85(1H, brs)<br>7.20–7.50(7H, m)<br>7.10(1H, dt, J=1.5, 7.8Hz)<br>3.94(2H, s)<br>1.17(9H, s) |
| 32 | | 78.5–79.0 | 8.40(1H, dd, J=1.5, 8.4Hz)<br>8.17(1H, brs)<br>8.05(2H, m)<br>7.66(1H, ddd, J=1.5, 7.8, 8.4Hz)<br>7.43–7.60(4H, m)<br>7.17(1H, dt, J=1.5, 7.8Hz)<br>1.85–2.00(2H, m)<br>1.10–1.70(8H, m)<br>1.18(3H, s) |
| 33 | | 55–56 | 8.39(1H, dd, J=1.5, 8.4Hz)<br>8.04(1H, brs)<br>7.45(1H, ddd, J=1.5, 7.8, 8.4Hz)<br>7.36(1H, dd, J=1.5, 7.8Hz)<br>7.10(1H, dt, J=1.5, 7.8Hz)<br>2.00–2.03(2H, m)<br>1.10–1.60(13H, m)<br>1.35(9H, s)<br>0.85(6H, d, J=6.6Hz) |
| 34 | | 155–156 | 8.39(1H, dd, J=1.5, 8.4Hz)<br>7.98(1H, brs)<br>7.47(1H, ddd, J=1.5, 7.8, 8.4Hz)<br>7.09–7.38(7H, m)<br>5.85(1H, d, J=7.8Hz)<br>5.04(1H, dt, J=5.7, 7.8Hz)<br>3.20(1H, dd, J=6.0, 14.1Hz)<br>3.11(1H, dd, J=7.5, 14.1Hz)<br>1.97–2.10(5H, m)<br>1.00–1.80(13H, m)<br>0.81(6H, d, J=6.6Hz) |
| 35 | | 106–110 | 9.42(1H, s)<br>9.14(1H, d, J=5.1Hz)<br>8.90(1H, d, J=8.1Hz)<br>8.32(1H, d, J=7.8Hz)<br>8.12(1H, m)<br>7.89(1H, s)<br>7.58(1H, t, J=7.8Hz)<br>7.49(1H, d, J=7.8Hz)<br>7.24(1H, t, J=7.8Hz)<br>5.94(1H, brs)<br>1.89–2.03(2H, m)<br>1.07–1.60(13H, m)<br>0.80(6H, d, J=6.6Hz) |
| 36 | | 68–69 | 8.35(1H, dd, J=1.5, 8.4Hz)<br>7.93(1H, brs)<br>7.50(1H, ddd, J=1.5, 7.8, 8.4Hz)<br>7.40(1H, dd, J=1.5, 7.8Hz)<br>7.15(1H, dt, J=1.5, 7.8Hz)<br>4.28(2H, s)<br>1.96–2.09(2H, m)<br>1.09–1.65(13H, m)<br>0.85(6H, d, J=6.6Hz) |

TABLE 13

| Example | Compound | m.p. (° C.) | ¹H NMR (CDCl₃ 300MHz) |
|---|---|---|---|
| 37 | 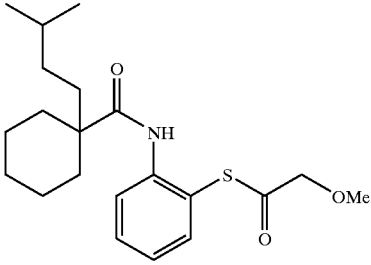 | 53–54 | 8.37(1H, dd, J=1.5, 8.4Hz)<br>7.98(1H, brs)<br>7.47(1H, ddd, J=1.5, 7.8, 8.4Hz)<br>7.39(1H, dd, J=1.5, 7.8Hz)<br>7.13(1H, dt, J=1.5, 7.8Hz)<br>4.19(2H, s)<br>3.58(3H, s)<br>1.95–2.10(2H, m)<br>1.05–1.65(13H, m)<br>0.84(6H, d, J=6.6Hz) |
| 38 | 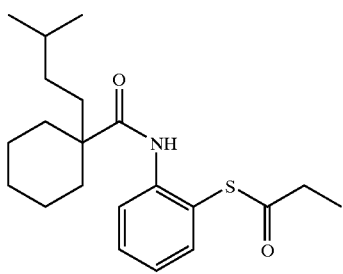 | 40–41 | 8.35(1H, dd, J=1.5, 8.4Hz)<br>8.06(1H, brs)<br>7.45(1H, ddd, J=1.5, 7.8. 8.4Hz)<br>7.39(1H, dd, J=1.5, 7.8Hz)<br>7.17(1H, dt, J=1.5, 7.8Hz)<br>2.72(2H, q, J=7.5Hz)<br>1.95–2.10(2H, m)<br>1.10–1.60(13H, m)<br>1.24(3H, t, J=7.2Hz)<br>0.85(6H, d, J=6.6Hz) |
| 39 | 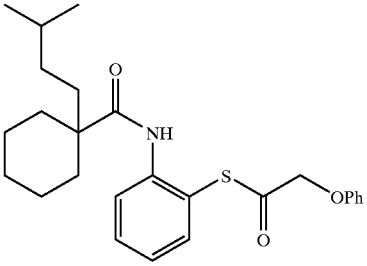 | 60.5–62.0 | 8.37(1H, dd, J=1.5, 8.4Hz)<br>7.90(1H, brs)<br>6.90–7.50(8H, m)<br>4.79(2H, s)<br>1.00–2.00(15, m)<br>0.83(6H, d, J=6.6Hz) |
| 40 | 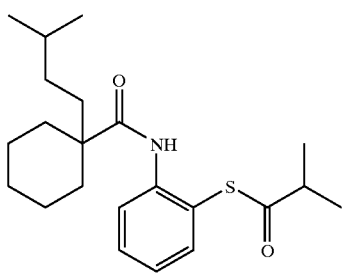 | 51–52 | 8.30(1H, dd, J=1.5, 8.4Hz)<br>8.00(1H, brs)<br>7.40(1H, ddd, J=1.5, 7.8, 8.4Hz)<br>7.33(1H, dd, J=1.5, 7.8Hz)<br>7.06(1H, dt, J=1.5, 7.8Hz)<br>2.88(1H, m)<br>1.94–1.98(2H, m)<br>1.07–1.51(13H, m)<br>1.24(6H, d, J=7.0Hz)<br>0.85(6H, d, J=6.6Hz) |
| 41 | 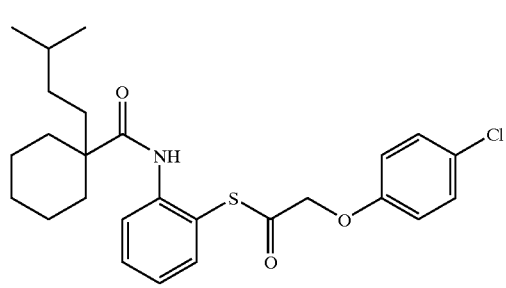 | 95–96 | 8.35(1H, dd, J=1.5, 8.4Hz)<br>7.87(1H, brs)<br>7.48(1H, ddd, J=1.5, 7.8, 8.4Hz)<br>7.37(1H, dd, J=1.5, 7.8Hz)<br>7.31(2H, m)<br>7.14(1H, dt, J=1.5, 7.8Hz)<br>6.93(2H, m)<br>4.78(2H, s)<br>1.90–1.94(2H, m)<br>1.07–1.58(13H, m)<br>0.83(6H, d, J=6.6Hz) |

TABLE 13-continued

| Example | Compound | m.p. (° C.) | ¹H NMR (CDCl₃ 300MHz) |
|---|---|---|---|
| 42 | (structure) | 52–53 | 8.31(1H, dd, J=1.5, 8.4Hz)<br>8.09(1H, brs)<br>7.45(1H, ddd, J=1.5, 7.8, 8.4Hz)<br>7.41(1H, dd, J=1.5, 7.8Hz)<br>7.10(1H, dt, J=1.5, 7.8Hz)<br>1.92–2.25(3H, m)<br>1.00–1.75(17H, m)<br>0.86(6H, d, J=6.6Hz) |

TABLE 14

| Example | Compound | m.p. (° C.) | ¹H NMR (CDCl₃ 300MHz) |
|---|---|---|---|
| 43 | (structure) | Oil | 8.36(1H, dd, J=1.5, 8.4Hz)<br>8.05(1H, brs)<br>7.44(1H, ddd, J=1.5, 7.8, 8.4Hz)<br>7.37(1H, dd, J=1.5, 7.8Hz)<br>7.12(1H, dt, J=1.5, 7.8Hz)<br>2.55–2.75(1H, m)<br>1.95–2.10(4H, m)<br>1.10–1.85(21H, m)<br>0.85(6H, d, J=6.6Hz) |
| 44 | (structure) | Amorphous | 8.38(1H, d, J=8.7Hz)<br>8.15(1H, brs)<br>8.04–8.08(2H, m)<br>7.66(1H, m)<br>7.48–7.55(4H, m)<br>7.16(1H, dt, J=1.2, 7.8Hz)<br>1.93–2.14(2H, m)<br>1.07–1.51(13H, m)<br>0.78(6H, d, J=6.6Hz) |
| 45 | (structure) | 136–138 | 8.41(1H, dd, J=1.5, 8.4Hz)<br>8.01(1H, brs)<br>7.46(1H, ddd, J=1.5. 7.8, 8.4Hz)<br>7.34(1H, dd, J=1.5, 7.8Hz)<br>7.23(1H, d, J=7.1Hz)<br>7.11(1H, dt, J=1.5, 7.8Hz)<br>5.72(1H, brs)<br>5.41(1H, brs)<br>4.69(1H, m)<br>1.95–2.58(6H, m)<br>1.05–1.70(13H, m)<br>0.85(6H, d, J=6.6Hz) |
| 46 | (structure) | 91–92 | 8.42(1H, dd, J=1.5, 8.4Hz)<br>7.99(1H, brs)<br>7.47(1H, ddd, J=1.5, 7.8, 8.4Hz)<br>7.37(1H, dd, J=1.5, 7.8Hz)<br>7.12(1H, dt, J=1.5, 7.8Hz)<br>2.64(1H, brs)<br>1.90–2.10(2H, m)<br>1.05–1.70(13H, m)<br>1.54(6H, s)<br>0.86(6H, d, J=6.6Hz) |

TABLE 14-continued

| Example | Compound | m.p. (° C.) | $^1$H NMR (CDCl$_3$ 300MHz) |
|---|---|---|---|
| 47 | 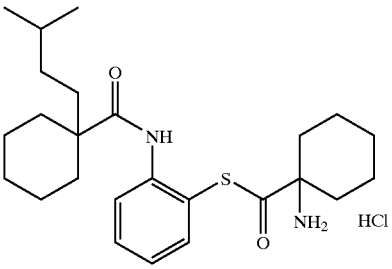 | 144–146 | 9.90(3H, brs)<br>8.07(1H, dd, J=1.5, 8.4Hz)<br>7.98(1H, s)<br>7.42(1H, ddd, J=1.5, 7.8, 8.4Hz)<br>7.41(1H, dd, J=1.5, 7.8Hz)<br>7.10(1H, dt, J=1.5, 7.8Hz)<br>1.95–2.20(2H, m)<br>1.10–1.85(21H, m)<br>0.84(6H, d, J=6.6Hz) |
| 48 | 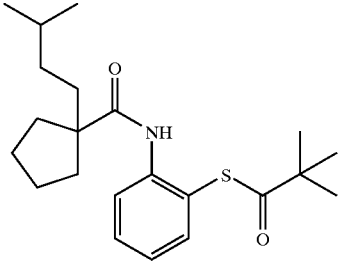 | 45–46 | 8.37(1H, dd, J=1.5, 8.4Hz)<br>7.93(1H, brs)<br>7.43(1H, ddd, J=1.5, 7.8, 8.4Hz)<br>7.35(1H, dd, J=1.5, 7.8Hz)<br>7.09(1H, dt, J=1.5, 7.8Hz)<br>2.05–2.20(2H, m)<br>1.45–1.75(9H, m)<br>1.36(9H, s)<br>1.10–1.25(2H, m)<br>0.86(6H, d, J=6.6Hz) |

TABLE 15

| Example | Compound | m.p. (° C.) | $^1$H NMR (CDCl$_3$ 300MHz) |
|---|---|---|---|
| 49 | 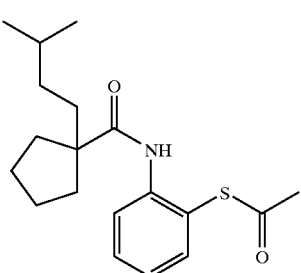 | 50–51 | 8.33(1H, dd, J=1.5, 8.4Hz)<br>7.95(1H, brs)<br>7.46(1H, ddd, J=1.5, 7.8, 8.4Hz)<br>7.40(1H, dd, J=1.5, 7.8Hz)<br>7.12(1H, dt, J=1.5, 7.8Hz)<br>2.46(3H, s)<br>2.05–2.25(2H, m)<br>1.40–1.80(9H, m)<br>1.10–1.25(2H, m)<br>0.87(6H, d, J=6.6Hz) |
| 50 | 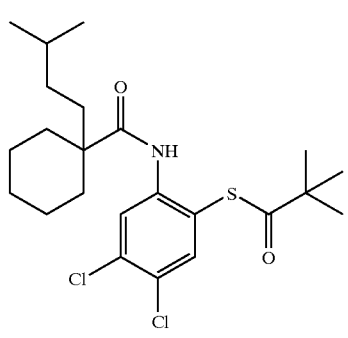 | 129–130 | 8.72(1H, s)<br>8.01(1H, brs)<br>7.44(1H, s)<br>1.90–2.10(2H, m)<br>1.10–1.75(13H, m)<br>1.35(9H, s)<br>0.85(6H, d, J=6.6Hz) |

TABLE 15-continued

| Example | Compound | m.p. (° C.) | ¹H NMR (CDCl₃ 300MHz) |
|---|---|---|---|
| 51 | 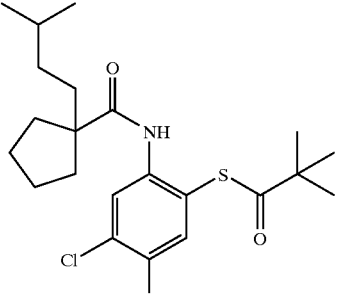 | 66–67 | 8.68(1H, s)<br>7.88(1H, brs)<br>7.43(1H, s)<br>2.05–2.20(2H, m)<br>1.30–1.75(9H, m)<br>1.35(9H, s)<br>1.05–1.20(2H, m)<br>0.86(6H, d, J=6.6Hz) |
| 52 | 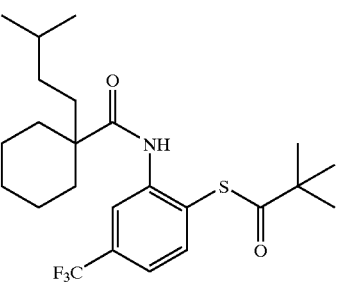 | 69–71 | 8.82(1H, d, J=1.5Hz)<br>8.16(1H, brs)<br>7.48(1H, d, J=8.1Hz)<br>7.34(1H, dd, J=1.5, 8.1Hz)<br>1.90–2.15(2H, m)<br>1.05–1.75(13H, m)<br>1.37(9H, s)<br>0.86(6H, d, J=6.6Hz) |
| 53 | 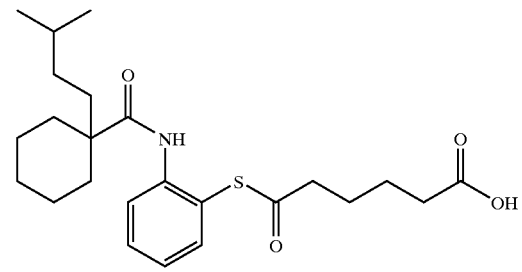 | Oil | 8.35(1H, dd, J=1.5, 8.4Hz)<br>8.05(1H, brs)<br>7.47(1H, ddd, J=1.5, 7.8, 8.4Hz)<br>7.39(1H, dd, J=1.5, 7.8Hz)<br>7.13(1H, dt, J=1.5, 7.8Hz)<br>2.74(2H, t, J=6.9Hz)<br>2.40(2H, t, J=6.9Hz)<br>1.90–2.10(2H, m)<br>1.05–1.90(17H, m)<br>0.86(6H, d, J=6.6Hz) |
| 54 | 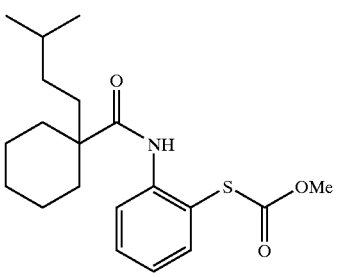 | Oil | 8.39(1H, dd, J=1.5, 8.4Hz)<br>8.27(1H, brs)<br>7.52(1H, dd, J=1.5, 7.8Hz)<br>7.47(1H, ddd, J=1.5, 7.8, 8.4Hz)<br>7.11(1H, dt, J=1.5, 7.8Hz)<br>3.84(3H, s)<br>2.00–2.10(2H, m)<br>1.10–1.65(13H, m)<br>0.85(6H, d, J=6.6Hz) |

TABLE 16

| Example | Compound | m.p. (° C.) | ¹H NMR (CDCl₃ 300MHz) |
|---|---|---|---|
| 55 | 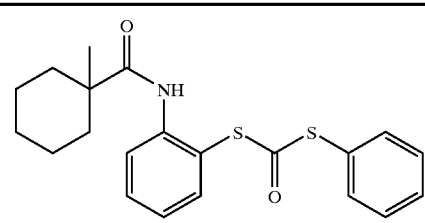 | Oil | 8.44(1H, dd, J=1.5, 8.4Hz)<br>8.29(1H, brs)<br>7.35–7.55(7H, m)<br>7.13(1H, dt, J=1.5, 7.8Hz)<br>1.95–2.15(2H, m)<br>1.25–1.70(8H, m)<br>1.27(3H, s) |

TABLE 16-continued

| Example | Compound | m.p. (° C.) | ¹H NMR (CDCl₃ 300MHz) |
|---|---|---|---|
| 56 | | 40–41 | 8.58(1H, brs)<br>8.42(1H, dd, J=1.5, 7.7Hz)<br>7.61(1H, dd, J=1.5, 7.7Hz)<br>7.53(1H, dt, J=1.5, 7.7Hz)<br>7.10–7.35(7H, m)<br>2.03–2.09(2H, m)<br>1.09–1.59(13H, m)<br>0.78(6H, d, J=6.6Hz) |
| 57 | | 103 | 8.80(1H, d, J=1.5Hz)<br>8.16(1H, brs)<br>7.48(1H, d, J=8.1Hz)<br>7.35(1H, dd, J=1.5, 7.8Hz)<br>1.37(9H, s)<br>1.30(9H, s) |
| 58 | | Oil | 8.22(1H, d, J=1.5Hz)<br>8.03(1H, brs)<br>7.26(1H, d, J=7.8Hz)<br>6.93(1H, dd, J=1.5, 7.8Hz)<br>2.43(3H, s)<br>2.38(3H, s)<br>1.10–2.10(15H, m)<br>0.85(6H, d, J=6.6Hz) |
| 59 | | 76.5–79.0 | 8.38(1H, dd, J=1.5, 8.4Hz)<br>8.13(1H, brs)<br>7.47(1H, ddd, J=1.5, 7.8, 8.4Hz)<br>7.40(1H, dd, J=1.5, 7.8Hz)<br>7.12(1H, dt, J=1.5, 7.8Hz)<br>2.46(3H, s)<br>2.00–2.15(2H, m)<br>1.15–1.70(15H, m)<br>0.79(6H, t, J=6.9Hz) |
| 60 | | 64.5–66.5 | 8.42(1H, dd, J=1.5, 8.4Hz)<br>8.11(1H, brs)<br>7.45(1H, ddd, J=1.5, 7.8, 8.4Hz)<br>7.36(1H, dd, J=1.5, 7.8Hz)<br>7.10(1H, dt, J=1.5, 7.8Hz)<br>1.95–2.15(2H, m)<br>1.10–1.75(15H, m)<br>1.36(9H, s)<br>0.79(6H, t, J=6.9Hz) |

TABLE 17

| Example | Compound | m.p. (° C.) | ¹H NMR (CDCl₃ 300MHz) |
|---|---|---|---|
| 61 | | 67.5–69.5 | 8.40(1H, dd, J=1.5, 8.4Hz)<br>8.06(1H, brs)<br>7.47(1H, ddd, J=1.5, 7.8, 8.4Hz)<br>7.39(1H, dd, J=1.5, 7.8Hz)<br>7.13(1H, dt, J=1.5, 7.8Hz)<br>4.20(2H, s)<br>3.59(3H, s)<br>1.95–2.15(2H, m)<br>1.10–1.75(15H, m)<br>0.79(6H, t, J=6.9Hz) |
| 62 | | 68.0–70.0 | 8.44(1H, dd, 1.5, 8.4Hz)<br>8.06(1H, brs)<br>7.47(1H, ddd, J=1.5, 7.8, 8.4Hz)<br>7.37(1H, dd, J=1.5, 7.8Hz)<br>7.12(1H, dt, J=1.5, 7.8Hz)<br>2.61(1H, s)<br>2.00–2.15(2H, m)<br>1.15–1.75(15H, m)<br>1.54(6H, s)<br>0.78(6H, t, J=6.9Hz) |
| 63 | | 62.0–63.0 | 8.39(1H, dd, J=1.5, 8.4Hz)<br>7.95(1H, brs)<br>7.48(1H, ddd, J=1.5, 7.8, 8.4Hz)<br>7.38(1H, dd, J=1.5, 7.8Hz)<br>7.32(2H, m)<br>7.14(1H, dt, J=1.5, 7.8Hz)<br>6.94(2H, m)<br>4.78(2H, s)<br>1.85–2.05(2H, m)<br>1.15–1.70(15H, m)<br>0.77(6H, t, J=6.9Hz) |
| 64 | | 61.0–65.0 | 8.40(1H, dd, J=1.5, 8.4Hz)<br>7.92(1H, brs)<br>7.49(1H, ddd, J=1.5, 7.8, 8.4Hz)<br>7.39(1H, dd, J=1.5, 7.8Hz)<br>7.33(2H, m)<br>7.15(1H, dt, J=1.5, 7.8Hz)<br>6.96(2H, m)<br>4.80(2H, s)<br>1.85–2.00(2H, m)<br>1.20–1.80(11H, m)<br>0.86(6H, d, J=6.6Hz) |
| 65 | | 61.0–64.0 | 8.38(1H, dd, J=1.5, 8.4Hz)<br>8.02(1H, brs)<br>7.47(1H, ddd, J=1.5, 7.8, 8.4Hz)<br>7.37(1H, dd, J=1.5, 7.8Hz)<br>7.12(1H, dt, J=1.5, 7.8Hz)<br>4.59(1H, m)<br>3.88(1H, m)<br>3.17(1H, m)<br>2.92(1H, m)<br>2.78(1H, m)<br>1.90–2.20(4H, m)<br>2.11(3H, s)<br>1.20–1.85(13H, m)<br>0.87(6H, d, J=6.6Hz) |

The compounds 25-1 through 25-109 shown in Tables 18 through were obtained in the same manner as in Examples 25 through 28.

TABLE 18

| No. | Compound |
|---|---|
| 25-1 | |
| 25-2 | |
| 25-3 | |
| 25-4 | |
| 25-5 | |
| 25-6 | |

TABLE 18-continued

| No. | Compound |
|---|---|
| 25-7 | |
| 25-8 | |
| 25-9 | |
| 25-10 | |
| 25-11 | |
| 25-12 | |

TABLE 19

| No. | Compound |
|---|---|
| 25-13 | |
| 25-14 | |
| 25-15 | |
| 25-16 | |
| 25-17 | |
| 25-18 | |
| 25-19 | |

TABLE 19-continued

| No. | Compound |
|---|---|
| 25-20 | |
| 25-21 | |
| 25-22 | |
| 25-23 | |
| 25-24 | |

TABLE 20

| No. | Compound |
|---|---|
| 25-25 | |

TABLE 20-continued

| No. | Compound |
|---|---|
| 25-26 | |
| 25-27 | |
| 25-28 | |
| 25-29 | |
| 25-30 | |
| 25-31 | |
| 25-32 | |

TABLE 20-continued

| No. | Compound |
|---|---|
| 25-33 | |
| 25-34 | |
| 25-35 | |
| 25-36 | |

TABLE 21

| No. | Compound |
|---|---|
| 25-37 | |
| 25-38 | |

TABLE 21-continued

| No. | Compound |
|---|---|
| 25-39 | |
| 25-40 | |
| 25-41 | |
| 25-42 | |
| 25-43 | |
| 25-44 | |

TABLE 21-continued

| No. | Compound |
|---|---|
| 25-45 | |
| 25-46 | |
| 25-47 | |
| 25-48 | |

TABLE 22

| No. | Compound |
|---|---|
| 25-49 | |

TABLE 22-continued

| No. | Compound |
|---|---|
| 25-50 | |
| 25-51 | |
| 25-52 | |
| 25-53 | |
| 25-54 | |
| 25-55 | |
| 25-56 | |
| 25-57 | |
| 25-58 | |
| 25-59 | |

TABLE 22-continued
| No. | Compound |
|---|---|
| 25-60 | |
| | |
TABLE 23
| No. | Compound |
|---|---|
| 25-61 | |
| 25-62 | |
| 25-63 | |
| 25-64 | |
TABLE 23-continued
| No. | Compound |
|---|---|
| 25-65 | |
| 25-66 | |
| 25-67 | |
| 25-68 | |
| 25-69 | |
| 25-70 | |
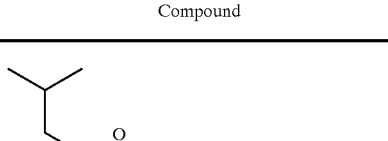

TABLE 23-continued

| No. | Compound |
|---|---|
| 25-71 | (structure) |
| 25-72 | (structure) |

TABLE 24

| No. | Compound |
|---|---|
| 25-73 | (structure) |
| 25-74 | (structure) |
| 25-75 | (structure) |
| 25-76 | (structure) |
| 25-77 | (structure) · HCl |
| 25-78 | (structure) · HCl |
| 25-79 | (structure) |

TABLE 24-continued
| No. | Compound |
|---|---|
| 25-80 | 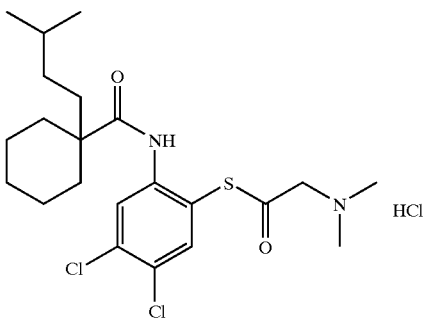 |
| 25-81 | 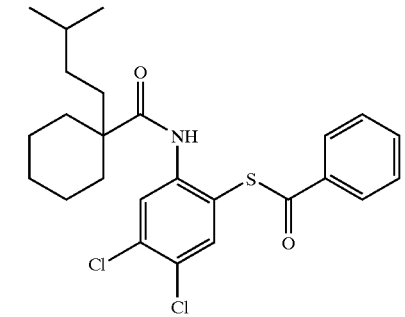 |
| 25-82 | 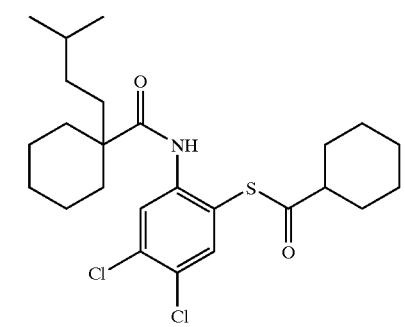 |
| 25-83 | 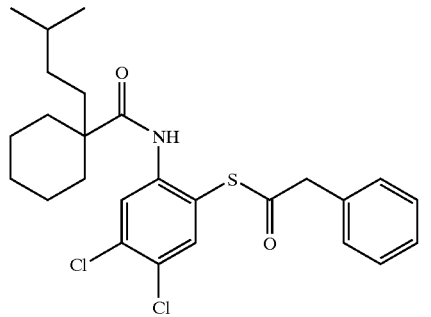 |
TABLE 24-continued
| No. | Compound |
|---|---|
| 25-84 | 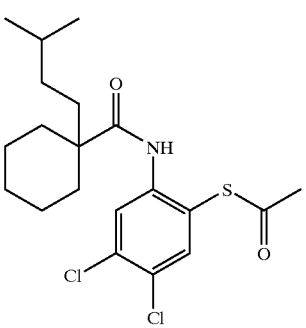 |
TABLE 25
| No. | Compound |
|---|---|
| 25-85 | 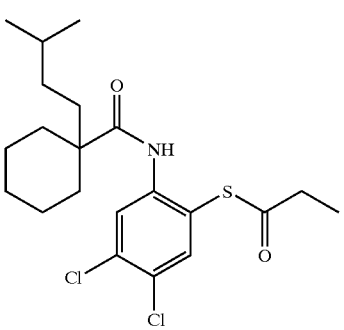 |
| 25-86 | 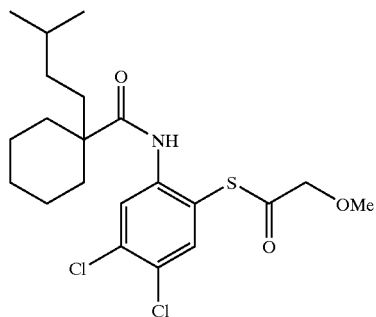 |
| 25-87 | 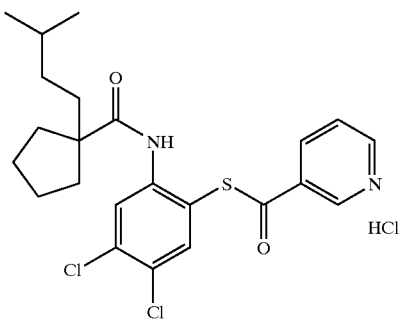 |

TABLE 25-continued

| No. | Compound |
|-----|----------|
| 25-88 | |
| 25-89 | |
| 25-90 | |
| 25-91 | |
| 25-92 | |
| 25-93 | |

TABLE 25-continued

| No. | Compound |
|-----|----------|
| 25-94 | |
| 25-95 | |
| 25-96 | |

TABLE 26

| No. | Compound |
|-----|----------|
| 25-97 | |
| 25-98 | |

TABLE 26-continued

| No. | Compound |
|---|---|
| 25-99 | (structure) |
| 25-100 | (structure) |
| 25-101 | (structure) |
| 25-102 | (structure) |
| 25-103 | (structure) |
| 25-104 | (structure) |
| 25-105 | (structure) |
| 25-106 | (structure) |
| 25-107 | (structure) |
| 25-108 | (structure) |

TABLE 27

| No. | Compound |
|---|---|
| 25-109 | (structure: N-pivaloyl-aminophenyl with S-pivaloyl thioester and Ph-C(=O)- group) |

Example 66

Synthesis of S-(4,5-dichloro-2-(1-isopropylcyclohexane-carbonylamino)phenyl] 2,2-dimethylthiopropionate (formula (I); R=1-isopropylcyclohexyl, $X_1$, $X_4$=a hydrogen atom, $X_2$, $X_3$=a chlorine atom, Y=carbonyl, Z=pivaloyl).

Step 4) A tetrahydrofuran (0.5 ml)-methanol (1 ml) solution containing S-[4,5-dichloro-2-(1-isopropylcyclohexanecarbonylamino)phenyl] N,N-dimethylthiocarbamate (86 mg) obtained in the same manner as in the step 9) of Example 19 and potassium hydroxide (50 mg) was refluxed for 30 minutes under heating. After the solution was allowed to cool, water was added and the aqueous layer was washed with hexane. Then, the aqueous layer was acidified with potassium hydrogensulfate, and was extracted with chloroform (10 ml). Pyridine (90 µl) was added to the resulting extract, and pivaloyl chloride (41 µl) was further added to the extract at room temperature under stirring. The solution was stirred for 1 hour. After concentration, the residue was purified by silica gel column chromatography (a developing solvent; hexane:ethyl acetate=20:1) to obtain the desired compound (24 mg, yield: 27%).

EXAMPLES 67–81

The compounds shown in Tables 28–30 were obtained in the same manner as in Example 66.

TABLE 28

| Example | Compound | m.p. (° C.) | $^1$H NMR (CDCl$_3$ 300MHz) |
|---|---|---|---|
| 66 | (structure) | 92–92 | 8.75(1H, s)<br>8.01(1H, brs)<br>7.44(1H, s)<br>1.95–2.10(2H, m)<br>1.10–1.75(9H, m)<br>1.34(9H, s)<br>0.91(6H, d, J=6.6Hz) |
| 67 | (structure) | 95–96 | 8.73(1H, s)<br>8.10(1H, brs)<br>7.44(1H, s)<br>1.85–2.00(2H, m)<br>1.10–1.70(8H, m)<br>1.34(9H, s)<br>0.89(6H, m)<br>0.35–0.47(4H, m) |
| 68 | (structure) | 109–110 | 8.67(1H, s)<br>7.61(1H, brs)<br>7.44(1H, s)<br>2.06(1H, quint, J=7.2Hz)<br>0.85–1.85(11H, m)<br>1.36(9H, s)<br>1.18(3H, d, J=6.6Hz) |

TABLE 28-continued
| Example | Compound | m.p. (° C.) | ¹H NMR (CDCl₃ 300MHz) |
|---|---|---|---|
| 69 | 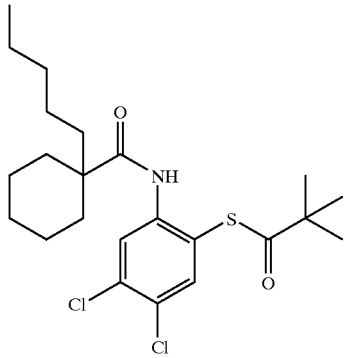 | 109–110 | 8.71(1H, s)<br>8.01(1H, brs)<br>7.44(1H, s)<br>1.95–2.05(2H, m)<br>1.05–1.70(18H, m)<br>1.35(9H, s)<br>0.84(3H, t, J=6.7Hz)<br>0.84(6H, d, J=6.6Hz) |
| 70 | 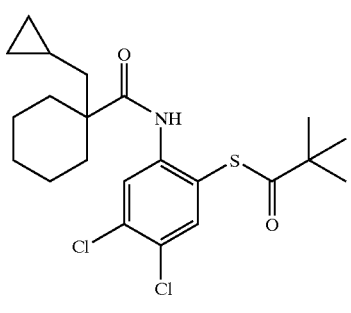 | 116–117 | 8.76(1H, s)<br>8.11(1H, brs)<br>7.44(1H, s)<br>2.02–2.15(2H, m)<br>1.20–1.65(8H, m)<br>1.34(9H, s)<br>0.55–0.65(1H, m)<br>0.35–0.45(2H, m)<br>0.01–0.02(4H, m) |
| 71 | 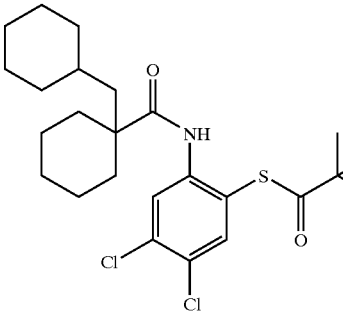 | 111–112 | 8.70(1H, s)<br>8.03(1H, brs)<br>7.44(1H, s)<br>1.90–2.10(2H, m)<br>0.75–1.75(21H, m)<br>1.36(9H, s) |
TABLE 29
| Example | Compound | m.p. (° C.) | ¹H NMR (CDCl₃ 300MHz) |
|---|---|---|---|
| 72 |  | 101–102 | 8.70(1H, s)<br>7.92(1H, brs)<br>7.43(1H, s)<br>2.00–2.15(2H, m)<br>1.30–1.65(13H, m)<br>1.35(9H, s)<br>1.05–1.15(2H, m)<br>0.85(6H, d, J=6.6Hz) |

TABLE 29-continued

| Example | Compound | m.p. (° C.) | ¹H NMR (CDCl₃ 300MHz) |
|---|---|---|---|
| 73 | | 53–54 | 8.70(1H, s)<br>7.68(1H, brs)<br>7.44(1H, s)<br>2.35–2.50(2H, m)<br>1.25–2.05(7H, m)<br>1.34(9H, s)<br>1.05–1.15(2H, m)<br>0.88(6H, d, J=6.6Hz) |
| 74 | | 93.0–93.5 | 9.39(1H, d, J=2.4Hz)<br>8.20(1H, brs)<br>7.93(1H, dd, J=2.4, 8.4Hz)<br>7.53(1H, d, J=8.4Hz)<br>1.95–2.15(2H, m)<br>1.00–1.75(13H, m)<br>1.37(9H, s)<br>0.85(6H, d, J=6.6Hz) |
| 75 | | 103–104 | 8.85(1H, d, J=1.5Hz)<br>8.14(1H, brs)<br>7.46(1H, d, J=7.8Hz)<br>7.35(1H, dd, J=1.5, 7.8Hz)<br>1.95–2.15(2H, m)<br>1.00–1.75(13H, m)<br>1.36(9H, s)<br>0.85(6H, d, J=6.6Hz) |
| 76 | | 77–78 | 8.57(1H, d, J=2.7Hz)<br>8.06(1H, brs)<br>7.27(1H, d, J=7.8Hz)<br>7.08(1H, dd, J=2.7, 7.8Hz)<br>1.95–2.10(2H, m)<br>1.05–1.65(13H, m)<br>1.34(9H, s)<br>0.84(6H, d, J=6.6Hz) |
| 77 | | 80–82 | 8.38(1H, d, J=8.7Hz)<br>7.99(1H, brs)<br>7.40(1H, dd, J=2.7, 8.7Hz)<br>7.35(1H, d, J=2.7Hz)<br>1.90–2.05(2H, m)<br>1.05–1.65(13H, m)<br>1.35(9H, s)<br>0.84(6H, d, J=6.6Hz) |

TABLE 30

| Example | Compound | m.p. (° C.) | $^1$H NMR (CDCl$_3$ 300MHz) |
|---|---|---|---|
| 78 | (structure with MeO substituent) | 76–77 | 8.20(1H, d, J=2.7Hz)<br>8.09(1H, brs)<br>7.22(1H, d, J=8.4Hz)<br>6.66(1H, dd, J=2.7, 8.4Hz)<br>3.85(3H, s)<br>1.95–2.05(2H, m)<br>1.05–1.65(13H, m)<br>1.34(9H, s)<br>0.84(6H, d, J=6.6Hz) |
| 79 | (structure with F substituent) | 55–56 | 8.34(1H, dd, J=3.0, 11.4Hz)<br>8.11(1H, brs)<br>7.31(1H, dd, J=6.3, 8.4Hz)<br>6.81(1H, ddd, J=3.0, 8.4, 11.4Hz)<br>1.95–2.15(2H, m)<br>1.05–1.65(13H, m)<br>1.34(9H, s)<br>0.84(6H, d, J=6.6Hz) |
| 80 | (structure with F, F substituents) | 97–98 | 8.44(1H, dd, J=8.1, 12.9Hz)<br>7.98(1H, brs)<br>7.19(1H, dd, J=8.4, 9.6Hz)<br>1.95–2.05(2H, m)<br>1.05–1.65(13H, m)<br>11.34(9H, s)<br>0.84(6H, d, J=6.6Hz) |
| 81 | (structure with F substituent) | 94–95 | 8.29–8.35(1H, m)<br>7.90(1H, brs)<br>7.09–7.19(2H, m)<br>1.92–2.06(2H, m)<br>1.09–1.55(13H, m)<br>1.35(9H, s)<br>0.85(6H, d, J=6.6Hz) |

The compounds 66-1 through 66-53 shown in Tables 31 through 35 were also obtained in the same manner as in Example 66.

TABLE 31

| No. | Compound |
|---|---|
| 66-1 | (structure) |
| 66-2 | (structure) |
| 66-3 | (structure) |
| 66-4 | (structure) |
| 66-5 | (structure) |
| 66-6 | (structure) |

TABLE 31-continued

| No. | Compound |
|---|---|
| 66-7 | (structure) |
| 66-8 | (structure) |
| 66-9 | (structure) |
| 66-10 | (structure) |
| 66-11 | (structure) |
| 66-12 | (structure) |

TABLE 32

| No. | Compound |
|---|---|
| 66-13 | (structure) |
| 66-14 | (structure) |
| 66-15 | (structure) |
| 66-16 | (structure) |
| 66-17 | (structure) |

TABLE 32-continued

| No. | Compound |
|---|---|
| 66-18 | (structure) |
| 66-19 | (structure) |
| 66-20 | (structure) |
| 66-21 | (structure) |
| 66-22 | (structure) |

TABLE 32-continued

| No. | Compound |
|---|---|
| 66-23 | |
| 66-24 | |

TABLE 33

| No. | Compound |
|---|---|
| 66-25 | |
| 66-26 | |

TABLE 33-continued

| No. | Compound |
|---|---|
| 66-27 | |
| 66-28 | |
| 66-29 | |
| 66-30 | |
| 66-31 | |

TABLE 33-continued

| No. | Compound |
|---|---|
| 66-32 | |
| 66-33 | |
| 66-34 | |
| 66-35 | |
| 66-36 | |

TABLE 34

| No. | Compound |
|---|---|
| 66-37 | |
| 66-38 | |
| 66-39 | |
| 66-40 | |

TABLE 34-continued

| No. | Compound |
|---|---|
| 66-41 | |
| 66-42 | |
| 66-43 | |
| 66-44 | |
| 66-45 | |
| 66-46 | |
| 66-47 | |
| 66-48 | |

TABLE 35

| No. | Compound |
|---|---|
| 66-49 | |
| 66-50 | |
| 66-51 | |
| 66-52 | |
| 66-53 | |

TABLE 35-continued

| No. | Compound |
|---|---|
| 82-1 | |

EXAMPLE 82

Synthesis of bis-[4,5-dichloro-2-(1-isopentylcyclohexanecarbonylamino)phenyl] disulfide (formula (I); R=1-isopentylcyclohexyl, $X_1$, $X_4$=a hydrogen atom, $X_2$, $X_3$=a chlorine atom, Y=carbonyl, Z=4,5-dichloro-2-(1-isopentylcyclohexanecarbonylamino)phenylthio)

Step 10) N-(4,5-dichloro-2-mercaptophenyl)-1-isopentylcyclohexanecarboxamide (formula (III-2); R=1-isopentylcyclohexyl, $X_1$, $X_4$=a hydrogen atom, $X_2$, $X_3$=a chlorine atom, Y=carbonyl)

A tetrahydrofuran (2 ml)-methanol (1 ml) solution containing S-[4,5-dichloro-2-(1-isopentylcyclohexanecarbonylamino)phenyl] N,N-dimethylthiocarbamate (400 mg) obtained in the same manner as in step 9 of Example 19 and potassium hydroxide (180 mg) was refluxed for 2 hours under heating and the resulting mixture was allowed to cool. After adding water thereto, the aqueous layer was washed with hexane, was acidified with a saturated aqueous potassium hydrogensulfate, and was extracted with chloroform. The organic layer was washed with water and a saturated brine, and dried over anhydrous sodium sulfate. After removing anhydrous sodium sulfate by filtration, the organic solvent was distilled off under reduced pressure to obtain the crude compound.

Step 3) A dimethyl sulfoxide solution (5 ml) of the crude product obtained in the above step 10) was stirred for 2 hours at 130° C. and the mixture was allowed to cool. Water was added to the solution, which was extracted with chloroform. The organic layer was washed with water and saturated brine, and dried over anhydrous sodium sulfate. The residue obtained after concentration was purified by silica gel column chromatography (a developing solvent; hexane:ethyl acetate=30:1) to obtain the compound (200 mg, yield: 60%).

TABLE 36

| Example | Compound | m.p. (° C.) | $^1$H NMR (CDCl$_3$ 300 MHz) |
|---|---|---|---|
| 82 | (structure: bis-disulfide with two 1-isopentylcyclohexanecarbonylamino groups on 4,5-dichlorophenyl rings connected by S–S) | Amorphous | 8.78(2H, s)<br>8.38(2H, brs)<br>7.24(2H, s)<br>1.80–2.00(4H, m)<br>1.00–1.75(26, m)<br>0.86(12H, d, J=6.6Hz) |

The compound 82-1 shown in Table 35 was obtained in the same manner as in Example 82.

EXAMPLE 83
Synthesis of 2-tetrahydrofurylmethyl 2-(1-isopentylcyclohexanecarbonylamino)phenyl disulfide (formula (I); R=1-isopentylcyclohexyl, $X_1$, $X_2$, $X_3$, $X_4$=a hydrogen atom, Y=carbonyl, Z=2-tetrahydrofurfurylmethylthio)

Step 5) An ethanol (6 ml)-water (6 ml) solution containing tetrahydrofurfuryl chloride (3.0 g) and sodium thiosulfate (4.13 g) was refluxed for 17 hours under heating and the mixture was allowed to cool. Ethanol was removed under reduced pressure and an aqueous solution of Bunte salt was obtained. An aqueous solution (1 ml) of N-(2-mercaptophenyl)-1-isopentylcyclohexanecarboxamide (380 mg) obtained as in Example 11 and sodium hydroxide (50 mg) was added dropwise to the solution at 0° C. and the solution was stirred for 1.5 hour. After addition of ether, the organic layer was successively washed with an aqueous sodium hydroxide, water, and a saturated brine, and dried over anhydrous sodium sulfate. The residue obtained by concentration under reduced pressure was purified by silica gel column chromatography (a developing solvent: hexane-:ethyl acetate=8:1) to obtain the desired compound (128 mg, yield: 24%).

EXAMPLE 84
Synthesis of phenyl 2-pivaloylaminophenyl disulfide (formula (I); R=t-butyl, $X_1$, $X_2$, $X_3$, $X_4$=a hydrogen atom, Y=carbonyl, Z=phenylthio)

Step 5') Trimethylsilane-imidazole (202 mg) was added to a carbon tetrachloride solution (5 ml) containing thiophenol (159 mg). The solution was stirred for 2 hours at room temperature. The deposited imidazole was filtered off to obtain a solution.

Then, sulfuryl chloride (97 mg) and triethylamine (1 drop) were successively added to a carbon tetrachloride solution (5 ml) containing bis-[2-(pivaloylamino)phenyl] disulfide (300 mg) obtained as in the step 1 of Example 1 at 0° C. The solution was stirred for 1.5 hour at the same temperature and was added dropwise to the above solution cooled in an ice-salt bath and the mixture was continuously stirred for 2.5 hour. After completion of the reaction, water was added and the solution was extracted with chloroform. The organic layer was washed with saturated brine and dried over anhydrous sodium sulfate. The solvent was removed under reduced pressure and the resulting residue was purified by silica gel column chromatography (a developing solvent; hexane:ethyl acetate=12:1) to obtain the desired compound (337 mg, yield: 74%).

TABLE 37

| Example | Compound | m.p. (° C.) | $^1$H NMR(CDCl$_3$ 300MHz) |
|---|---|---|---|
| 83 | (structure: 1-isopentylcyclohexanecarbonylamino on phenyl ring with S-S-CH$_2$-tetrahydrofuran) | Oil | 8.53(1H, brs)<br>8.44(1H, dd, J=1.5, 8.4Hz)<br>7.58(1H, dd, J=1.5, 7.8Hz)<br>7.40(1H, ddd, J=1.5, 7.8, 8.4Hz)<br>7.04(1H, dt, J=1.5, 7.8Hz)<br>4.14(2H, quint, J=6.6Hz)<br>3.86(1H, dt, J=8.4, 6.6Hz)<br>3.77(1H, dt, J=8.4, 6.6Hz)<br>2.96(1H, dd, J=6.6, 13.2Hz)<br>2.84(1H, dd, J=6.6, 13.2Hz)<br>1.80–2.20(5H, m)<br>1.10–1.75(14H, m)<br>0.86(6H, d, J=6.6Hz) |

TABLE 37-continued

| Example | Compound | m.p. (° C.) | ¹H NMR(CDCl₃ 300MHz) |
|---|---|---|---|
| 84 | (structure: 2-(phenyldisulfanyl)phenyl pivalamide) | Oil | 8.51(1H, brs)<br>8.40(1H, dd, J=1.5, 8.4Hz)<br>7.20–7.50(7H, m)<br>6.97(1H, dt, J=1.5, 7.8Hz)<br>1.30(9H, s) |

In the following, the results of the test for the CETP activity inhibitory effect of the compounds of the present invention are shown.

TEST EXAMPLES (1) Preparation of Donor Lipoprotein

Potassium bromide (KBr) was added to the plasma of healthy subjects (40 ml) to adjust specific gravity to d=1.125 g/ml. Density gradient centrifugation (227,000× g, 4° C., 17 hours) was conducted to obtain a fraction with specific gravity d>1.125 g/ml (HDL₃ fraction). The fraction thus obtained was dialyzed against a PBS solution [10 mM Na₂HPO₄/10 mM NaH₂PO₄/0.15 M NaCl/1 mM EDTA (pH 7.4)]. Then, tritium-labeled cholesterol (10 nM) (50.3 Ci/mM) was dissolved in 95% ethanol and added gradually to the above HDL₃ fraction under stirring. The solution was incubated for 18 hours at 37° C. [Tritium-labeled cholesterol was esterified by this procedure by the action of lecithin:cholesterol acyltransferase (LCAT) present on the surface of HDL₃ and taken up into the interior of HDL₃ as tritium-labeled cholesterylester ([³H]CE)]. After incubation, KBr was added and specific gravity was adjusted to d=1.21 g/ml. Density gradient centrifugation (227,000× g, 4° C., 17 hours) was conducted and the fraction with d<1.21 g/ml was harvested. The fraction thus obtained was dialyzed against the above PBS solution to obtain HDL₃ that took up [³H] CE ([³H]CE-HDL₃, specific gravity: 1.125<d<1.21, specific activity: 101,000 dpm/nM), which served as donor lipoprotein.

(2) Preparation of Acceptor Lipoprotein

Physiological saline (specific gravity d=1.006 g/ml) was layered upon the plasma of healthy subjects (100 ml). Density gradient centrifugation (227,000× g, 4° C., 4 hours) was conducted and the fraction with specific gravity d>1.006 g/ml was harvested. KBr was added to the fraction thus obtained to adjust specific gravity to d=1.063 g/ml and density gradient centrifugation (227,000× g, 4° C., 20 hours) was conducted to harvest the fraction with specific gravity d>1.063 g/ml. The thus-obtained fraction was dialyzed against the above PBS solution to obtain fractions containing IDL and LDL (specific gravity: 1.006<d<1.063), which served as acceptor lipoprotein.

TEST EXAMPLE 1

In Vitro CETP Activity Inhibitory Effect in Whole Plasma

Plasma containing [³H] CE-HDL₃ (600,000 dpm/ml) was prepared by adding donor lipoprotein obtained in the above (1) to plasma from healthy subjects. A sample solution was prepared using a 1:1 solution of N-methylpyrrolidone and polyethyleneglycol 400 as a solvent. The sample solution or the solvent alone (2 μl) and the plasma containing [³H]CE-HDL₃ (100 μl) were added to microtubes and incubated for 4 hours at 37° C. or 4° C. After ice cooling, a TBS solution [20 mM Tris/0.15 M NaCl (pH 7.4)] containing 0.15 M magnesium chloride and 0.3% dextran sulfate (100 μl) were added to each microtube and mixed well. After allowing the microtubes to stand at 4° C. for 30 minutes, centrifugation (8,000 rpm, 4° C., 10 minutes) was conducted and the radioactivity of the resulting supernatant (HDL fraction) was determined with a scintillation counter. The difference between the values obtained after incubation at 4° C. and 37° C. with the solvent alone was regarded as CETP activity and a decrease (%) of the measured values produced by the samples was regarded as inhibition rate (%) of CETP activity. Based on the inhibition rate (%) of CETP activity, IC₅₀ value of each sample was calculated.

The results are shown in Tables 38–48.

TEST EXAMPLE 2

Ex Vivo CETP Activity Inhibitory Effect of Plasma from Transgenic Mice

Samples were suspended in a 0.5% methylcellulose solution and administered orally using a plastic probe to transgenic mice having introduced human CETP gene (hereafter referred to as mice; prepared using the method described in Japanese Patent Application No. Hei 8-130660), which had been fasted overnight. Blood was collected before administration, and 6 hours after administration CETP activity in the plasma was determined using the following method.

Donor lipoprotein ([³H]CE-HDL₃, containing 0.21 μg cholesterol) obtained in the above (1), acceptor lipoprotein obtained in the above (2) (containing 21 μg of cholesterol), and 0.9 μl of mice plasma were added to microtubes. A total volume was adjusted to 600 μl/tube with a TBS solution [10 mM Tris/0.15 M NaCl (pH 7.4)]. The microtubes were incubated for 15 hours at 37° C. or 4° C. Then, an ice-cooled TBS solution (400 μl/tube) and a 0.3% dextran sulfate solution (100 μl/tube) containing 0.15 M magnesium chloride were added to the microtubes and mixed well. After allowing the microtubes to stand for 30 minutes at 4° C., centrifugation (8,000 rpm, 4° C., 10 minutes) was carried out and radioactivity of the resulting supernatant (HDL fraction) was determined with a scintillation counter. The difference between measured values obtained by incubating plasma of individual mice at 4° C. and 37° C. before administration of the samples were regarded as CETP activity and a decrease (%) of measured values after administration of samples was regarded as inhibition rate (%) of CETP activity.

The results are shown in Tables 38–48.

TABLE 38

| Example | CETP activity inhibition in whole plasma IC$_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 1 | 20 | | | | |
| 3 | 101 | | | | |
| 4 | 175 | | | | |
| 5 | 3 | | | | |
| 6 | 5 | | | | |
| 7 | 2 | | | | |
| 8 | 3 | | | 25 | |
| 9 | 99 | | | | |
| 11 | 5 | 27 | 45 | 57 | |
| 12 | 17 | | | | |
| 13 | 5 | | | | |
| 14 | 8 | | 9 | | |
| 15 | 12 | | | | |
| 16 | 8 | | | | |
| 17 | 8 | | | | |
| 18 | 6 | | | | |
| 19 | 179 | | | | |
| 20 | 16 | | | | |
| 21 | 9 | | | | |
| 22 | 56 | 22 | 44 | | |

TABLE 39

| Example | CETP activity inhibition in whole plasma IC$_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 23 | | | | 18 | |
| 24 | 29 | | | 29 | |
| 25 | 11 | 19 | 45 | 52 | |
| 26 | 7 | | 44 | | |
| 27 | 7 | | 31 | | |
| 28 | 6 | | 36 | | |
| 30 | 72 | | | | |
| 31 | 32 | | | | |
| 32 | 32 | | | | |
| 33 | 61 | 23 | 39 | 52 | 55 |
| 34 | 9 | | 4 | | |
| 35 | 4 | | | | |
| 36 | 16 | | 19 | | |
| 37 | 7 | 18 | 42 | 47 | |
| 38 | 6 | 15 | 40 | | |
| 39 | 11 | 17 | 41 | | |
| 40 | 23 | 20 | 48 | 64 | |
| 41 | 7 | 27 | 42 | | |
| 42 | 9 | 31 | 38 | | |
| 43 | 49 | | | | |

TABLE 40

| Example | CETP activity inhibition in whole plasma IC$_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 44 | 23 | | | | |
| 45 | 7 | 18 | 36 | | |
| 46 | 5 | 22 | 48 | | |
| 47 | 6 | | 31 | | |
| 48 | 49 | | 31 | 50 | |
| 49 | 6 | | 29 | | |
| 50 | 2 | | | | |
| 51 | 16 | | | | |
| 52 | 8 | | 8 | | |
| 53 | 8 | | | | |
| 54 | 12 | | | | |
| 55 | 65 | | | | |
| 56 | 13 | | 34 | | |
| 57 | 41 | | | | |
| 59 | 4 | | 44 | | |
| 60 | 41 | | 44 | | |
| 61 | 4 | | 38 | | |
| 62 | 4 | | 38 | | |
| 63 | 4 | | 43 | | |
| 64 | 4 | | 34 | | |

TABLE 41

| Example | CETP activity inhibition in whole plasma IC$_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 66 | 7 | | | | |
| 67 | 9 | | | | |
| 68 | 10 | | | | |
| 69 | 6 | | | | |
| 70 | 4 | | | | |
| 71 | 4 | | | | |
| 72 | 74 | | | | |
| 73 | 37 | | | | |
| 74 | 14 | | 5 | | |
| 75 | 25 | | 1 | | |
| 76 | 18 | | 4 | | |
| 77 | 17 | | 1 | | |
| 78 | | | 11 | | |
| 79 | 60 | 14 | 26 | | |
| 80 | 6 | | 12 | | |
| 81 | 21 | | 10 | | |
| 82 | 7 | | | | |
| 83 | 5 | | | | |
| 84 | 158 | | | | |

TABLE 42

| No. | CETP activity inhibition in whole plasma IC$_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 1-1 | 41 | | | | |
| 1-2 | 25 | | | | |
| 1-6 | 22 | | | | |
| 1-7 | 24 | | | | |
| 1-8 | 21 | | | | |
| 1-12 | 12 | | | | |
| 1-13 | 18 | | | | |
| 19-1 | 19 | | | | |
| 19-2 | 33 | | | | |
| 19-5 | 17 | | | | |
| 19-6 | 18 | | | | |
| 25-4 | 32 | | | | |
| 25-7 | 46 | | | | |
| 25-8 | 25 | | | | |

TABLE 42-continued

| No. | CETP activity inhibition in whole plasma $IC_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 25-12 | 33 | | | | |
| 25-13 | 28 | | | | |
| 25-14 | 30 | | | | |
| 25-16 | 41 | | | | |
| 25-17 | 23 | | | | |
| 25-18 | 19 | | | | |

TABLE 43

| No. | CETP activity inhibition in whole plasma $IC_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 25-19 | 22 | | | | |
| 25-20 | 48 | | | | |
| 25-21 | 28 | | | | |
| 25-22 | 27 | | | | |
| 25-23 | 25 | | | | |
| 25-25 | 24 | | | | |
| 25-26 | 22 | | | | |
| 25-27 | 21 | | | | |
| 25-28 | 21 | | | | |
| 25-30 | 21 | | | | |
| 25-31 | 21 | | | | |
| 25-32 | 20 | | | | |
| 25-33 | 18 | | | | |
| 25-34 | 21 | | | | |
| 25-35 | 27 | | | | |
| 25-36 | 30 | | | | |
| 25-37 | 24 | | | | |
| 25-38 | 20 | | | | |
| 25-39 | 22 | | | | |
| 25-40 | 23 | | | | |

TABLE 44

| No. | CETP activity inhibition in whole plasma $IC_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 25-41 | 26 | | | | |
| 25-42 | 22 | | | | |
| 25-44 | 9 | | | | |
| 25-45 | 13 | | 21 | | |
| 25-46 | 9 | | | 35 | |
| 25-47 | 29 | | | | |
| 25-48 | 23 | | | | |
| 25-49 | 21 | | | 16 | |
| 25-52 | 68 | 19 | | 40 | |
| 25-53 | 7 | | | 26 | |
| 25-54 | 6 | | | | |
| 25-55 | 10 | | | | |
| 25-56 | 7 | | | 24 | |
| 25-57 | 7 | | 18 | 46 | |
| 25-59 | 8 | | 20 | 37 | |
| 25-60 | 5 | | | | |
| 25-61 | 5 | | | 28 | |
| 25-63 | 21 | | | | 25 |
| 25-64 | 20 | | | | |
| 25-65 | 9 | | | | |

TABLE 45

| No. | CETP activity inhibition in whole plasma $IC_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 25-66 | 35 | | | | |
| 25-67 | 40 | | | | |
| 25-72 | 27 | | | | |
| 25-76 | 36 | | | | |
| 25-77 | 7 | | | | |
| 25-78 | 11 | | | | |
| 25-79 | 6 | | | | |
| 25-80 | 5 | | | | |
| 25-81 | 14 | | | | |
| 25-82 | 17 | | | | |
| 25-83 | 18 | | | | |
| 25-84 | 10 | | | 17 | |
| 25-85 | 7 | | | | |
| 25-86 | 10 | | | | |
| 25-87 | 6 | | | | |
| 25-91 | 22 | | | | |
| 25-92 | 19 | | | | |
| 25-93 | 22 | | | | |
| 25-94 | 18 | | | | |
| 25-95 | 18 | | | | |

TABLE 46

| No. | CETP activity inhibition in whole plasma $IC_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 25-96 | 8 | | | | |
| 25-97 | 9 | | | 19 | |
| 25-98 | 8 | | | | |
| 25-99 | 6 | | | | |
| 25-100 | 16 | | 25 | | |
| 25-101 | 7 | | 8 | | |
| 25-102 | 8 | | | 9 | |
| 25-103 | 12 | | | | |
| 25-104 | 9 | | | | |
| 25-105 | 6 | | | 14 | |
| 25-106 | 10 | | 29 | | |
| 25-107 | 11 | | 22 | | |
| 25-108 | 7 | | | 8 | |
| 66-3 | 24 | | | | |
| 66-4 | 28 | | | | |
| 66-9 | 9 | | | | |
| 66-10 | 23 | | | | |
| 66-11 | 22 | | | | |
| 66-12 | 17 | | | | |
| 66-14 | 11 | | | | |

TABLE 47

| No. | CETP activity inhibition in whole plasma $IC_{50}$ ($\mu$M) | CETP activity inhibitory rate in plasma from transgenic mouse (%) | | | |
|---|---|---|---|---|---|
| | | 10 mg/kg, p.o. | 30 mg/kg, p.o. | 100 mg/kg, p.o. | 300 mg/kg, p.o. |
| 66-16 | 8 | | | | |
| 66-17 | 18 | | | | |
| 66-18 | 11 | | | | |
| 66-21 | 41 | | | | |
| 66-22 | 19 | | | | |
| 66-23 | 13 | | | | |
| 66-24 | 12 | | | | |

TABLE 47-continued

| | CETP activity inhibition in whole plasma IC$_{50}$ ($\mu$M) | CETP activity inhibitory rate in plasma from transgenic mouse (%) | | | |
|---|---|---|---|---|---|
| No. | | 10 mg/kg, p.o. | 30 mg/kg, p.o. | 100 mg/kg, p.o. | 300 mg/kg, p.o. |
| 66-25 | 19 | | | | |
| 66-26 | 8 | | | | |
| 66-27 | 9 | | | | |
| 66-28 | 18 | | | | |
| 66-29 | 7 | | | | |
| 66-30 | 19 | | | | |
| 66-31 | 27 | | | | |
| 66-32 | 22 | | | | |
| 66-33 | 19 | | | | |
| 66-34 | 22 | | | | |
| 66-38 | 26 | | | | |
| 66-40 | 42 | | | | |
| 66-41 | 25 | | | | |

TABLE 48

| | CETP activity inhibition in whole plasma IC$_{50}$ ($\mu$M) | CETP activity inhibitory rate in plasma from transgenic mouse (%) | | | |
|---|---|---|---|---|---|
| No. | | 10 mg/kg, p.o. | 30 mg/kg, p.o. | 100 mg/kg, p.o. | 300 mg/kg, p.o. |
| 66-42 | 10 | | | | |
| 66-43 | 23 | | | | |
| 66-46 | 35 | | | | |
| 66-48 | 11 | | | | |
| 66-49 | 40 | | | | |
| 66-51 | 45 | | | | |
| 66-52 | 46 | | | | |
| 66-53 | 15 | | | | |
| 82-1 | 5 | | | | |

INDUSTRIAL APPLICABILITY

The above test results reveal that the compounds (I) of the present invention have an excellent CETP activity inhibitory effect. Thus, the compounds can reduce IDL, VLDL, and LDL, which aggravate atherosclerosis, and increase HDL that acts inhibitory thereto, and, therefore, are useful as a conventionally unknown, new type of a preventive or therapeutic agent for hyperlipidemia. The compound is also useful as a preventive or therapeutic agent for atherosclerotic diseases.

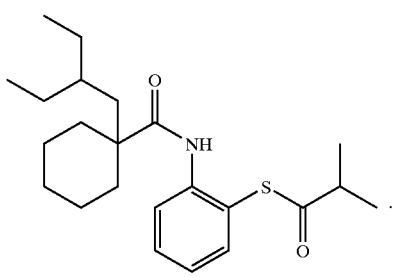

What is claimed is:

1. A compound of the formula:

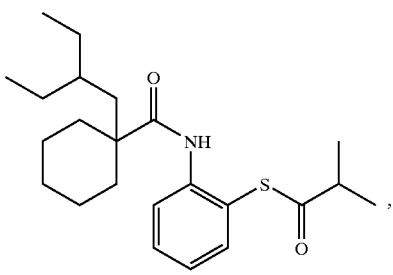

or a pharmaceutically acceptable salt, hydrate, or solvate thereof.

2. The compound of claim 1, wherein the compound is

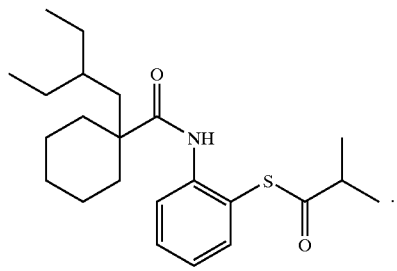

3. The compound of claim 1, wherein the compound is a pharmaceutically acceptable salt.

4. The compound of claim 1, wherein the compound is a hydrate.

5. The compound of claim 1, wherein the compound is a solvate.

6. A composition comprising (i) a compound of the formula:

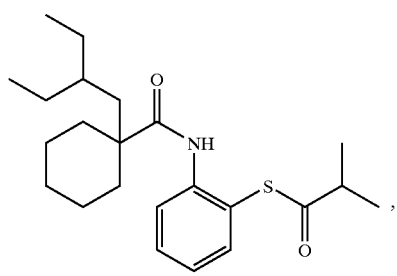

or a pharmaceutically acceptable salt, hydrate, or solvate thereof, and (ii) a pharmacologically acceptable carrier.

7. The composition of claim 6, wherein the compound is

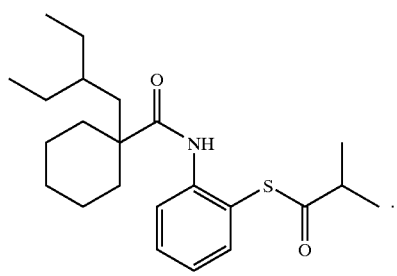

8. A method of inhibiting cholesterol ester transfer protein (CETP) activity in a patient, comprising administering to the patient a composition comprising (i) a compound of the formula:

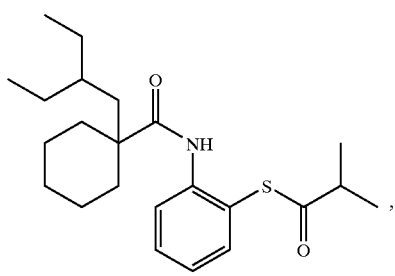

or a pharmaceutically acceptable salt, hydrate, or solvate thereof, and (ii) a pharmacologically acceptable carrier, whereby CETP activity is inhibited in the patient.

9. The method of claim 8, wherein the compound is

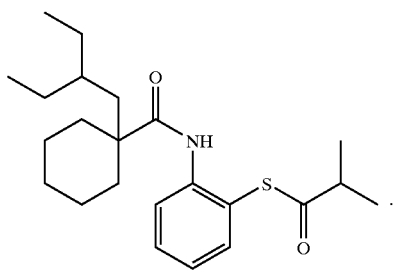

10. A method of increasing high density lipoprotein (HDL) in a patient, comprising administering to the patient a composition comprising (i) a compound of the formula:

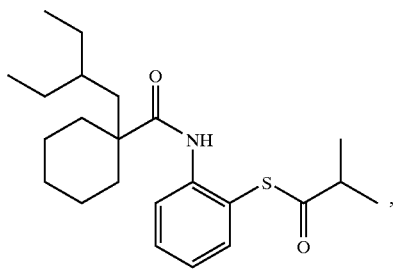

or a pharmaceutically acceptable salt, hydrate, or solvate thereof, and (ii) a pharmacologically acceptable carrier, whereby HDL is increased in the patient.

11. The method of claim 10, wherein the compound is

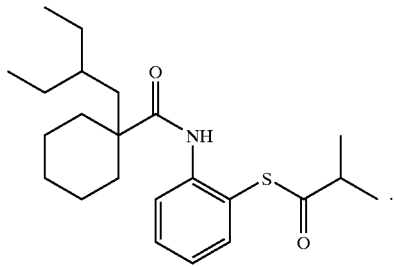

12. A method of decreasing low density lipoprotein (LDL) in a patient, comprising administering to the patient a composition comprising (i) a compound of the formula:

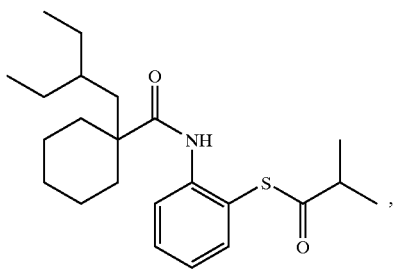

or a pharmaceutically acceptable salt, hydrate, or solvate thereof, and (ii) a pharmacologically acceptable carrier, whereby LDL is decreased in the patient.

13. The method of claim 12, wherein the compound is

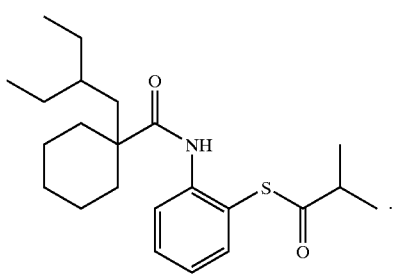

14. A method of treating or preventing atherosclerosis in a patient, comprising administering to the patient a composition comprising (i) a compound of the formula:

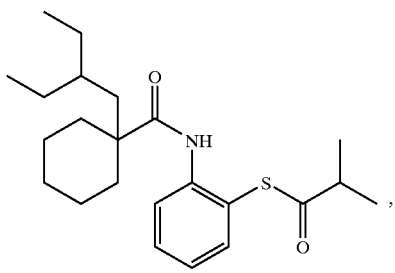

or a pharmaceutically acceptable salt, hydrate, or solvate thereof, and (ii) a pharmacologically acceptable carrier, whereby atherosclerosis is treated or prevented in the patient.

15. The method of claim 14, wherein the compound is

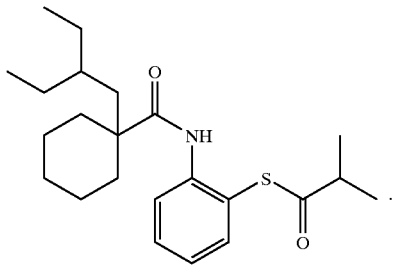

16. A method of treating or preventing hyperlipidemia in a patient, comprising administering to the patient a composition comprising (i) a compound of the formula:

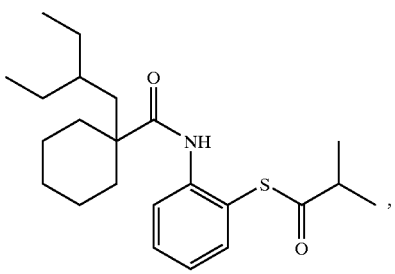

or a pharmaceutically acceptable salt, hydrate, or solvate thereof, and (ii) a pharmacologically acceptable carrier, whereby hyperlipidemia is treated or prevented in the patient.

17. The method of claim 16, wherein the compound is